US012559526B2

(12) United States Patent
Li et al.

(10) Patent No.: US 12,559,526 B2
(45) Date of Patent: Feb. 24, 2026

(54) COMPLEMENT COMPONENT 1S (C1s) DEFICIENT CELLS FOR PRODUCTION OF VACCINES AND BIOPHARMACEUTICAL PROTEINS

(71) Applicant: The Regents of the University of California, Oakland, CA (US)

(72) Inventors: Sophia Li, Santa Cruz, CA (US); Phillip Berman, Santa Cruz, CA (US)

(73) Assignee: The Regents of the University of California, Oakland, CA (US)

(*) Notice: Subject to any disclaimer, the term of this patent is extended or adjusted under 35 U.S.C. 154(b) by 1072 days.

(21) Appl. No.: 17/282,288

(22) PCT Filed: Oct. 9, 2019

(86) PCT No.: PCT/US2019/055440

§ 371 (c)(1),
(2) Date: Apr. 1, 2021

(87) PCT Pub. No.: WO2020/081328

PCT Pub. Date: Apr. 23, 2020

(65) Prior Publication Data

US 2021/0317168 A1 Oct. 14, 2021

Related U.S. Application Data

(60) Provisional application No. 62/745,872, filed on Oct. 15, 2018.

(51) Int. Cl.

| | |
|---|---|
| ***C07K 14/005*** | (2006.01) |
| ***C12N 9/00*** | (2006.01) |
| ***C12N 9/06*** | (2006.01) |
| ***C12N 9/22*** | (2006.01) |
| ***C12N 9/64*** | (2006.01) |
| ***C12N 15/11*** | (2006.01) |
| ***C12N 15/90*** | (2006.01) |

(52) U.S. Cl.

CPC ............ *C07K 14/005* (2013.01); *C12N 9/003* (2013.01); *C12N 9/22* (2013.01); *C12N 9/6424* (2013.01); *C12N 9/93* (2013.01); *C12N 15/11* (2013.01); *C12N 15/907* (2013.01); *C12Y 105/01003* (2013.01); *C12Y 603/01002* (2013.01); *C12N 2310/20* (2017.05); *C12N 2740/16022* (2013.01); *C12N 2800/80* (2013.01)

(58) Field of Classification Search

CPC ........ C07K 14/005; C12N 9/003; C12N 9/22; C12N 9/6424; C12N 9/93; C12N 15/11; C12N 15/907; C12N 2310/20; C12N 2740/16022; C12N 2800/80; C12Y 105/01003; C12Y 603/01002

See application file for complete search history.

(56) References Cited

U.S. PATENT DOCUMENTS

| | | | | |
|---|---|---|---|---|
| 9,731,002 | B2 * | 8/2017 | Berman | C07K 14/162 |
| 11,512,335 | B2 * | 11/2022 | Laux | C12Y 304/21109 |
| 2012/0192298 | A1 | 7/2012 | Weinstein et al. | |
| 2015/0152402 | A1 | 6/2015 | Song | |
| 2016/0130324 | A1 * | 5/2016 | Norton | C07K 14/765 435/254.2 |

OTHER PUBLICATIONS

Vijayan et al. A Chimeric HIV-1 gp120 Fused with Vaccinia Virus 14K (A27) Protein as an HIV Immunogen. PLoS One, Jul. 24, 2015; p. 1-25) (Year: 2015).*

Doran R. "Improvements to a gp 120 based subunit vaccine for HIV". Dissertation; Sep. 2018; retrieved from the Internet May 6, 2024. Retrieved fromhttps://escholarship.org/uc/item/0t82k5z1 (Year: 2018).*

Chakrabarti S, et al. Studies to Prevent Degradation of Recombinant Fc-Fusion Protein Expressed in Mammalian Cell Line and Protein Characterization. Int J Mol Sci. Jun. 9, 2016;17(6):913. doi: 10.3390/ijms17060913 (Year: 2016).*

Amano et al. (2007) "Genetic Analysis of Complement C1s Deficiency Associated with Systemic Lupus Erythematosus Highlights Alternative Splicing of Normal C1s Gene" Molecular Immunology, 5(6):1693-1702.

Byrne et al. (2018) "CRISPR/Cas9 Gene Editing for the Creation of an MGAT1-Deficient CHO Cell Line to Control HIV-1 Vaccine Glycosylation", PLOS Biology, 16(8), 23 pages.

Doran et al. (2018) "Development of a Stable MGAT1-CHO Cell Line to Produce Clade C gp120 with Improved Binding to Broadly Neutralizing Antibodies" Frontiers in Immunology, vol. 9, 13 pages.

Li et al. (2019) "Identification and CRISPR/Cas9 Inactivation of the C1s Proteolysis of Recombinant Proteins Produced in CHO Cells" Biotechnology and Bioengineering, 116(9):2130-2145.

Sandberg et al., (2006) "Mapping and partial characterization of proteases expressed by a CHO production cell line", Biotechnology and Bioengineering, 95(5):961-971.

Vijayan et al. (2015) "A Chimeric HIV-1 gp1 Fused with Vaccinia Virus 14K (A27) Protein as an HIV Immunogen", PLOS One, 1(7), 25 pages.

Yu et al., (2009) "Protease Cleavage Sites in HIV-1 gp120 Recognized by Antigen Processing Enzymes Are Consergved and Located at Receptor Binding Site", Journal of Virology, 84(3):1513-1526.

Wang et al. (2016) "Comprehensive Characterization of Reference Standard Lots of HIV-1 Subtype C Gp120 Proteins for Clinical Trials in Southern African Regions" Vaccines, 4(2):17.

* cited by examiner

*Primary Examiner* — Peter Paras, Jr.
*Assistant Examiner* — Gillian C. Reglas
(74) *Attorney, Agent, or Firm* — Shweta Chandra; Bozicevic, Field & Francis LLP

(57) ABSTRACT

The present disclosure reports that a calcium-dependent serine protease, complement component is (C1s) has been identified as a protease responsive for cleavage of exogenous polypeptides expressed in mammalian cell lines such as CHO cells. These CHO cell lines provide for increased yield of antigenically correct, uncleaved exogenous polypeptide as compared to unmodified CHO cells expressing the active C1s protease. C1s-deficient cell lines and methods for use of same for producing exogenous polypeptides, e.g., human immunodeficiency virus (HIV) envelope glycoprotein polypeptides, such as, gp120 or human Factor VIII are provided.

19 Claims, 18 Drawing Sheets

Specification includes a Sequence Listing.

| Lanes | MN gp120 | CHO supernatant | Inhibitor |
|---|---|---|---|
| 1 | + | - | - |
| 2 | + | + | - |
| 3 | + | + | 25 mM |
| 4 | + | + | 100 mM |
| 5 | + | + | 250 mM |

Transfection of plasmid vectors

CHO cells 2-3 weeks 120 kD
70 kD
50 kD

Screen for KO clones by western blot

Sanger sequencing of C1s gene knockout

Expansion to shake flasks

Wildtype C1s

5′GTTGACAGCCGCTCATGTTGTGG 3′ SEQ ID NO:26

-4 bp deletion

5′GTTGACAGCCGCTCATGTTGTGG 3′ SEQ ID NO:29

-3 bp deletion

5′GTTGACAGCCGCTCATGTTGTGG 3′ SEQ ID NO:30

COMPLEMENT COMPONENT 1S (C1s) DEFICIENT CELLS FOR PRODUCTION OF VACCINES AND BIOPHARMACEUTICAL PROTEINS

STATEMENT REGARDING FEDERALLY SPONSORED RESEARCH OR DEVELOPMENT

This invention was made with government support under grant nos. RO1AI113893 and RO1DA036335, awarded by the National Institutes of Health. The government has certain rights in the invention.

INTRODUCTION

Many pharmaceutically important polypeptides are expressed using mammalian cell lines. However, the yield of these pharmaceutically important polypeptides is reduced due to cleavage of the polypeptides expressed by the mammalian cell line by proteases expressed by these cell lines, reducing the yield of the full-length, uncleaved, product.

Human immunodeficiency virus type 1 (HIV-1) entry into a host cell is dependent on envelope glycoprotein (Env), which consists of two noncovalently bound subunits, the external gp120 and the transmembrane gp41. Env is present on virion surfaces as trimers of gp120-gp41 complexes and is involved in the binding of the virus to the host receptor and co-receptor(s). Env is also the target for the binding of neutralizing antibodies. gp120 is an important polypeptide frequently included in vaccines for HIV. However, when expressed in mammalian cell lines, gp120 is cleaved resulting in destruction of epitopes recognized by neutralizing antibodies and a decreased yield of uncleaved gp120 protein that retains immunogenicity. While it is known that cleavage of gp120 in mammalian cells is due to protease activity that results in cleavage in the V3 domain of gp120, the identity of protease(s) responsible for this cleavage is unknown.

Thus, there remains a need for the development of cell lines that do not have protease activity and can express uncleaved exogenous polypeptides.

SUMMARY

The present disclosure reports that a calcium-dependent serine protease, complement component is (C1s) has been identified as a protease responsive for cleavage of exogenous polypeptides expressed in mammalian cell lines such as CHO cells. The present disclosure describes C1s protease-deficient cell lines and shows that these cell lines produce significant amounts of uncleaved exogenous polypeptides. In certain aspects, these CHO cell lines provide for increased yield of antigenically correct, uncleaved exogenous polypeptide as compared to unmodified CHO cells expressing the active C1s protease. The present disclosure also provides methods for use of C1s-deficient cell lines for producing exogenous polypeptides, e.g., a polypeptide derived from human immunodeficiency virus (HIV) envelope glycoprotein polypeptides, such as, gp120, e.g., gp120 derived from a Clade B strain of HIV. In certain aspects, the gp120 protein lacks the endogenous signal sequence. In certain aspects, the gp120 protein comprises a heterologous signal sequence and lacks the endogenous signal sequence. In certain aspects, the gp120 protein comprises the endogenous signal sequence. In certain aspects, the gp120 protein comprises na endogenous signal sequence, and further includes a purification tag. In certain aspects the gp120 protein comprises a heterologous signal sequence, lacks the endogenous signal sequence, and further includes a purification tag. In certain aspects, the signal sequence is a herpes simplex virus glycoprotein D (gD) or a tissue plasminogen activator (tPA) signal sequence. In certain aspects, the purification tag includes sequences from gD or a polyhistidine (HIS) tag. Thus, the modified or unmodified gp120 protein produced from the cells disclosed herein is not proteolytically cleaved by the C1s protease. In certain embodiments, the C1s protease-deficient cell line is a CHO cell line, such as, a CHO K1, a CHO-S, a CHO-DX B11, or a CHO-DG44 cell line.

In certain aspects, a genetically modified mammalian cell line is provided, where the genetic modification is a mutation in the endogenous C1s gene encoding the calcium-dependent serine protease (C1s). In certain aspects, the mutation significantly decreases the protease activity of the C1s protease encoded by the mutated C1s gene. In certain aspects, the mutation includes a deletion, insertion, or a substitution in the C1s gene which results in (i) a lack of detectable expression of the C1s protease, (ii) expression of a truncated C1s protease, and/or (iii) a reduction in enzymatic activity of the C1s protease. In certain aspects, the genetically modified mammalian cell line comprising a mutation in the endogenous C1s gene may have a reduced C1s protease activity, e.g., a 50% reduction in C1s protease activity as compared to the unmodified parental cell line. In certain aspects, the reduction in protease activity may be measured by the reduction in cleavage of an exogenous polypeptide expressed by the genetically modified mammalian cell line as compared to the cleavage of the exogenous polypeptide expressed by the unmodified parental cell line. In certain aspects, the genetically modified mammalian cell line, e.g., a CHO cell line, comprises a deletion in exon 11 of C1s gene which introduces a premature stop codon into the C1s gene. In certain aspects, the genetically modified mammalian cell line, e.g., a CHO cell line, comprises a deletion in exon 11 of C1s gene which results in disruption of the serine protease domain encoded by exon 11.

In certain embodiments, the cell line may be additionally genetically modified to include a mutation of an endogenous gene encoding mannosyl (alpha-1,3)-glycoprotein beta-1,2-N-Acetylglucosaminyltransferase (Mgat1). In certain embodiments, the cell line may be a CHO-S or a CHO K1 cell line that has been genetically modified to include a mutation (i) in an endogenous gene encoding Mgat1 and (ii) in an endogenous C1s protease gene resulting in a cell line that has significantly reduced activity of both Mgat1 and C1s protease.

In certain embodiments, the cell line may be a CHO cell line that has been genetically modified to include (i) a mutation in an endogenous Mgat1, (ii) a mutation in an endogenous C1s protease gene, and (iii) to express an exogenous HIV envelope glycoprotein polypeptide (e.g., gp120 polypeptide) resulting in a cell line that has significantly reduced activity of both Mgat1 and C1s protease and expresses the HIV envelope glycoprotein polypeptide where at least 50% of the expressed HIV envelope glycoprotein polypeptide is a uncleaved HIV envelope glycoprotein polypeptide and at least 75% of the HIV envelope glycoprotein polypeptide produced by the genetically modified cell line comprises terminal mannose-5 glycans, e.g., terminal mannose-5, mannose-8, or mannose-9 glycans at the N-linked glycosylation site of gp120.

In certain embodiments, the cell line is the genetically modified cell line deposited with American Type Culture Collection (ATCC) as PTA-124141 or PTA-124142 that has been genetically modified to include a mutation in the endogenous C1s protease gene that significantly reduces C1s protease mediated cleavage of the gp120 polypeptide expressed by the cell line.

In certain aspects, the gp120 expressed by the genetically modified cell line may be fused to a signal sequence. The signal sequence may be a native signal sequence or a heterologous signal sequence. In certain aspects, the heterologous signal sequence may be cleaved off from the secreted polypeptide. In certain cases, the signal sequence may be linked to the polypeptide via a linker which may be a cleavable linker. In other embodiments, the signal sequence may not be cleaved off the secreted polypeptide.

In certain aspects, the polypeptide may be a fusion protein comprising a purification tag. The purification tag may be present at the N-terminus and/or the C-terminus of the polypeptide. In certain aspects, the purification tag may be present at the N-terminus, where the polypeptide comprises from the N-terminus to the C-terminus: native or heterologous signal sequence, purification tag, an optional linker sequence, and the envelope glycoprotein.

In certain aspects, the genetically modified cell line produces the uncleaved exogenous polypeptide at a concentration of at least 10 mg/L after 5 days of culturing.

In certain aspects, the cell line is of CHO K1 lineage or of CHO-S lineage.

In certain aspects, the cell line comprises an endogenous gene encoding glutamine synthetase (GS). In certain aspects, the cell line comprises an endogenous gene encoding dihydrofolate reductase (DHFR).

In other aspects, the cell line does not express a GS and/or a DHFR. For example, the cell line may include an inactivation, e.g., deletion, of an endogenous gene encoding glutamine synthetase (GS) and/or an endogenous gene encoding dihydrofolate reductase (DHFR).

BRIEF DESCRIPTION OF THE FIGURES

FIG. 2A. Lane 1. purified MN gp120 (clade B). Lane 2. MN gp120 (clade B)+10× concentrated CHO-S supernatant. FIG. 2B. Supernatant from clones of Bal gp120 (clade B) produced in the MGAT CHO-S Bal cell line (1.5d) cultured in a 96-well plate. All clones contain significant proteolytic activity.

FIG. 5A. Starting material: 5× concentrated; flow through (FT): 50× concentrated; Fraction 1: 20× concentrated; Fraction 2: 20× concentrated; Fraction 3: 20× concentrated; Fraction 4: 20× concentrated. Inhibitor: 1 mM 4-Aminobenzamidine dihydrochloride (4-AMB, a serine protease inhibitor that inhibits serine proteases including trypsin, plasmin and thrombin); 2 μl gp120+9 μl fraction. FIG. 5B. Fractions 1 and 2 (indicated by arrow) were analyzed by mass spectroscopy (MS).

FIG. 6A. Starting material: 5× concentrated; flow through (FT): 50× concentrated; Fraction 1: 20× concentrated; Fraction 2: 20× concentrated; Fraction 3: 20× concentrated; Fraction 4: 20× concentrated. Inhibitor: 1 mM 4-AMB (a serine protease inhibitor); 2 ul gp120+9 ul fraction. FIG. 6B. Fractions 1 and 2 (indicated by arrow) were analyzed by mass spectroscopy.

FIG. 8A. Purified MN gp120, a clade B protein, was combined with 10× concentrated CHO supernatant. Samples were reduced with DTT and probed on western blot using a goat polyclonal antibody against gp120. FIG. 8B provides details of samples loaded in lanes 1-5 in FIG. 8A. The serine protease inhibitor, 4-AMB was used.

DEFINITIONS

Figure 1:
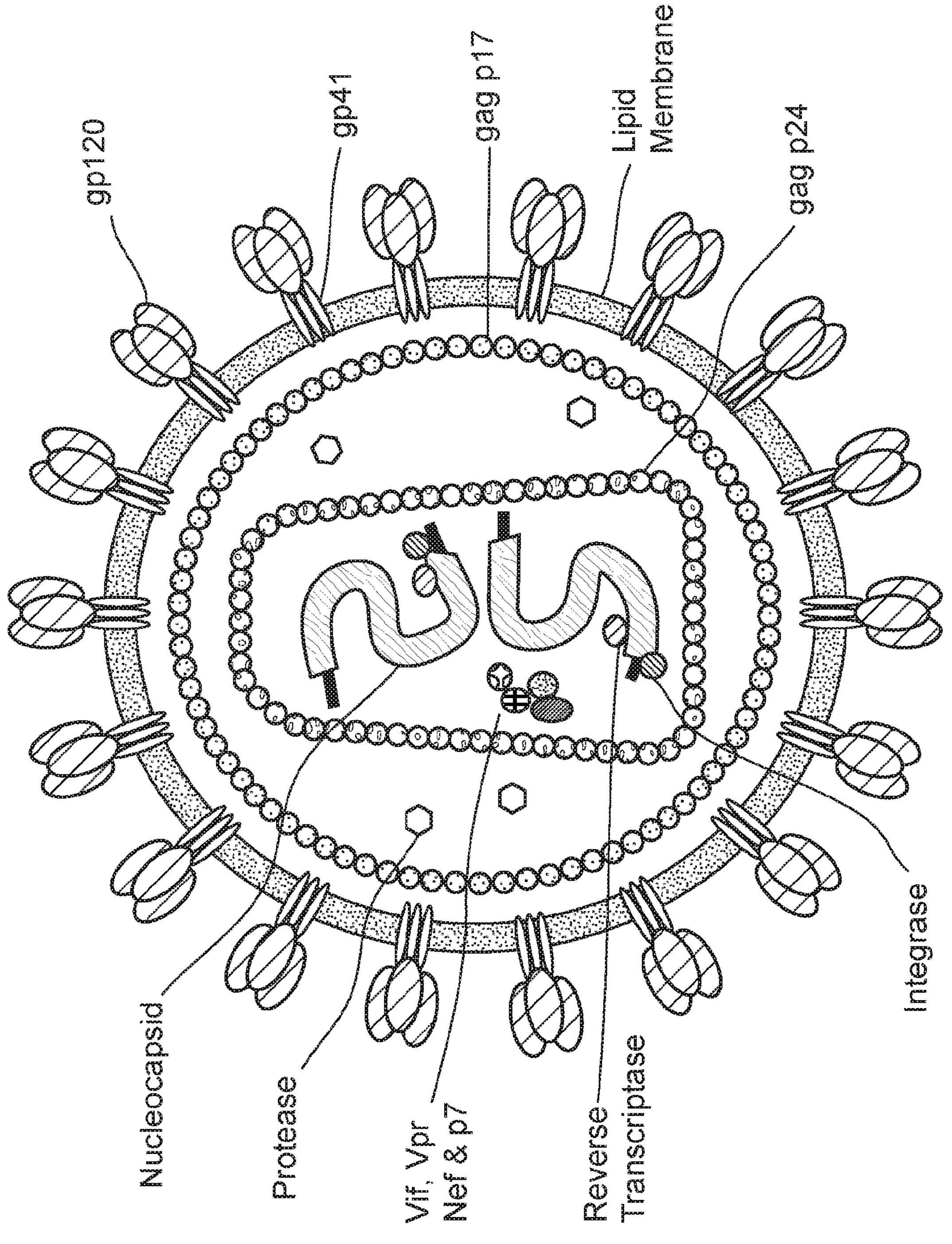
FIG. 1 depicts a simplified view of an HIV virus depicting the gp120 monomer present in the trimeric envelope protein of HIV.

The practice of the present invention will employ, unless otherwise indicated, conventional methods of medicine, chemistry, biochemistry, immunology, cell biology, molecular biology and recombinant DNA techniques, within the skill of the art. Such techniques are explained fully in the literature. All publications, patents and patent applications cited herein are hereby incorporated by reference in their entireties.

In describing the present invention, the following terms will be employed, and are intended to be defined as indicated below.

It must be noted that, as used in this specification and the appended claims, the singular forms "a", "an" and "the" include plural referents unless the content clearly dictates otherwise. Thus, for example, reference to "a cell" includes a mixture of two or more such cells, and the like. It is further noted that the claims can be drafted to exclude any optional element. As such, this statement is intended to serve as antecedent basis for use of such exclusive terminology as "solely," "only" and the like in connection with the recitation of claim elements or use of a "negative" limitation.

The term "heterologous" refers to two biological components that are not found together in nature. The components may be host cells, genes, or regulatory regions, such as promoters. Although the heterologous components are not found together in nature, they can function together, as when a promoter heterologous to a gene is operably linked to the gene. "Heterologous" in the context of recombinant cells can refer to the presence of a nucleic acid (or gene product, such as a polypeptide) that is of a different genetic origin than the host cell in which it is present. For example, a recombinant cell expressing a heterologous polypeptide refers to a cell that is genetically modified to introduce a nucleic acid encoding the polypeptide which nucleic acid is not naturally present in the cell.

"Endogenous" as used herein to describe a gene or a nucleic acid in a cell means that the gene or nucleic acid is native to the cell (e.g., a non-recombinant host cell) and is in its normal genomic and chromatin context, and which is not heterologous to the cell. C1s, Mgat1, glutamine synthetase, dihydrofolate reductase are examples of genes that are endogenous to mammalian cells, such as, CHO cells. When added to a cell, a recombinant nucleic acid would also be heterologous to the endogenous genes of the cell. Thus, in a chromosome, a heterologous nucleic acid would include a non-native (non-naturally occurring) nucleic acid that has integrated into the chromosome, or a non-native (non-naturally occurring) extrachromosomal nucleic acid. In contrast, a naturally translocated piece of chromosome would not be considered heterologous in the context of this patent application, as it comprises an endogenous nucleic acid sequence that is native to the mutated cell.

"Exogenous" as used herein describes a gene or a nucleic acid in a cell that has been introduced into the cell by genetic modification. "Exogenous" as used herein in the context of a polypeptide expressed by a cell refers to a polypeptide that is expressed by an exogenous gene or a nucleic acid introduced into the cell, In certain aspects, the exogenous gene or nucleic acid is not native to the cell.

"Recombinant" as used herein to describe a nucleic acid molecule means a polynucleotide of genomic, cDNA, semisynthetic, or synthetic origin which, by virtue of its origin or manipulation is not associated with all or a portion of the polynucleotide with which it is associated in nature. The term "recombinant" as used with respect to a protein or polypeptide means a polypeptide produced by expression of a recombinant polynucleotide. In general, the gene of interest is cloned and then expressed in transformed organisms, as described further below. The host organism expresses the foreign gene to produce the protein under expression conditions. Thus, for example, recombinant cells, such as a recombinant host cell, express genes that are not found within the native (naturally occurring) form of the cell or express a second copy of a native gene that is otherwise normally or abnormally expressed, under expressed or not expressed at all.

The term "transformation" or "genetic modification" refers to a permanent or transient genetic change induced in a cell following introduction of a new nucleic acid. Thus, a "genetically modified host cell" is a host cell into which a new (e.g., exogenous; heterologous) nucleic acid has been introduced. Genetic change ("modification") can be accomplished either by incorporation of the new DNA into the genome of the host cell, or by transient or stable maintenance of the new DNA as an episomal element. In eukaryotic cells, a permanent genetic change is generally achieved by introduction of the DNA into the genome of the cell and/or by deletion of DNA of the genome of the cell.

The terms "DNA regulatory sequences," "control elements," and "regulatory elements," used interchangeably herein, refer to transcriptional and translational control sequences, such as promoters, enhancers, polyadenylation signals, terminators, protein degradation signals, and the like, that provide for and/or regulate expression of a coding sequence and/or production of an encoded polypeptide in a host cell.

"Encode," as used in reference to a nucleotide sequence of nucleic acid encoding a gene product, e.g., a polypeptide, of interest, is meant to include instances in which a nucleic acid contains a nucleotide sequence that is the same as in a cell or genome that, when transcribed and/or translated into a polypeptide, produces the gene product. In some instances, a nucleotide sequence or nucleic acid encoding a gene product does not include intronic sequences.

"Substantially purified" generally refers to isolation of a substance (compound, polynucleotide, protein, or polypeptide) such that the substance comprises the majority percent of the sample in which it resides. Typically, in a sample, a substantially purified component comprises 50%, 80%-85%, or 90-95% of the sample. Techniques for purifying polynucleotides, oligonucleotides, and polypeptides of interest are well-known in the art and include, for example, ion-exchange chromatography, affinity chromatography and sedimentation according to density.

The term "operably linked" refers to a juxtaposition wherein the components so described are in a relationship permitting them to function in their intended manner. For instance, a promoter is operably linked to a nucleotide sequence if the promoter affects the transcription or expression of the nucleotide sequence.

A "host cell," as used herein, denotes an in vitro eukaryotic cell (e.g., a mammalian cell, such as, a CHO cell line), which eukaryotic cell can be, or has been, used as a recipient for a nucleic acid, and include the progeny of the original cell which has been genetically modified by the nucleic acid. It is understood that the progeny of a single cell may not necessarily be completely identical in morphology or in genomic or total DNA complement as the original parent, due to natural, accidental, or deliberate mutation. A "recombinant host cell" (also referred to as a "genetically modified host cell") is a host cell into which has been introduced a heterologous nucleic acid, e.g., an expression vector. For example, a subject eukaryotic host cell is a genetically modified eukaryotic host cell, by virtue of introduction into of a heterologous nucleic acid, e.g., an exogenous nucleic acid that is foreign to the eukaryotic host cell, or a recombinant nucleic acid that is not normally found in the eukaryotic host cell.

As used herein, the term "cell line" refers to a population of cells produced from a single cell and therefore consisting of cells with a uniform genetic makeup.

By "isolated" is meant, when referring to a polypeptide, that the indicated molecule is separate and discrete from the whole organism with which the molecule is found in nature or is present in the substantial absence of other biological macro-molecules of the same type. The term "isolated" with respect to a polynucleotide refers to a nucleic acid molecule devoid, in whole or part, of sequences normally associated with it in nature; or a sequence, as it exists in nature, but having heterologous sequences in association therewith; or a molecule disassociated from the chromosome.

The terms "polynucleotide," "nucleic acid" and "nucleic acid molecule" are used herein to include a polymeric form of nucleotides of any length, either ribonucleotides or deoxyribonucleotides. This term refers only to the primary structure of the molecule. Thus, the term also includes modifications, such as by methylation and/or by capping, and unmodified forms of the polynucleotide. More particularly, the terms "polynucleotide," "nucleic acid" and "nucleic acid molecule" include polydeoxyribonucleotides (containing 2-deoxy-D-ribose), polyribonucleotides (containing D-ribose), any other type of polynucleotide which is an N- or C-glycoside of a purine or pyrimidine base, and other polymers containing nonnucleotidic backbones, for example, polyamide (e.g., peptide nucleic acids (PNAs)) and polymorpholino (commercially available from the Anti-Virals, Inc., Corvallis, Oregon, as Neugene) polymers, and other synthetic sequence-specific nucleic acid polymers providing that the polymers contain nucleobases in a configuration which allows for base pairing and base stacking, such as is found in DNA and RNA. There is no intended distinction in length between the terms "polynucleotide," "nucleic acid" and "nucleic acid molecule," and these terms will be used interchangeably.

The terms "label" and "detectable label" refer to a molecule capable of being detected, including, but not limited to, radioactive isotopes, fluorescers, chemiluminescers, enzymes, enzyme substrates, enzyme cofactors, enzyme inhibitors, chromophores, dyes, metal ions, metal sols, ligands (e.g., biotin or haptens) and the like. The term "fluorescer" refers to a substance or a portion thereof that is capable of exhibiting fluorescence in the detectable range. Particular examples of labels that may be used with the invention include, but are not limited to, phycoerythrin, Alexa dyes, fluorescein, YPet, CyPet, Cascade blue, allophycocyanin, Cy3, Cy5, Cy7, rhodamine, dansyl, umbelliferone, Texas red, luminol, acradimum esters, biotin, green fluorescent protein (GFP), enhanced green fluorescent protein (EGFP), yellow fluorescent protein (YFP), enhanced yellow fluorescent protein (EYFP), blue fluorescent protein (BFP), red fluorescent protein (RFP), firefly luciferase, *Renilla* luciferase, NADPH, beta-galactosidase, horseradish peroxidase, glucose oxidase, alkaline phosphatase, chloramphenical acetyl transferase, and urease.

By "hybridizable" or "complementary" or "substantially complementary" it is meant that a nucleic acid (e.g. RNA, DNA) comprises a sequence of nucleotides that enables it to non-covalently bind, i.e. form Watson-Crick base pairs and/or G/U base pairs, "anneal", or "hybridize," to another nucleic acid in a sequence-specific, antiparallel, manner (i.e., a nucleic acid specifically binds to a complementary nucleic acid) under the appropriate in vitro and/or in vivo conditions of temperature and solution ionic strength. Standard Watson-Crick base-pairing includes: adenine (A) pairing with thymidine (T), adenine (A) pairing with uracil (U), and guanine (G) pairing with cytosine (C) [DNA, RNA]. In addition, for hybridization between two RNA molecules (e.g., dsRNA), and for hybridization of a DNA molecule with an RNA molecule (e.g., when a ssRNA target nucleic acid base pairs with a DNA PAM-containing oligonucleotide (also referred to herein as a "PAMmer"), when a DNA target nucleic acid base pairs with a guide RNA, etc.): guanine (G) can also base pair with uracil (U). For example, G/U base-pairing is partially responsible for the degeneracy (i.e., redundancy) of the genetic code in the context of tRNA anti-codon base-pairing with codons in mRNA. Thus, in the context of this disclosure, a guanine (G) (e.g., of a protein-binding segment (dsRNA duplex) of a guide RNA molecule; of a target nucleic acid base pairing with a guide RNA and/or a PAM-containing oligonucleotide, etc.) is considered complementary to both a uracil (U) and to an adenine (A). For example, when a G/U base-pair can be made at a given nucleotide position of a protein-binding segment (e.g., dsRNA duplex) of a guide RNA molecule, the position is not considered to be non-complementary, but is instead considered to be complementary.

Hybridization and washing conditions are well known and exemplified in Sambrook, J., Fritsch, E. F. and Maniatis, T. Molecular Cloning: A Laboratory Manual, Second Edition, Cold Spring Harbor Laboratory Press, Cold Spring Harbor (1989), particularly Chapter 11 and Table 11.1 therein; and Sambrook, J. and Russell, W., Molecular Cloning: A Laboratory Manual, Third Edition, Cold Spring Harbor Laboratory Press, Cold Spring Harbor (2001). The conditions of temperature and ionic strength determine the "stringency" of the hybridization.

Hybridization requires that the two nucleic acids contain complementary sequences, although mismatches between bases are possible. The conditions appropriate for hybridization between two nucleic acids depend on the length of the nucleic acids and the degree of complementarity, variables well known in the art. The greater the degree of complementarity between two nucleotide sequences, the greater the value of the melting temperature (Tm) for hybrids of nucleic acids having those sequences. For hybridizations between nucleic acids with short stretches of complementarity (e.g. complementarity over 35 or fewer, 30 or fewer, 25 or fewer, 22 or fewer, 20 or fewer, or 18 or fewer nucleotides) the position of mismatches can become important (see Sambrook et al., supra, 11.7-11.8). Typically, the length for a hybridizable nucleic acid is 8 nucleotides or more (e.g., 10 nucleotides or more, 12 nucleotides or more, 15 nucleotides or more, 20 nucleotides or more, 22 nucleotides or more, 25 nucleotides or more, or 30 nucleotides or more). The temperature and wash solution salt concentration may be adjusted as necessary according to factors such as length of the region of complementation and the degree of complementation.

It is understood that the sequence of a polynucleotide need not be 100% complementary to that of its target nucleic acid to be specifically hybridizable or hybridizable. Moreover, a polynucleotide may hybridize over one or more segments such that intervening or adjacent segments are not involved in the hybridization event (e.g., a loop structure or hairpin structure). A polynucleotide can comprise 60% or more, 65% or more, 70% or more, 75% or more, 80% or more, 85% or more, 90% or more, 95% or more, 98% or more, 99% or more, 99.5% or more, or 100% sequence complementarity to a target region within the target nucleic acid sequence to which it will hybridize. For example, an antisense nucleic acid in which 18 of 20 nucleotides of the antisense compound are complementary to a target region, and would therefore specifically hybridize, would represent 90 percent complementarity. In this example, the remaining noncomplementary nucleotides may be clustered or interspersed with complementary nucleotides and need not be contiguous to each other or to complementary nucleotides. Percent complementarity between particular stretches of nucleic acid sequences within nucleic acids can be determined using any convenient method. Exemplary methods include BLAST programs (basic local alignment search tools) and PowerBLAST programs (Altschul et al., J. Mol. Biol., 1990, 215, 403-410; Zhang and Madden, Genome Res., 1997, 7, 649-656) or by using the Gap program (Wisconsin Sequence Analysis Package, Version 8 for Unix, Genetics Computer Group, University Research Park, Madison Wis.), using default settings, which uses the algorithm of Smith and Waterman (Adv. Appl. Math., 1981, 2, 482-489).

A "target nucleic acid" or "target segment" as used herein is a polynucleotide (e.g., RNA, DNA) that includes a "target site" or "target sequence." The terms "target site" or "target sequence" are used interchangeably herein to refer to a nucleic acid sequence present in a target nucleic acid to which a targeting segment of a guide RNA will bind, provided sufficient conditions for binding to exist; and/or to which a region (segment) of a PAM-containing oligonucleotide (e.g., a specificity segment and/or an orientation segment) will bind. For example, the target site (or target sequence) 5'-GAGCAUAUC-3' within a target nucleic acid is targeted by (or is bound by, or hybridizes with, or is complementary to) the sequence 5'-GAUAUGCUC-3'. Suitable hybridization conditions include physiological conditions normally present in a cell. For a double stranded target nucleic acid, the strand of the target nucleic acid that is complementary to and hybridizes with the guide RNA is referred to as the "complementary strand"; while the strand of the target nucleic acid that is complementary to the "complementary strand" (and is therefore not complementary to the guide RNA) is referred to as the "noncomplementary strand" or "non-complementary strand". In cases where the target nucleic acid is a single stranded target nucleic acid (e.g., single stranded DNA (ssDNA), single stranded RNA (ssRNA)), the guide RNA is complementary to and hybridizes with single stranded target nucleic acid.

By "cleavage" in the context of nucleic acid cleavage it is meant the breakage of the covalent backbone of a target nucleic acid molecule (e.g., RNA, DNA). Cleavage can be initiated by a variety of methods including, but not limited to, enzymatic or chemical hydrolysis of a phosphodiester bond. Both single-stranded cleavage and double-stranded cleavage are possible, and double-stranded cleavage can occur as a result of two distinct single-stranded cleavage events. In certain embodiments, a complex comprising a guide RNA and a Class 2 CRISPR effector protein is used for targeted cleavage of a single stranded target nucleic acid (e.g., ssRNA, ssDNA).

"Nuclease" and "endonuclease" are used interchangeably herein to mean an enzyme which possesses catalytic activity for nucleic acid cleavage (e.g., ribonuclease activity (ribonucleic acid cleavage), deoxyribonuclease activity (deoxyribonucleic acid cleavage), etc.).

By "cleavage domain" or "active domain" or "nuclease domain" of a nuclease it is meant the polypeptide sequence or domain within the nuclease which possesses the catalytic activity for nucleic acid cleavage. A cleavage domain can be contained in a single polypeptide chain or cleavage activity can result from the association of two (or more) polypeptides. A single nuclease domain may consist of more than one isolated stretch of amino acids within a given polypeptide.

A nucleic acid molecule that binds to the Class 2 CRISPR effector protein and targets the protein to a specific location within the target nucleic acid is referred to herein as a "guide RNA". A guide RNA comprises two segments, a first segment (referred to herein as a "targeting segment"); and a second segment (referred to herein as a "protein-binding segment"). By "segment" it is meant a segment/section/region of a molecule, e.g., a contiguous stretch of nucleotides in a nucleic acid molecule. A segment can also mean a region/section of a complex such that a segment may comprise regions of more than one molecule. For example, in some cases the guide RNA is one nucleic acid molecule (e.g., one RNA molecule) and the protein-binding segment therefore comprises a region of that one molecule. In other cases, the protein-binding segment (described below) of a guide RNA includes regions of two separate molecules that are hybridized along a region of complementarity (forming a dsRNA duplex). The definition of "segment," unless otherwise specifically defined in a particular context, is not limited to a specific number of total base pairs, is not limited to any particular number of base pairs from a given nucleic acid molecule, is not limited to a particular number of separate molecules within a complex, and may include regions of nucleic acid molecules that are of any total length and may or may not include regions with complementarity to other molecules.

In some embodiments, a subject nucleic acid (e.g., a guide RNA, a nucleic acid comprising a nucleotide sequence encoding a guide RNA; a nucleic acid encoding a Class 2 CRIPSR effector protein; a PAM-containing oligonucleotide, etc.) comprises a modification or sequence (e.g., an additional segment at the 5' and/or 3' end) that provides for an additional desirable feature (e.g., modified or regulated stability; subcellular targeting; tracking, e.g., a fluorescent label; a binding site for a protein or protein complex; etc.). Non-limiting examples include: a 5' cap (e.g., a 7-methylguanylate cap (m7G)); a 3' polyadenylated tail (i.e., a 3' poly(A) tail); a ribozyme sequence (e.g. to allow for self-cleavage and release of a mature molecule in a regulated fashion); a riboswitch sequence (e.g., to allow for regulated stability and/or regulated accessibility by proteins and/or protein complexes); a stability control sequence; a sequence that forms a dsRNA duplex (i.e., a hairpin)); a modification or sequence that targets the nucleic acid to a subcellular location (e.g., nucleus, mitochondria, chloroplasts, and the like); a modification or sequence that provides for tracking (e.g., direct conjugation to a fluorescent molecule, conjugation to a moiety that facilitates fluorescent detection, a sequence that allows for fluorescent detection, etc.); a modification or sequence that provides a binding site for proteins (e.g., proteins that act on DNA and/or RNA, including transcriptional activators, transcriptional repressors, DNA methyltransferases, DNA demethylases, histone acetyltransferases, histone deacetylases, and the like); and combinations thereof.

A guide RNA and a Class 2 CRISPR effector protein form a complex (i.e., bind via non-covalent interactions). The guide RNA provides target specificity to the complex by comprising a nucleotide sequence that is complementary to a sequence of a target nucleic acid. The protein of the complex provides the site-specific activity. In other words, the protein is guided to a target nucleic acid sequence (e.g. a target sequence in a chromosomal nucleic acid; a target sequence in an extrachromosomal nucleic acid, e.g. an episomal nucleic acid, a minicircle, an ssRNA, an ssDNA, etc.; a target sequence in a mitochondrial nucleic acid; a target sequence in a chloroplast nucleic acid; a target sequence in a plasmid; etc.) by virtue of its association with the protein-binding segment of the guide RNA.

In some embodiments, a guide RNA comprises two separate nucleic acid molecules: an "activator" and a "targeter" and is referred to herein as a "dual guide RNA", a "double-molecule guide RNA", a "dual guide RNA", a "two-molecule guide RNA", or simply "dgRNA." In some embodiments, the guide RNA has an activator and a targeter (as are present in a dual guide RNA), where the activator and targeter are covalently linked to one another (e.g., via intervening nucleotides) and is referred to herein as a "single guide RNA", a "single-molecule guide RNA," or a "one-molecule guide RNA." The term "guide RNA" is inclusive, referring to both dual guide RNAs (dgRNAs) and to single guide RNAs (sgRNAs). In some cases, a guide RNA is a DNA/RNA hybrid molecule.

As used herein, the terms "Complement Component is protease," "C1s," and "Calcium Dependent Serine Proteinase," refer to the same protease having the amino acid sequence set forth in NCBI reference sequence XP_007645011.1 and Uniprot G3GUR0. This protease is expressed by CHO cells, such as, CHO-K1 cell line.

As used herein, the term "derived" in the context of a polypeptide refers to a polypeptide that has a sequence that is based on that of a protein from a particular source (e.g., HIV). A polypeptide derived from a protein from a particular source may be a variant of the protein from the particular source. For example, a polypeptide derived from a protein from a particular source may have a sequence that is modified with respect to the protein's sequence from which it is derived. A polypeptide derived from a protein from a particular source may have the endogenous signal sequence replaced with a heterologous signal sequence. A polypeptide derived from a protein from a particular source shares at least 30% sequence identity with, at least 40% sequence identity with, at least 50% sequence identity with, at least 60% sequence identity with, at least 70% sequence identity with, at least 80% sequence identity with, or at least 90% sequence identity with the protein from which it is derived.

As used herein, the term "gp120" refers to a polypeptide derived from a HIV envelope glycoprotein gp120, e.g. from clade B strain. gp120 can be a full length gp120 or a modified version of a full length gp120, e.g., gp120 may have the endogenous signal sequence replaced with a heterologous signal sequence and may optionally include a purification tag.

Before describing the present invention in detail, it is to be understood that this invention is not limited to particular formulations or process parameters as such may, of course, vary. It is also to be understood that the terminology used herein is for the purpose of describing particular embodiments of the invention only and is not intended to be limiting.

Although a number of methods and materials similar or equivalent to those described herein can be used in the practice of the present invention, the preferred materials and methods are described herein.

DETAILED DESCRIPTION

C1s-deficient cell lines and methods for use of same for producing exogenous polypeptides, e.g., human immunodeficiency virus (HIV) envelope glycoprotein polypeptides, such as, gp120 are provided. The HIV envelope glycoproteins produced by the cell lines and methods provided herein are suitable for eliciting antibodies effective in prevention and/or treatment of HIV infection. In certain cases, the antibodies elicited by the HIV envelope glycoproteins produced by the cell lines disclosed herein are broadly neutralizing antibodies.

Cell Lines

Provided herein are genetically modified calcium-dependent serine (C1s) protease-deficient mammalian cell lines. The C1s protease-deficient cell lines comprising a mutation of an endogenous C1s gene encoding the C1s protease, where the mutation significantly decreases protease activity of the C1s protease. In certain embodiments, the genetically modified mammalian cell line has been genetically modified to include a targeted mutation in the endogenous c1s gene. In certain embodiments, the targeted mutation includes a deletion of a region of the endogenous c1s gene. In certain embodiments, the targeted mutation includes an insertion in the endogenous c1s gene.

In certain embodiments, the genetically modified mammalian cell line has been genetically modified to delete at least one base in the endogenous c1s gene, e.g., at least two, at least three, at least four, at least five, at least six bases. In certain embodiments, the genetically modified mammalian cell line has been genetically modified to delete 1-10 bases in the endogenous c1s gene, such as, deletion of 2 to 8 bases, or 4-6 bases resulting in at least a 50% reduction in C1s protease-mediated protease activity of the cell line.

The C1s deficient cells lines may include a C1s encoding gene sequence that has been completely or partially inactivated. In certain embodiments, two copies of the c1s gene have been inactivated. In some embodiments, three or more copies of c1s gene have been inactivated. Inactivation of c1s gene may be due to deletion of a part or entire sequence of the of c1s gene and/or due to insertion of at least one nucleotide. The inactivation may result in reduced expression or reduced activity of the C1s protease encoded by the c1s gene. In some embodiments, the inactivation may result in lack of expression of the C1s protease. In some examples, the inactivation of c1s gene results in expression of a truncated or otherwise mutated C1s that lacks detectable activity. In some cases, the inactivation of c1s gene results in a decrease of the enzymatic activity of the C1s protease by at least 50%, such as, e.g., by 50%-95%, 50%-90%, 50%-85%, 50%-80%, 50%-75%, 50%-70%. In some cases, expression levels of the C1s protease in a C1s deficient cell lines is decreased by at least 50% such as, e.g., by 50%-95%, 50%-90%, 50%-85%, 50%-80%, 50%-75%, 50%-70%. In some cases, the C1s deficient cells line expresses an uncleaved exogenous polypeptide at a level that is at least 50% higher than the level of the uncleaved exogenous polypeptide expressed by the unmodified parental cell line from which the C1s deficient cell line is derived.

In certain aspects, the C1s deficient cell lines may include an insertion or a deletion in the c1s gene resulting in a frame shift mutation and a premature stop codon. In certain aspects, the premature stop codon may result in production of a truncated C1s polypeptide that has no detectable enzymatic activity. In certain aspects, the truncated C1s protease may be an N-terminal fragment of full length C1s protease and may be 10-694 amino acids or 20-500 amino acids, such as, 200, 303 or 400 amino acids long. In certain embodiments, the C1s deficient cell line may include a c1s gene in which nucleotides have been deleted. The deletion may be in the region targeted by a guide RNA of a CRISPR/Cas9 system. The deletion may result in a C1s polypeptide having a deletion of 1-10 amino acids, such as, deletion of 2 to 8 amino acids, 4-6 amino acids, such as, 3 or 5 amino acids, resulting in a C1s polypeptide with reduced activity.

In certain cases, the parental cell line from which the cell lines provided herein are derived may include a cis gene that is transcribed into an mRNA having the sequence set forth in SEQ ID NO:4 (NCBI Acc. No. XM_007646821) and encodes a C1s protease having the amino acid sequence set forth in SEQ ID NO:6 (NCBI Acc. No. XP_007645011.1):

(SEQ ID NO: 4)

atgggcaaatcaccagaggcatggtgcattgtcttgttttctgttttggca
tcattttctgccgagcctaccatgcatggggagatcctgtcccctaactat
cctcaggcgtaccccaatgagatcgagaaaacgtgggacatagaagtccca
gaagggtttgggattcgcctctacttcacccatctggacatggagctgtca
gagaactgcgaatatgactcggtgcagataatctcaggaggcgtcgaggaa
gggagactctgtgggcagaggaccagcaagaatgccaactcccccattgtg
gaagagtttcaaatgccatacaataaactccaggtgatctttaggtcagac
ttctccaacgaagagcggtttactggctttgctgcatattacgctgccgta
gatataaatgaatgcacagattttacagatgtcccttgcagccacttctgc
aataatttcattggtggttacttctgctcctgtcccccagaatacttcctc
cacgatgacatgaggaactgcggagtcaattgtagtgggaatgtattcact
gccctgattggggagatttcaagccccaattatcccagtccataccccgag
aactcaaggtgtgaataccagattttgctggaggaggggttccaagtggtg
gtgactatccggagagaagattttgatgtggaaccagctgactcggagggg
aactgccaggacagtttactcttgctgcaaaaaatcaactatttggtcctt
actgtggcaatgggttccctgggccactaactattgaaacccacagtaaca
ctcttgacattgtctttcaaacggacctaacagagcaaagaaaaggctgga
agcttcgttaccatggagacccaatcccttgtcccaaggaaatcactgcca
attctgtttgggtgcctgaaaaggcaaaatatgtgtttaaagatgtggtga
agatatcctgtgtggacggatttgaagttgtagagggaaatgttggctcag
cattcttctattctacttgtcaaagcaatggacagtggagtaattccagac
tacaatgtcagcctgtggactgtggtattccggaacccattcagaatggta
aagttgacgatccagaaaacactgtgtttggctctgtcatccagtactcgt
gcgaggagccatattactacatggaacatgaagaacacggcggggagtatc
gctgcgctgctaatgggagctgggtgaatgacgaactgggcatagagctcc
caaaatgtgttccagtctgtggggtacccactgagcccattgcattacagc
agaggatatttggaggattccctgcaaagatccagagttttccttggcaag
tcttctttgagtccccacgggccggtggggctcttattgacgagtactggg
tgttgacagccgctcatgttgtggagggaaactctgacccatctatgtatg
tggggaccacatttgtgagaatggaacatctggcgaatgcccagaggctca
ccgctgaacgtgtgattattcatccaggctggaagccagcggatgacctag
aaacacggacaaattttgacaatgacattgcactggtgcagctgaaagacc
ccgtgaaaatggggcccactgtctcccccatctgcctgccaggtacctcct
cagagtacaacccctcaaagaatgacctgggactgatctcaggtggggcc -continued gaacagagaagagaaatattgttccccaactcaaaggggcaaagttacctg
tgacctctttagagaagtgccaacaggtgaaaggggagaactccaaagtga
gggcggatgactacgttttcaccagcaacatgatctgtgctggagagaaag
gtgttgatagctgtcaggggacagtggtggggcttttgctttgcaggtcc
ccaatgtaaaggaccccaaattctatgtggcaggcctagtgtcctgggga
aaaagtgtgggacctatggaatctacacaaaggtaaagaactacatggatt
ggatcgtgaagacgatgcaggagaatagtgtccccagtaaggactaa (SEQ ID NO: 6)

MGKSPEAWCIVLFSVLASFSAEPTMHGEILSPNYPQAYPNEIEKTWDIEVP
EGFGIRLYFTHLDMELSENCEYDSVQIISGGVEEGRLCGQRTSKNANSPIV
EEFQMPYNKLQVIFRSDFSNEERFTGFAAYYAAVDINECTDFTDVPCSHFC
NNFIGGYFCSCPPEYFLHDDMRNCGVNCSGNVFTALIGEISSPNYPSPYPE
NSRCEYQILLEEGFQVVVTIRREDFDVEPADSEGNCQDSLLFAAKNQLFGP
YCGNGFPGPLTIETHSNTLDIVFQTDLTEQRKGWKLRYHGDPIPCPKEITA
NSVWVPEKAKYVFKDVVKISCVDGFEVVEGNVGSAFFYSTCQSNGQWSNSR
LQCQPVDCGIPEPIQNGKVDDPENTVFGSVIQYSCEEPYYYMEHEEHGGEY
RCAANGSWVNDELGIELPKCVPVCGVPTEPIALQQRIFGGFPAKIQSFPWQ
VFFESPRAGGALIDEYWVLTAAHVVEGNSDPSMYVGTTFVRMEHLANAQRL
TAERVIIHPGWKPADDLETRTNFDNDIALVQLKDPVKMGPTVSPICLPGTS
SEYNPSKNDLGLISGWGRTEKRNIVPQLKGAKLPVTSLEKCQQVKGENSKV
RADDYVFTSNMICAGEKGVDSCQGDSGGAFALQVPNVKDPKFYVAGLVSWG
KKCGTYGIYTKVKNYMDWIVKTMQENSVPSKD

In some embodiments, deletion of a region of the endogenous c1s gene may be carried out by using targeted CRISPR/Cas9 mediated gene editing. The nucleotide sequence targeted by a guide RNA of a CRISPR/Cas9 may be the nucleotide sequence corresponding to positions 1431-1453 in SEQ ID NO:4 (shown in bold above).

In some cases, the cell line may have a c1s gene with a deletion of four nucleotides that correspond to positions 1448-1451 of the c1s mRNA of SEQ ID NO:4. In some cases, the genetically modified mammalian cell line having a c1s gene with a deletion of nucleotides that correspond to positions 1448-1451 of SEQ ID NO:4 may express an mRNA having the sequence set forth in SEQ ID NO: 8. The C1s polypeptide expressed by this cell line may have the amino acid sequence set forth in SEQ ID NO:11.

c1s mRNA_4 bp deletion; (SEQ ID NO:8):

atgggcaaatcaccagaggcatggtgcattgtcttgttttctgttttggca
tcattttctgccgagcctaccatgcatggggagatcctgtcccctaactat
cctcaggcgtaccccaatgagatcgagaaaacgtgggacatagaagtccca
gaagggtttgggattcgcctctacttcacccatctggacatggagctgtca
gagaactgcgaatatgactcggtgcagataatctcaggaggcgtcgaggaa
gggagactctgtgggcagaggaccagcaagaatgccaactcccccattgtg
gaagagtttcaaatgccatacaataaactccaggtgatctttaggtcagac
ttctccaacgaagagcggtttactggctttgctgcatattacgctgccgta -continued gatataaatgaatgcacagattttacagatgtcccttgcagccacttctgc aataatttcattggtggttacttctgctcctgtcccccagaatacttcctc cacgatgacatgaggaactgcggagtcaattgtagtgggaatgtattcact gccctgattggggagatttcaagccccaattatcccagtccataccccgag aactcaaggtgtgaataccagattttgctggaggaggggttccaagtggtg gtgactatccggagagaagattttgatgtggaaccagctgactcggagggg aactgccaggacagtttactctttgctgcaaaaaatcaactatttggtcct tactgtggcaatgggttccctgggccactaactattgaaacccacagtaac actcttgacattgtctttcaaacggacctaacagagcaaagaaaaggctgg aagcttcgttaccatggagacccaatcccttgtcccaaggaaatcactgcc aattctgtttgggtgcctgaaaaggcaaaatatgtgtttaaagatgtggtg aagatatcctgtgtggacggatttgaagttgtagagggaaatgttggctca gcattcttctattctacttgtcaaagcaatggacagtggagtaattccaga ctacaatgtcagcctgtggactgtggtattccggaacccattcagaatggt aaagttgacgatccagaaaacactgtgtttggctctgtcatccagtactcg tgcgaggagccatattactacatggaacatgaagaacacggcggggagtat cgctgcgctgctaatgggagctgggtgaatgacgaactgggcatagagctc ccaaaatgtgttccagtctgtggggtacccactgagcccattgcattacag cagaggatatttggaggattccctgcaaagatccagagttttccttggcaa gtcttctttgagtccccacgggccggtggggctcttattgacgagtactgg gtgttgacagccgctcatgggagggaaactctgacccatctatgtatgtgg ggaccacatttgtgagaatggaacatctggcgaatgcccagaggctcaccg ctgaacgtgtgattattcatccaggctggaagccagcggatgacctagaaa cacggacaaattttgacaatgacattgcactggtgcagctgaaagaccccg tgaaaatggggcccactgtctcccccatctgcctgccaggtacctcctcag agtacaacccctcaaagaatgacctgggactgatctcagggtggggccgaa cagagaagagaaatattgttccccaactcaaaggggcaaagttacctgtga cctctttagagaagtgccaacaggtgaaaggggagaactccaaagtgaggg cggatgactacgttttcaccagcaacatgatctgtgctggagagaaaggtg ttgatagctgtcaggggggacagtggtggggcttttgctttgcaggtcccca atgtaaaggacccccaaattctatgtggcaggcctagtgtcctggggggaaaa agtgtgggacctatggaatctacacaaaggtaaagaactacatggattgga tcgtgaagacgatgcaggagaatagtgtccccagtaaggactaa Calcium-dependent serine protease (C1s), truncated protein (translated from the mRNA having the 4 bp "ttgt" deletion); (SEQ ID NO:11):

(SEQ ID NO: 11)

MGKSPEAWCIVLFSVLASFSAEPTMHGEILSPNYPQAYPNEIEKTWDIEVP

EGFGIRLYFTHLDMELSENCEYDSVQIISGGVEEGRLCGQRTSKNANSPIV

EEFQMPYNKLQVIFRSDFSNEERFTGFAAYYAAVDINECTDFTDVPCSHFC

NNFIGGYFCSCPPEYFLHDDMRNCGVNCSGNVFTALIGEISSPNYPSPYPE

NSRCEYQILLEEGFQVVVTIRREDFDVEPADSEGNCQDSLLFAAKNQLFGP

YCGNGFPGPLTIETHSNTLDIVFQTDLTEQRKGWKLRYHGDPIPCPKEITA

NSVWVPEKAKYVFKDVVKISCVDGFEVVEGNVGSAFFYSTCQSNGQWSNSR

LQCQPVDCGIPEPIQNGKVDDPENTVFGSVIQYSCEEPYYYMEHEEHGGEY

RCAANGSWVNDELGIELPKCVPVCGVPTEPIALQQRIFGGFPAKIQSFPWQ

VFFESPRAGGALIDEYWVLTAAHGRETLTHLCMWGPHL

In some cases, the cell line may have a cis gene with a deletion of three non-consecutive nucleotides corresponding to positions 1444 ("c"), 1445 ("a"), and 1447 (g") of the c1s mRNA of SEQ ID NO:4. In some cases, the genetically modified mammalian cell line having a cis gene with a deletion of nucleotides that correspond to positions 1444, 1445, and 1447 of SEQ ID NO:4 may express an mRNA having the sequence set forth in SEQ ID NO: 14. The C1s polypeptide expressed by this cell line may have the amino acid sequence set forth in SEQ ID NO:16.

C1s mRNA_3 bp deletion; (SEQ ID NO:14):

(SEQ ID NO: 14)

atgggcaaatcaccagaggcatggtgcattgtcttgttttctgttttggca tcatttttctgccgagcctaccatgcatggggagatcctgtcccctaactat cctcaggcgtaccccaatgagatcgagaaaacgtgggacatagaagtccca gaagggtttgggattcgcctctacttcacccatctggacatggagctgtca gagaactgcgaatatgactcggtgcagataatctcaggaggcgtcgaggaa gggagactctgtgggcagaggaccagcaagaatgccaactcccccattgtg gaagagtttcaaatgccatacaataaactccaggtgatctttaggtcagac ttctccaacgaagagcggtttactggctttgctgcatattacgctgccgta gatataaatgaatgcacagattttacagatgtcccttgcagccacttctgc aataatttcattggtggttacttctgctcctgtcccccagaatacttcctc cacgatgacatgaggaactgcggagtcaattgtagtgggaatgtattcact gccctgattggggagatttcaagccccaattatcccagtccataccccgag aactcaaggtgtgaataccagattttgctggaggaggggttccaagtggtg gtgactatccggagagaagattttgatgtggaaccagctgactcggagggg aactgccaggacagtttactctttgctgcaaaaaatcaactatttggtcct tactgtggcaatgggttccctgggccactaactattgaaacccacagtaac actcttgacattgtctttcaaacggacctaacagagcaaagaaaaggctgg aagcttcgttaccatggagacccaatcccttgtcccaaggaaatcactgcc aattctgtttgggtgcctgaaaaggcaaaatatgtgtttaaagatgtggtg aagatatcctgtgtggacggatttgaagttgtagagggaaatgttggctca gcattcttctattctacttgtcaaagcaatggacagtggagtaattccaga ctacaatgtcagcctgtggactgtggtattccggaacccattcagaatggt aaagttgacgatccagaaaacactgtgtttggctctgtcatccagtactcg tgcgaggagccatattactacatggaacatgaagaacacggcggggagtat cgctgcgctgctaatgggagctgggtgaatgacgaactgggcatagagctc ccaaaatgtgttccagtctgtggggtacccactgagcccattgcattacag -continued

```
cagaggatatttggaggattccctgcaaagatccagagttttccttggcaa

gtcttctttgagtccccacgggccggtggggctcttattgacgagtactgg

gtgttgacagccgcttttgtggagggaaactctgacccatctatgtatgtg

gggaccacatttgtgagaatggaacatctggcgaatgcccagaggctcacc

gctgaacgtgtgattattcatccaggctggaagccagcggatgacctagaa

acacggacaaatttgacaatgacattgcactggtgcagctgaaagacccc

gtgaaaatggggcccactgtctcccccatctgcctgccaggtacctcctca

gagtacaacccctcaaagaatgacctgggactgatctcagggtggggccga

acagagaagagaaatattgttccccaactcaaaggggcaaagttacctgtg

acctctttagagaagtgccaacaggtgaaaggggagaactccaaagtgagg

gcggatgactacgttttcaccagcaacatgatctgtgctggagagaaaggt

gttgatagctgtcagggggacagtggtggggcttttgctttgcaggtcccc

aatgtaaaggaccccaaattctatgtggcaggcctagtgtcctgggggaaa

aagtgtgggacctatggaatctacacaaaggtaaagaactacatggattgg

atcgtgaagacgatgcaggagaatagtgtccccagtaaggactaa
```

Calcium-dependent serine protease (C1s), truncated protein (from 3 bp deletion mRNA; (SEQ ID NO:16):

```
                                          (SEQ ID NO: 16)
MGKSPEAWCIVLFSVLASFSAEPTMHGEILSPNYPQAYPNEIEKTWDIEVP

EGFGIRLYFTHLDMELSENCEYDSVQIISGGVEEGRLCGQRTSKNANSPIV

EEFQMPYNKLQVIFRSDFSNEERFTGFAAYYAAVDINECTDFTDVPCSHFC

NNFIGGYFCSCPPEYFLHDDMRNCGVNCSGNVFTALIGEISSPNYPSPYPE

NSRCEYQILLEEGFQVVVTIRREDFDVEPADSEGNCQDSLLFAAKNQLFGP

YCGNGFPGPLTIETHSNTLDIVFQTDLTEQRKGWKLRYHGDPIPCPKEITA

NSVWVPEKAKYVFKDVVKISCVDGFEVVEGNVGSAFFYSTCQSNGQWSNSR

LQCQPVDCGIPEPIQNGKVDDPENTVFGSVIQYSCEEPYYYMEHEEHGGEY

RCAANGSWVNDELGIELPKCVPVCGVPTEPIALQQRIFGGFPAKIQSFPWQ

VFFESPRAGGALIDEYWVLTAAFVEGNSDPSMYVGTTFVRMEHLANAQRLT

AERVIIHPGWKPADDLETRTNFDNDIALVQLKDPVKMGPTVSPICLPGTSS

EYNPSKNDLGLISGWGRTEKRNIVPQLKGAKLPVTSLEKCQQVKGENSKVR

ADDYVFTSNMICAGEKGVDSCQGDSGGAFALQVPNVKDPKFYVAGLVSWGK

KCGTYGIYTKVKNYMDWIVKTMQENSVPSKD
```

In certain aspects, the C1s-deficient cell line, e.g., CHO cell line, has one allele of C1s gene with the 4 basepair deletion and the second allele with the 3 basepair deletion.

In certain embodiments, the C1s-deficient cell line produces an exogenous HIV protein, e.g., an Env proteins, e.g., a gp120 polypeptide. In certain embodiments, the CRISPR/Cas9 mediated deletion of cis gene prevents cleavage of exogenous proteins expressed by the C1s-deficient cells, for example, of exogenous proteins that have a cleavage site for C1s protease, e.g., of gp120 polypeptides that have a cleavage site for C1s. In certain aspects, the cell lines disclosed herein may be used to express a gp120 polypeptide that includes a V3 domain having a serine protease cleavage site GPGRAF. In CHO cells expressing an active C1s protease, the gp120 is cleaved after the R in the amino acid sequence GPGRAF in the V3 domain. The cell lines disclosed herein do not express an active form of the C1s protease and hence the gp120 is not cleaved by the C1s protease. In some cases, the percentage of cleaved exogenous polypeptide (e.g., gp120 polypeptide) produced by the C1s-deficient cell compared to unmodified parental cell is reduced by at least 50% such as, e.g., by 50%-99%, 50%-98%, 50%-95%, 50%-90%, 50%-80%, or 50%-70% or by at least 60%, 70%, 80%, 90%, 95%, 97%, or 99%. In certain embodiments, fully intact gp120 may be expressed.

The cell lines provided herein may be used to express any exogenous polypeptide that has a cleavage site for C1s protease. In certain aspects, the cell lines provided herein may be used to express human Factor VIII in an uncleaved form. In certain aspects, the cell lines provided herein may be used to express human IFN-γ in an uncleaved form.

In certain embodiments, the C1s protease-deficient cells are derived from a CHO cell line that lacks or has limited expression of or function of the endogenous gene encoding mannosyl (alpha-1,3)-glycoprotein beta-1,2-N-Acetylglucosaminyltransferase (Mgat1). Mgat1 is also referred to as N-Glycosyl-Oligosaccharide-Glycoprotein N-Acetylglucosaminyltransferase I, Alpha-1,3-Mannosyl-Glycoprotein 2-Beta-N-Acetylglucosaminyltransferase, GlcNAc-T I, GLYT1, GLCT1, GNT-1, GLCNAC-TI, and Gnt1. Deletion of Mgat1 prevents glycosylation from advancing beyond the $Man_5GlcNAc_2$ state in the modified cell lines disclosed herein. In certain embodiments, the CHO cell line has been genetically modified to delete the endogenous mgat1 gene. In such embodiments, the deletion of the endogenous mgat1 gene may be carried out by using CRISPER/Cas9 mediated gene editing. In certain embodiments, the CRISPER/Cas9 mediated deletion of mgat1 gene prevents Mgat1-mediated addition of a N-acetylglucosamine moiety to a terminal mannose residue present at the N-linked glycosylation site of the HIV envelope glycoprotein polypeptide produced in the cell line, resulting in expression of the HIV envelope glycoprotein polypeptide with one or more terminal mannose, e.g., mannose-5, mannose-8, or mannose-9. In certain embodiments, the Mgat1 deficient cell lines may include a Mgat1 encoding gene sequence that has been completely or partially inactivated. In certain embodiments, two copies of the mgat1 gene has been inactivated. In some embodiments, three or more copies of mgat1 gene has been inactivated. Inactivation of mgat1 gene may be due to deletion of a part or entire sequence of the of mgat1 gene and/or due to insertion of at least one nucleotide. The inactivation may result in reduced expression or reduced activity of Mgat1. In some embodiments, the inactivation may result in lack of expression of Mgat1. In some examples, the inactivation of mgat1 gene results in expression of a truncated or otherwise mutated Mgat1 that lacks detectable activity. In certain aspects, the glycosylation heterogeneity of the polypeptides produced by cell lines provided herein is markedly reduced such that a majority of the polypeptides have one or more terminal mannose, mannose-5, mannose-8, or mannose-9 glycans. In certain embodiments, the genetic modification to delete the endogenous mgat1 gene results in at least 75% of the HIV envelope glycoprotein polypeptides produced by the genetically modified cell line having terminal mannose glycans at the N-linked glycosylation site. In certain cases, at least 75% or more, such as, 75%-95%, 75%-96%, 75%-97%, 75%-98%, 80%-98%, 85%-99%, e.g., 80%, 85%, 90%, 95%, 98%, 99%, or more of the HIV envelope glycoprotein polypeptides produced by the genetically modified cell line have terminal mannose glycans at the N-linked glycosylation site. As used herein, the term "terminal mannose" or "terminal mannose glycans" refers to N-glycans having one or more mannose residues at the terminus of the N-glycan. This term encompasses, N-glycans having 5, 8, or 9 terminal mannose residues.

The CHO cell line from which the cell lines disclosed herein are derived may be a CHO cell line adapted for growth in suspension culture, adherent culture, or both. In certain aspects, the genetically modified CHO cell line may be derived from a parent CHO cell line, such as, CHO S, CHO K1, CHO-DXB11 (also known as CHO-DUKX), CHO-PRO3, CHO-PRO5, or CHO-DG44 cell line, and the like. In certain aspects, the genetically modified CHO cell line may be derived from a parent CHO cell line, such as, CHO K1 cell line (ATCC® CCL-61™).

In certain aspects, the genetically modified CHO cell line is not deficient in markers commonly used for selection of transfected CHO cells, such as, glutamine synthetase (GS), dihydrofolate reductase (DHFR), and the like. In certain aspects, the genetically modified CHO cell line is derived from a parental CHO cell line that includes a gene encoding GS, DHFR, or both. As such, in certain examples, the generation of the genetically modified CHO cell line does not require transfection of a nucleic acid encoding GS and/or DHFR. In certain aspects, the genetically modified CHO cell line is derived from a parental CHO S or CHO K1 cell line that includes a gene encoding GS, DHFR, or both. In certain aspects, the parental cell line is CHO S that expresses GS. In other embodiments, the parental cell line is CHO K1 that expresses GS. In certain embodiments, the genetically modified CHO cell line of the present disclosure is not derived from CHO Lec1 cells. In certain embodiments, the genetically modified CHO cell line of the present disclosure does not produce Mgat1 or fragments thereof. In certain embodiments, the Mgat1 encoding gene has been deleted from the cell lines disclosed herein such that the cell line has no detectable Mgat1 activity. In certain embodiments, the Mgat1 encoding gene has been disrupted from the cell lines disclosed herein such that the cell line has no detectable Mgat1 activity. In other aspects, the cell line may also be deficient in GS and/or DHFR.

In certain aspects, the cell lines provided herein produce the exogenous polypeptide at a concentration of at least 50 milligrams/Liter (mg/L), such as, at least 75 mg/L, 100 mg/L, 150 mg/L, 175 mg/L, 200 mg/L, 250 mg/L, 300 mg/L, e.g., 50-300 mg/L, 50-250 mg/L, or 50-200 mg/L. The cell line may express the exogenous polypeptide at a concentration of at least 50 mg/L after 1-30 days of culturing, e.g., 1 day, 2, days, 3 days, 5 days, 7 days, 10 days, 15 days, 20 days, or more.

A subject genetically modified host cell is generated using standard methods well known to those skilled in the art. In some cases, the nucleic acid encoding Mgat1 is disrupted (e.g., deleted) using a CRISPR/Cas9 system comprising: i) an RNA-guided endonuclease; and ii) a guide RNA (e.g., a single molecule guide RNA; or a double-molecule guide RNA) that provides for deletion of endogenous Mgat1 gene; and iii) a donor DNA template. Suitable RNA-guided endonucleases include an RNA-guided endonuclease comprising an amino acid sequence having at least 85%, at least 90%, at least 95%, at least 98%, at least 99%, or 100%, amino acid sequence identity to the amino acid sequence of *Streptococcus pyogenes* Cas9 (GenBank Accession No.: AKP81606.1) or *Staphylococcus aureus* Cas9 (NCBI Reference Sequence: WP_001573634.1). The guide RNA comprises a targeting sequence. A suitable targeting sequence can be determined by those skilled in the art. The donor template comprises a nucleotide sequence complementary to Mgat1-encoding nucleotide sequence.

In certain aspects, a genetically modified Chinese hamster ovary (CHO) cell line comprising a targeted mutation of gene encoding mannosyl (alpha-1,3)-glycoprotein beta-1,2-N-Acetylglucosaminyltransferase (Mgat1) and expressing gp120 glycoprotein, wherein the genetically modified cell line is deposited with American Type Culture Collection (ATCC) as PTA-124141; or PTA-124142 is used to produce C1s-deficient cells.

Compositions and Methods for Producing Exogenous Polypeptide

The present disclosure provides a composition comprising: a) a genetically modified host cell line as described above or elsewhere herein; and b) a culture medium.

The present disclosure provides a method of producing a polypeptide of interest. The method may include culturing the composition for a time period and under conditions suitable for production of the exogenous polypeptide, where the composition comprises: a) a genetically modified host cell line of the present disclosure; and b) a culture medium; and separating the genetically modified host cell line from the culture medium, to generate a cell culture comprising secreted polypeptide of interest. Separating the genetically modified host cells from the culture medium can be accomplished by methods known in the art, such as centrifugation, filtration, and the like.

The exogenous polypeptide secreted into the culture medium may be purified using any standard process. For example, the exogenous polypeptide, such as, an envelope glycoprotein, e.g., gp140 trimer, secreted into the culture medium may be purified using the process disclosed in Sanders R W, Moore J P. Immunological reviews. 2017 Jan. 1; 275(1):161-82; Sanders R W, et al., PLoS pathogens. 2013 Sep. 19; 9(9):e1003618; Sharma S K, et al., Cell reports. 2015 Apr. 28; 11(4):539-50; or Karlsson Hedestam G B, et al., Immunological reviews. 2017 Jan. 1; 275(1): 183-202.

In certain embodiments, production of exogenous polypeptides using the cell lines provided herein does not require culturing in the presence of inhibitors that prevent glycosylation from proceeding beyond $Man_5GlcNAc_2$ state. As such, the culture medium for culturing the cell lines for expressing an exogenous polypeptide does not include inhibitors such as kifunensine.

Exogenous Polypeptide

Any exogenous polypeptide of interest can be produced using the cell lines described herein. In some embodiments, the exogenous polypeptide may be a polypeptide that can be used to elicit an immune response in a mammal. In certain embodiments, the immune response may result in prevention or treatment of HIV infection.

In certain embodiments, the exogenous polypeptide is a polypeptide that undergoes glycosylation when expressed in a eukaryotic host cell. In certain embodiments, the exogenous polypeptide includes a N-linked glycosylation site comprising the consensus sequence Asn-X-Ser/Thr, where X is any amino acid except proline (Pro). In certain embodiments, expressing the exogenous polypeptide in the cell lines provided herein prevents glycosylation from advancing beyond the $Man_5GlcNAc_2$ state.

In certain embodiments, the exogenous polypeptide is derived from HIV and may be a HIV-1 envelope glycoprotein (gp) or a fragment thereof, provided that the fragment contains an N-linked glycosylation site containing fragment thereof. In certain cases, the envelope gp is gp160, gp120

(e.g., gp120 monomer), gp140 (e.g., gp140 trimer) or an envelope gp fragment containing variable regions 1 and 2 (V1/V2).

In certain cases, a V3 region in a gp120 polypeptide may comprise glycan residue N301 and N332. In certain cases, the V3 region may comprise glycan residue N301 and N332 and may extend from residue 291-342 or 296-337 of A244 gp120. The gp120 may be a monomer. The numbering of the amino acid residues N301, N332, and N334 is with reference to the amino acid sequence of HIV-1 envelope polyprotein of HIV HXB having GenBank Accession No. AAB50262. AAB50262 provides a 856 amino acids long HIV-1 Env protein sequence; amino acids 34-511 define gp120 and amino acids 530 to 726 define gp41. Within gp120, the following domains are present: V1 (amino acid position 126-156); V2 (amino acid position 157-205); V3 (amino acid position 292-339); V4 (amino acid position 385-418) and V5 (amino acid position 461-471) Amino acid sequence of envelope polyprotein of HIV HXB having GenBank Accession No. AAB50262 is as follows:

(SEQ ID NO: 27)

MRVKEKYQHLWRWGWRWGTMLLGMLMICSATEKLWVTVYYGVPVWKEATT
LFCASDAKAYDTEVHNVWATHACVPTDPNPQEVVLVNVTENFNMWKNDMVE
QMHEDIISLWDQSLKPCVKLTPLCVSLKCTDLKNDTNTNSSSGRMIMEKGE
IKNCSFNISTSIRGKVQKEYAFFYKLDIIPIDNDTTSYKLTSCNTSVITQA
CPKVSFEPIPIHYCAPAGFAILKCNNKTFNGTGPCTNVSTVQCTHGIRPVV
STQLLLNGSLAEEEVVIRSVNFTDNAKTIIVQLNTSVEINCTRPNNNTRKR
IRIQRGPGRAFVTIGKIGNMRQAHCNISRAKWNNTLKQIASKLREQFGNNK
TIIFKQSSGGDPEIVTHSFNCGGEFFYCNSTQLFNSTWFNSTWSTEGSNNT
EGSDTITLPCRIKQIINMWQKVGKAMYAPPISGQIRCSSNITGLLLTRDGG
NSNNESEIFRPGGGDMRDNWRSELYKYKVVKIEPLGVAPTKAKRRVVQREK
RAVGIGALFLGFLGAAGSTMGAASMTLTVQARQLLSGIVQQQNNLLRAIEA
QQHLLQLTVWGIKQLQARILAVERYLKDQQLLGIWGCSGKLICTTAVPWNA
SWSNKSLEQIWNHTTWMEWDREINNYTSLIHSLIEESQNQQEKNEQELLEL
DKWASLWNWFNITNWLWYIKLFIMIVGGLVGLRIVFAVLSIVNRVRQGYSP
LSFQTHLPTPRGPDRPEGIEEEGGERDRDRSIRLVNGSLALIWDDLRSLCL
FSYHRLRDLLLIVTRIVELLGRRGWEALKYWWNLLQYWSQELKNSAVSLLN
ATAIAVAEGTDRVIEVVQGACRAIRHIPRRIRQGLERILL.

In certain aspects, the polypeptide is gp140. In certain aspects, the gp140 polypeptide may be a trimer.

In certain embodiments, the exogenous polypeptide is an envelope glycoprotein or a fragment thereof, provided that the fragment contains an N-linked glycosylation site containing fragment thereof and may comprise an amino acid sequence set forth below.

Clade CRF01_AE: A244_N332$_c$ rgp120 (SEQ ID NO:1)

VPVWKEADTTLFCASDAKAHETEVHNVWATHACVPTDPNPQEIDLENVTEN
FNMWKNNMVEQMQEDVISLWDQSLKPCVKLTPPCVTLHCTNANLTKANLTN
VNNRTNVSNIIGNITDEVRNCSFNMTTELRDKKQKVHALFYKLDIVPIEDN
NDSSEYRLINCNTSVIKQACPKISFDPIPIHYCTPAGYAILKCNDKNFNGT

-continued

GPCKNVSSVQCTHGIKPVVSTQLLLNGSLAEEEIIIRSENLTNNAKTIIVH
LNKSVVINCTRPSNNTRTSITIGPGQVFYRTGDIIGDIRKAYCNISGTEWN
KALKQVTEKLKEHFNNKPIIFQPPSGGDLEITMHHFNCRGEFFYCNTTRLF
NNTCIANGTIEGCNGNITLPCKIKQIINMWQGAGQAMYAPPISGTINCVSN
ITGILLTRDGGATNNTNNETFRPGGGNIKDNWRNELYKYKVVQIEPLGVAP
TRAKRRVVEREKR

The V1/V2 domain is double underlined and starts at amino acid position 83 and ends at position 171 and V3 domain is underlined and starts at amino acid position 259 and ends at amino acid position 304 in SEQ ID NO:1.

Clade CRF01_AE: A244_N332$_c$ rgp120 (SEQ ID NO:2)

VPVWKEADTTLFCASDAKAHETEVHNVWATHACVPTDPNPQEIDLENVTEN
FNMWKNNMVEQMQEDVISLWDQSLKPCVKLTPPCVTLHCTNANLTKANLTN
VNNRTNVSNIIGNITDEVRNCSFNMTTELRDKKQKVHALFYKLDIVPIEDN
NDSSEYRLINCNTSVIKQACPKISFDPIPIHYCTPAGYAILKCNDKNFNGT
GPCKNVSSVQCTHGIKPVVSTQLLLNGSLAEEEIIIRSENLTNNAKTIIVH
LNKSVVINCTRPSNNTRTSITIGPGQVFYRTGDIIGDIRKAYCNISGTEWN
KALKQVTEKLKEHFNNKPIIFQPPSGGDLEITMHHFNCRGEFFYCNTTRLF
NNTCIANGTIEGCNGNITLPCKIKQIINMWQGAGQAMYAPPISGTINCVSN
ITGILLTRDGGATNNTNNETFRPGGGNIKDNWRNELYKYKVVQIEPLGVAP
TRA

V1/V2 domain is double underlined and V3 domain is underlined.

Clade CRF01_AE: gD_A244_N332$_c$ rgp120 (UCSC1250) (SEQ ID NO:3)

MGGAAARLGAVILFVVIVGLHGVRG*KYALADASLKMADPNRFRGKDLPVLD*
*Q*LLEVPVWKEADTTLFCASDAKAHETEVHNVWATHACVPTDPNPQEIDLEN
VTENFNMWKNNMVEQMQEDVISLWDQSLKPCVKLTPPCVTLHCTNANLTKA
NLTNVNNRTNVSNIIGNITDEVRNCSFNMTTELRDKKQKVHALFYKLDIVP
IEDNNDSSEYRLINCNTSVIKQACPKISFDPIPIHYCTPAGYAILKCNDKN
FNGTGPCKNVSSVQCTHGIKPVVSTQLLLNGSLAEEEIIIRSENLTNNAKT
IIVHLNKSVVINCTRPSNNTRTSITIGPGQVFYRTGDIIGDIRKAYCNISG
TEWNKALKQVTEKLKEHFNNKPIIFQPPSGGDLEITMHHFNCRGEFFYCNT
TRLFNNTCIANGTIEGCNGNITLPCKIKQIINMWQGAGQAMYAPPISGTIN
CVSNITGILLTRDGGATNNTNNETFRPGGGNIKDNWRNELYKYKVVQIEPL
GVAPTRA gD signal sequence is underlined; mature N-terminal gD purification tag is italicized; linker sequence is in bold. V1/V2 domain is double underlined and V3 domain is underlined.

Clade B: gD-MN468-rgp120; UCSC468 (SEQ ID NO:9)

VPVWKEATTTLFCASDAKAYDTEAHNVWATHACVPTDPNPQEVELVNVTEN
FNMWKNNMVEQMHEDIISLWDQSLKPCVKLTPLCVTLNCTDLRNTTNTNNS
TDNNNSKSEGTIKGGEMKNCSFNITTSIGDKMQKEYALLYKLDIEPIDNDS
TSYRLISCNTSVITQACPKISFEPIPIHYCAPAGFAIXKCNDKKFSGKGSC
KNVSTVQCTHGIRPVVSTQLLLNGSLAEEEVVIRSEDFTDNAKTIIVHLNE
SVQINCTRPNNNTRKRIHIGPGRAFYTTKNIKGTIRQAHCNISRAKWNDTL
RQIVSKLKEQFKNKTIVFNPSSGGDPEIVMHSFNCGGEFFYCNTSPLFNSI
WNGNNTWNNTTGSNNNITLQCKIKQIINMWQKVGKAMYAPPIEGQIRCSSN
ITGLLLTRDGGEDTDTNDTEIFRPGGGDMRDNWRSELYKYKVVTIEPLGVA
PTKA

V1/V2 domain is double underlined and V3 domain is underlined.

gD-MN468-rgp120; UCSC468 (SEQ ID NO:10)

MGGAAARLGAVILFVVIVGLHGVRG*KYALADASLKMADPNRFRGKDLPVLD*
*Q*LLEVPVWKEATTTLFCASDAKAYDTEAHNVWATHACVPTDPNPQEVELVN
VTENFNMWKNNMVEQMHEDIISLWDQSLKPCVKLTPLCVTLNCTDLRNTTN
TNNSTDNNNSKSEGTIKGGEMKNCSFNITTSIGDKMQKEYALLYKLDIEPI
DNDSTSYRLISCNTSVITQACPKISFEPIPIHYCAPAGFAIXKCNDKKFSG
KGSCKNVSTVQCTHGIRPVVSTQLLLNGSLAEEEVVIRSEDFTDNAKTIIV
HLNESVQINCTRPNNNTRKRIHIGPGRAFYTTKNIKGTIRQAHCNISRAKW
NDTLRQIVSKLKEQFKNKTIVFNPSSGGDPEIVMHSFNCGGEFFYCNTSPL
FNSIWNGNNTWNNTTGSNNNITLQCKIKQIINMWQKVGKAMYAPPIEGQIR
CSSNITGLLLTRDGGEDTDTNDTEIFRPGGGDMRDNWRSELYKYKVVTIEP
LGVAPTKAKRRVVQRE gD signal sequence is underlined; mature N-terminal gD purification tag is italicized; linker sequence is in bold. V1/V2 domain is double underlined and V3 domain is underlined.

gD_MN-rgp120_N301_N332 (SEQ ID NO:12)

VPVWKEATTTLFCASDAKAYDTEAHNVWATHACVPTDPNPQEVELVNVTEN
FNMWKNNMVEQMHEDIISLWDQSLKPCVKLTPLCVTLNCTDLRNTTNTNNS
TDNNNSKSEGTIKGGEMKNCSFNITTSIGDKMQKEYALLYKLDIEPIDNDS
TSYRLISCNTSVITQACPKISFEPIPIHYCAPAGFAILKCNDKKFSGKGSC
KNVSTVQCTHGIRPVVSTQLLLNGSLAEEEVVIRSEDFTDNAKTIIVHLKE
SVQINCTRPNNNTRKRIHIGPGRAFYTTKNIKGTIRQAHCNISRAKWNDTL
RQIVSKLKEQFKNKTIVFNPSSGGDPEIVMHSFNCGGEFFYCNTSPLFNSI
WNGNNTWNNTTGSNNNITLQCKIKQIINMWQKVGKAMYAPPIEGQIRCSSN
ITGLLLTRDGGEDTDTNDTEIFRPGGGDMRDNWRSELYKYKVVTIEPLGVA
PT

V1/V2 domain is double underlined and V3 domain is underlined.

gD_MN-rgp120_N301_N332; UCSC 1320; (SEQ ID NO:13)

MGGAAARLGAVILFVVIVGLHGVRG*KYALADASLKMADPNRFRGKDLPVLD*
*Q*LLEVPVWKEATTTLFCASDAKAYDTEAHNVWATHACVPTDPNPQEVELVN
VTENFNMWKNNMVEQMHEDIISLWDQSLKPCVKLTPLCVTLNCTDLRNTTN
TNNSTDNNNSKSEGTIKGGEMKNCSFNITTSIGDKMQKEYALLYKLDIEPI
DNDSTSYRLISCNTSVITQACPKISFEPIPIHYCAPAGFAILKCNDKKFSG
KGSCKNVSTVQCTHGIRPVVSTQLLLNGSLAEEEVVIRSEDFTDNAKTIIV
HLKESVQINCTRPNNNTRKRIHIGPGRAFYTTKNIKGTIRQAHCNISRAKW
NDTLRQIVSKLKEQFKNKTIVFNPSSGGDPEIVMHSFNCGGEFFYCNTSPL
FNSIWNGNNTWNNTTGSNNNITLQCKIKQIINMWQKVGKAMYAPPIEGQIR
CSSNITGLLLTRDGGEDTDTNDTEIFRPGGGDMRDNWRSELYKYKVVTIEP
LGVAPTKAKRRVVQRE gD signal sequence is underlined; mature N-terminal gD purification tag is italicized; linker sequence is in bold. V1/V2 domain is double underlined and V3 domain is underlined.

TZ97008-rgp120; UCSC 1374; codon optimized (SEQ ID NO:23)

---

MGGAAARLGAVILFVVIVGLHGVRG*KYALADASLKMADPNRFRGKDLPVL*
*DQ*LLEVPVWKEAKTTLFCASEAKGYEKEVHNVWATHACVPTDPSPHELVL
ENVTENFNMWENDMVDQMHEDIISLWDQSLKPCVKLTPLCVTLNCTNVTG
TNVTGNDMKGEMTNCSFNATTEIKDRKKNVYALFYKLDVVQLEGNSSNST
YSTYRLINCNTSVITQACPKVSFDPIPIHYCAPAGYAILKCNNKTFNGTG
PCNNVSTVQCTHGIKPVVSTQLLLNGSLAEKEIVIRSKNLTDNVKTIIVH
LNESVEITCIRPGNNTRKSIRIGPGQAFYATGDIIGNIRQAHCNISEDKW
NKTLQMVGEKLGKLFPNKTIKEPASGGDLEITTHSFNCRGEFFYCNTTKL
FNSTYRPNANANSSSSNNTITLQCKIKQIINMWQEVGRAMYAPPIAGNIT
CTSNITGLLLVRDGGNNSTEEEIFRPGGGNMKDNWRSELYKYKVVEIKPL
GVAPTGAKRRVVEREKRAVGIGAVFLGFLGA gD signal sequence is underlined; mature N-terminal gD purification tag is italicized; linker sequence is in bold. Dotted line ( ......... ): Location of basic residues that are targets for furin and trypsin like enzymes. Translational stop codons for C-terminal purification tags can be incorporated at the beginning to this sequence. If a C-terminal purification tag may be included, then stop codon can be inserted at either the beginning or end of the sequence. Broken line ( ---------- ): C-terminal or 3' sequences not required for expression. V1/V2 domain is double underlined and V3 domain is indicated with a wavy line.

CN97001_D179N-rgp120 codon optimized (SEQ ID NO:25)

-continued

VPVWKEATTTLFCASDAKAYDTEVRNVWATHACVPADPNPQEMVLENVTEN
FNMWKNEMVNQMQEDVISLWDQSLKPCVKLTPLCVTLECRNVSSNSNGAHN
ETYHESMKEMKNCSFNATTVVRDRKQTVYALFYRLNIVPLTKKNSSENSSE
YYRLINCNTSAITQACPKVTFDPIPIHYCTPAGYAILKCNDKIFNGTGPCH
NVSTVQCTHGIKPVVSTQLLLNGSLAEGEIIIRSENLTNNVKTIIVHLNQS
VEIVCTRPGNNTRKSIRIGPGQTFYATGDIIGDIRQAHCNISEDKWNETLQ
RVSKKLAEHFQNKTIKFASSSGGDLEITTHSFNCRGEFFYCNTSGLFNGTY
TPNGTKSNSSSIITIPCRIKQIINMWQEVGRAMYAPPIEGNITCKSNITGL
LLVRDGGTEPNDTETFRPGGGDMRNNWRSELYKYKVVEIKPLGVAPTTA

V1/V2 domain is double underlined and V3 domain is underlined.

A244_N334-rgp140; codon optimized (SEQ ID NO:5)

MRVKETQMNWPNLWKWGTLILGLVIICSA*SDNLWVTVYYG*VPVWKEADTTL
FCASDAKAHETEVHNVWATHACVPTDPNPQEIDLENVTENFNMWKNNMVEQ
MQEDVISLWDQSLKPCVKLTPLCVTLHCTNANLTKANLTNVNNRTNVSNII
GNITDEVRNCSFNMTTELRDKKQKVHALFYKLDIVPIEDNNDSSEYRLINC
NTSVIKQACPKISFDPIPIHYCTPAGYAILKCNDKNFNGTGPCKNVSSVQC
THGIKPVVSTQLLLNGSLAEEEIIIRSDNLTNNAKTIIVHLNKSVVINCTR
PSNNTRTSITIGPGQVFYRTGDIIGDIRKAYCEINGTEWNKALKQVTEKLK
EHFNNKPIIFQPPSGGDLEITMHHFNCRGEFFYCNTTRLFNNTCIANGTIE
GCNGNITLPCKIKQIINMWQGAGQAMYAPPISGTINCVSNITGILLTRDGG
ATNNTNNETFRPGGGNIKDNWRNELYKYKVVQIEPLGVAPTRAKRRVVERE
KRAVGIGAMIFGFLGAAGSTMGAASITLTVQARQLLSGIVQQQSNLLRAIE
AQQHLLQLTVWGIKQLQARVLAVERYLKDQKFLGLWGCSGKIICTTAVPWN
STWSNKSLEEIWSNMTWIEWEREISNYTNQIYEILTKSQDQQDRNEKDLLE
LDKWASLWTWFDITNWLWYIK

Wild type HIV signal sequence is underlined. Mature N-terminal HIV envelope sequences for gp140 trimers is italicized.

A244_N332-rgp140 (SEQ ID NO:7)

MRVKETQMNWPNLWKWGTLILGLVIICSA*SDNLWVTVYYG*VPVWKEADTTL
FCASDAKAHETEVHNVWATHACVPTDPNPQEIDLENVTENFNMWKNNMVEQ
MQEDVISLWDQSLKPCVKLTPLCVTLHCTNANLTKANLTNVNNRTNVSNII
GNITDEVRNCSFNMTTELRDKKQKVHALFYKLDIVPIEDNNDSSEYRLINC
NTSVIKQACPKISFDPIPIHYCTPAGYAILKCNDKNFNGTGPCKNVSSVQC
THGIKPVVSTQLLLNGSLAEEEIIIRSDNLTNNAKTIIVHLNKSVVINCTR
PSNNTRTSITIGPGQVFYRTGDIIGDIRKAYCNISGTEWNKALKQVTEKLK
EHFNNKPIIFQPPSGGDLEITMHHFNCRGEFFYCNTTRLFNNTCIANGTIE
GCNGNITLPCKIKQIINMWQGAGQAMYAPPISGTINCVSNITGILLTRDGG
ATNNTNNETFRPGGGNIKDNWRNELYKYKVVQIEPLGVAPTRAKRRVVERE
KRAVGIGAMIFGFLGAAGSTMGAASITLTVQARQLLSGIVQQQSNLLRAIE

-continued

AQQHLLQLTVWGIKQLQARVLAVERYLKDQKFLGLWGCSGKIICTTAVPWN
STWSNKSLEEIWSNMTWIEWEREISNYTNQIYEILTKSQDQQDRNEKDLLE
LDKWASLWTWFDITNWLWYIK

Wild type HIV signal sequence is underlined. Mature N-terminal HIV envelope sequences for gp140 trimers is italicized.

MN-rgp140-N301_N332; (SEQ ID NO:15)

MRVKGIRRNYQHWWGWGTMLLGLLMICSA*TEKLWVTVYYG*VPVWKEATTTL
FCASDAKAYDTEAHNVWATHACVPTDPNPQEVELVNVTENFNMWKNNMVEQ
MHEDIISLWDQSLKPCVKLTPLCVTLNCTDLRNTTNTNNSTDNNNSKSEGT
IKGGEMKNCSFNITTSIGDKMQKEYALLYKLDIEPIDNDSTSYRLISCNTS
VITQACPKISFEPIPIHYCAPAGFAILKCNDKKFSGKGSCKNVSTVQCTHG
IRPVVSTQLLLNGSLAEEEVVIRSEDFTDNAKTIIVHLKESVQINCTRPNN
NTRKRIHIGPGRAFYTTKNIKGTIRQAHCNISRAKWNDTLRQIVSKLKEQF
KNKTIVFNPSSGGDPEIVMHSFNCGGEFFYCNTSPLFNSIWNGNNTWNNTT
GSNNNITLQCKIKQIINMWQKVGKAMYAPPIEGQIRCSSNITGLLLTRDGG
EDTDTNDTEIFRPGGGDMRDNWRSELYKYKVVTIEPLGVAPTKAKRRVVQR
EKRAAIGALFLGFLGAAGSTMGAASVTLTVQARLLLSGIVQQQNNLLRAIE
AQQHMLQLTVWGIKQLQARVLAVERYLKDQQLLGFWGCSGKLICTTTVPWN
ASWSNKSLDDIWNNMTWMQWEREIDNYTSLIYSLLEKSQTQQEKNEQELLE
LDKWASLWNWFDITNWLWYIK

Wild type HIV signal sequence is underlined. Mature N-terminal HIV envelope sequences for gp140 trimers is italicized.

BAL-rgp140 (SEQ ID NO:20)

MRVTEIRKSYQHWWRWGIMLLGILMICN*AEEKLWVTVYYG*VPVWKEATTTL
FCASDAKAYDTEVHNVWATHACVPTDPNPQEVALENVTENFNMWKNNMVEQ
MHEDIISLWDQSLKPCVKLTPLCVTLNCTDLRNATSRNVTNTTSSSRGMVG
GGEMKNCSFNITTGIRGKVQKEYALFYELDIVPIDNKIDRYRLISCNTSVI
TQACPKVSFEPIPIHYCAPAGFAILKCKDKKFNGKGPCSNVSTVQCTHGIR
PVVSTQLLLNGSLAEEEVVIRSENFTNNAKTIIVQLNESVEINCTRPNNNT
RKSINIGPGRAFYTTGEIIGDIRQAHCNLSRAKWNDTLNKIVIKLREQFGN
KTIVFKHSSGGDPEIVTHSFNCGGEFFYCNSTQLFNSTWNVTEESNNTVEN
NTITLPCRIKQIINMWQEVGRAMYAPPIRGQIRCSSNITGLLLTRDGGPED
NKTEVFRPGGGDMRDNWRSELYKYKVVKIEPLGVAPTKAKRRVVQREKRAV
GIGAVFLGFLGAAGSTMGAASMTLTVQARLLLSGIVQQQNNLLRAIEAQQH
LLQLTVWGIKQLQARVLAVERYLRDQQLLGIWGCSGKLICTTAVPWNASWS
NKSLNKIWDNMTWMEWDREINNYTSIIYSLIEESQNQQEKNEQELLELDKW
ASLWNWFDITKWLWYIK

Wild type HIV signal sequence is underlined. Mature N-terminal HIV envelope sequences for gp140 trimers is italicized.

Clade C: TZ97008-rgp120; UCSC 1374; codon optimized (SEQ ID NO:22)

VPVWKEAKTTLFCASEAKGYEKEVHNVWATHACVPTDPSPHELVLENVTEN
FNMWENDMVDQMHEDIISLWDQSLKPCVKLTPLCVTLNCTNVTGTNVTGND
MKGEMTNCSFNATTEIKDRKKNVYALFYKLDVVQLEGNSSNSTYSTYRLIN
CNTSVITQACPKVSFDPIPIHYCAPAGYAILKCNNKTFNGTGPCNNVSTVQ
CTHGIKPVVSTQLLLNGSLAEKEIVIRSKNLTDNVKTIIVHLNESVEITCI
RPGNNTRKSIRIGPGQAFYATGDIIGNIRQAHCNISEDKWNKTLQMVGEKL
GKLFPNKTIKEPASGGDLEITTHSFNCRGEFFYCNTTKLFNSTYRPNANAN
SSSSNNTITLQCKIKQIINMWQEVGRAMYAPPIAGNITCTSNITGLLLVRD
GGNNSTEEEIFRPGGGNMKDNWRSELYKYKVVEIKPLGVAPTGAK

BG505-rgp120. L111A-rgp120; codon optimized (SEQ ID NO:28)

MPMGSLQPLATLYLLGMLVASVLA*AENLWVTVYYG*VPVWKDAETTLFCASD
AKAYETEKHNVWATHACVPTDPNPQEIHLENVTEEFNMWKNNMVEQMHTDI
ISAWDQSLKPCVKLTPLCVTLQCTNVTNNITDDMRGELKNCSFNMTTELRD
KKQKVYSLFYRLDVVQINENQGNRSNNSNKEYRLINCNTSAITQACPKVSF
EPIPIHYCAPAGFAILKCKDKKFNGTGPCPSVSTVQCTHGIKPVVSTQLLL
NGSLAEEEVMIRSENITNNAKNILVQFNTPVQINCTRPNNNTRKSIRIGPG
QAFYATGDIIGDIRQAHCNVSKATWNETLGKVVKQLRKHFGNNTIIRFANS
SGGDLEVTTHSFNCGGEFFYCNTSGLFNSTWISNTSVQGSNSTGSNDSITL
PCRIKQIINMWQRIGQAMYAPPIQGVIRCVSNITGLILTRDGGSTNSTTET
FRPGGGDMRDNWRSELYKYKVVKIEPLGVAPTRAKSSVVGSEKSG

Wild type HIV signal sequence is underlined. Mature N-terminal HIV envelope sequences for gp140 trimers is italicized.

TV1.21-rgp120 (SEQ ID NO:32)

---

MRVMGTQKNCQQWWIWGILGFWMLMICN*TKDLWVTVYYG*VPVWREAKTTL
FCASDAKAYETEVHNVWATHACVPTDPNPQEIVLGNVTENFNMWKNDMAD
QMHEDIISLWDQSLKPCVKLTPLCVTLNCTETNVTGNRTVIGNTNDTNIA
NATYKYEEMKNCSFNVTTELRNKKHKEYALFYRLDIVPLNENGDNSKYRL
INCNTSAITQACPKVSFDPIPIHYCAPAGYAILKCNNKTFNGTGPCYNVS
TVQCTHGIKPVVSTQLLLNGSLAEEGMIIRSENLTENTKTIIVHLNESVE
INCTRPNNNTRKSVRIGPGQAFYATNDVIGDIRQAHCNISTDRWNKTLQQ
VMKKLGEHFPNKTIQFKPHAGGDIEITMHSFNCRGEFFYCNTSNLFNSTY
HSNNGTYKYNGNSSSPITLQCKIKQIVRMWQGVGQAMYAPPIAGNITCRS
NITGILLTRDGGFNTTNNTETFRPGGGDMRDNWRSELYKYKVVEIKPLGI
APTKAKRRVVQREKR

Wild type HIV signal sequence is underlined. Mature N-terminal gD purification Tag is italicized. Dotted line ( .........) indicates location of basic residues that are targets for furin and trypsin like enzymes. Translational stop codons for C-terminal purification tags can be incorporated at the beginning to this sequence. If a C-terminal purification tag is not included, then stop codon can be inserted at either the beginning or end of this sequence.

TV1.21-rgp140; not codon optimized (SEQ ID NO:34)

MRVMGTQKNCQQWWIWGILGFWMLMICN*TKDLWVTVYYG*VPVWREAKTTLF
CASDAKAYETEVHNVWATHACVPTDPNPQEIVLGNVTENFNMWKNDMADQM
HEDIISLWDQSLKPCVKLTPLCVTLNCTETNVTGNRTVIGNTNDTNIANAT
YKYEEMKNCSFNVTTELRNKKHKEYALFYRLDIVPLNENGDNSKYRLINCN
TSAITQACPKVSFDPIPIHYCAPAGYAILKCNNKTFNGTGPCYNVSTVQCT
HGIKPVVSTQLLLNGSLAEEGMIIRSENLTENTKTIIVHLNESVEINCTRP
NNNTRKSVRIGPGQAFYATNDVIGDIRQAHCNISTDRWNKTLQQVMKKLGE
HFPNKTIQFKPHAGGDIEITMHSFNCRGEFFYCNTSNLFNSTYHSNNGTYK
YNGNSSSPITLQCKIKQIVRMWQGVGQAMYAPPIAGNITCRSNITGILLTR
DGGFNTTNNTETFRPGGGDMRDNWRSELYKYKVVEIKPLGIAPTKAKRRVV
QREKRAVGIGAVFLGFLGAAGSTMGAASITLTVQARQLLSGIVQQQSNLLK
AIEAQQHMLQLTVWGIKQLQARVLAIERYLKDQQLLGIWGCSGRLICTTAV
PWNSSWSNKSEADIWDNMTWMQWDREINNYTEAIFRLLEDSQNQQEKNEKD
LLELDKWNSLWNWFNISNWLWYIK

Wild type HIV signal sequence is underlined. Mature N-terminal gD purification Tag is italicized.

1086C-rgp120; not codon optimized (SEQ ID NO:36)

MRVRGIWKNWPQWLIWSILGFWIG*NMEGSWVTVYYG*VPVWKEAKTTLFCAS
DAKAYEKEVHNVWATHACVPTDPNPQEMVLANVTENFNMWKNDMVEQMHED
IISLWDESLKPCVKLTPLCVTLNCTNVKGNESDTSEVMKNCSFKATTELKD
KKHKVHALFYKLDVVPLNGNSSSSGEYRLINCNTSAITQACPKVSFDPIPL
HYCAPAGFAILKCNNKTFNGTGPCRNVSTVQCTHGIKPVVSTQLLLNGSLA
EEEIIIRSENLTNNAKTIIVHLNESVNIVCTRPNNNTRKSIRIGPGQTFYA
TGDIIGNIRQAHCNINESKWNNTLQKVGEELAKHFPSKTIKFEPSSGGDLE
ITTHSFNCRGEFFYCNTSDLFNGTYRNGTYNHTGRSSNGTITLQCKIKQII
NMWQEVGRAIYAPPIEGEITCNSNITGLLLLRDGGQSNETNDTETFRPGGG
DMRDNWRSELYKYKVVEIKPLGVAPTEAK

Wild type HIV signal sequence is underlined. Mature N-terminal gD purification Tag is italicized.

1086C-rgp140 (SEQ ID NO:38)

MRVRGIWKNWPQWLIWSILGFWIG*NMEGSWVTVYYG*VPVWKEAKTTLFCAS
DAKAYEKEVHNVWATHACVPTDPNPQEMVLANVTENFNMWKNDMVEQMHED
IISLWDESLKPCVKLTPLCVTLNCTNVKGNESDTSEVMKNCSFKATTELKD
KKHKVHALFYKLDVVPLNGNSSSSGEYRLINCNTSAITQACPKVSFDPIPL

-continued

HYCAPAGFAILKCNNKTFNGTGPCRNVSTVQCTHGIKPVVSTQLLLNGSLA

EEEIIIRSENLTNNAKTIIVHLNESVNIVCTRPNNNTRKSIRIGPGQTFYA

TGDIIGNIRQAHCNINESKWNNTLQKVGEELAKHFPSKTIKFEPSSGGDLE

ITTHSFNCRGEFFYCNTSDLFNGTYRNGTYNHTGRSSNGTITLQCKIKQII

NMWQEVGRAIYAPPIEGEITCNSNITGLLLLRDGGQSNETNDTETFRPGGG

DMRDNWRSELYKYKVVEIKPLGVAPTEAKRRVVEREKRAVGIGAVFLGFLG

AAGSTMGAASMTLTVQARQLLSGIVQQQSNLLRAIEAQQHMLQLTVWGIKQ

LQARVLAIERYLKDQQLLGMWGCSGKLICTTAVPWNSSWSNKSQNEIWGNM

TWMQWDREINNYTNTIYRLLEDSQNQQEKNEKDLLALDSWKNLWNWFDISK

WLWYIK

Wild type HIV signal sequence is underlined. Mature N-terminal gD purification Tag is italicized.

CAP45.2.00.G3-rgp120; not codon optimized (SEQ ID NO:40)

MRVRGILRNWPQWWIWSILGFWMLIICRVM*GNLWVTVYYG*VPVWKEAKATL

FCASDARAYEKEVHNVWATHACVPTDPNPQEIYLGNVTENFNMWKNDMVDQ

MHEDIISLWDQSLKPCVKLTPLCVTLRCTNATINGSLTEEVKNCSFNITTE

LRDKKQKAYALFYRPDVVPLNKNSPSGNSSEYILINCNTSTITQACPKVSF

DPIPIHYCAPAGYAILKCNNKTFNGTGPCNNVSTVQCTHGIKPVVSTQLLL

NGSLAEEDIIIKSENLTNNIKTIIVHLNKSVEIVCRRPNNNTRKSIRIGPG

QAFYATNDIIGDIRQAHCNINNSTWNRTLEQIKKKLREHFLNRTIEFEPPS

GGDLEVTTHSFNCGGEFFYCNTTRLFKWSSNVTNDTITIPCRIKQFINMWQ

GAGRAMYAPPIEGNITCNSSITGLLLTRDGGKTDRNDTEIFRPGGGNMKDN

WRNELYKYKVVEIKPLGVAPTEARRRVVEREKR

Wild type HIV signal sequence is underlined. Mature N-terminal gD purification Tag is italicized.

CAP45.2.00.G3-_rgp140 (SEQ ID NO:42)

MRVRGILRNWPQWWIWSILGFWMLIICRVM*GNLWVTVYYG*VPVWKEAKATL

FCASDARAYEKEVHNVWATHACVPTDPNPQEIYLGNVTENFNMWKNDMVDQ

MHEDIISLWDQSLKPCVKLTPLCVTLRCTNATINGSLTEEVKNCSFNITTE

LRDKKQKAYALFYRPDVVPLNKNSPSGNSSEYILINCNTSTITQACPKVSP

DPIPIHYCAPAGYAILKCNNKTFNGTGPCNNVSTVQCTHGIKPVVSTQLLL

NGSLAEEDIIIKSENLTNNIKTIIVHLNKSVEIVCRRPNNNTRKSIRIGPG

QAFYATNDIIGDIRQAHCNINNSTWNRTLEQIKKKLREHFLNRTIEFEPPS

GGDLEVTTHSFNCGGEFFYCNTTRLFKWSSNVTNDTITIPCRIKQFINMWQ

GAGRAMYAPPIEGNITCNSSITGLLLTRDGGKTDRNDTEIFRPGGGNMKDN

WRNELYKYKVVEIKPLGVAPTEARRRVVEREKRAVGIGAVLLGFLGAAGST

MGAASITLTVQARQLLSGIVQQQSNLLRAIEAQQHMLQLTVWGIKQLQTRV

LAIERYLKDQQLLGLWGCSGKLICTTNVPWNSSWSNKSQTDIWDNMTWIQW

DREISNYSNTIYKLLEGSQNQQEQNEKDLLALDSWNNLWNWFNITNWLWYI

K

Wild type HIV signal sequence is underlined. Mature N-terminal gD purification Tag is italicized.

As noted herein, an envelope gp derived from HIV may be expressed with a tag at the N-terminus and/or the C-terminus. Sequences of exemplary tags are provided:

Herpes simplex virus I glycoprotein D ss (gD-1 ss) (SEQ ID NO:44) MGGAAARLGAVILFVVIVGLHGVRG.

Fruit bat herpes simplex virus glycoprotein D ss (FBgD-1 ss) (SEQ ID NO:45) MAYPAVIVLVCGLFWVPATQG.

Intracellular adhesion molecule ss (ICAM-1 ss) (SEQ ID NO:46) MAPSSPRPALPALLVLLGALFPGPGNA.

Tissue plasminogen activator ss (TPA ss) (SEQ ID NO:47) MDAMKRGLCCVLLLCGAVFVSPSQEIHARFRRGARW;

gD-1 tag (SEQ ID NO:48) KYALADASLKMADPNRFRGKDLPVLDQ;

FBgD-1 tag (SEQ ID NO:49) YVRADPSLSMVNPNRFRGGHLPPLVQQ;

HIV gp120 tag (SEQ ID NO:50) TDNLWVTVYYG;

6×His tag (SEQ ID NO:51) HHHHHH;

Avi tag (SEQ ID NO:52) GLNDIFEAQKIEWHE;

Strep-Tactin (Strep) tag (SEQ ID NO:53) WSHPQFEK;

His-Strep tag (SEQ ID NO: 54) HHHHHHSSWSHPQFEK;

His-Strep-6×His tag (C-terminus) (SEQ ID NO:55) HHHHHHSSWSHPQFEKSSHHHHHH; and

His-Strep-His (HSH) tag (N-terminus) (SEQ ID NO:56) HHHHHHWSHPQFEKHHHHHHQSG.

As noted herein, HIV env gp can be expressed with or without the following sequence at the C-terminus. KRRVVQRE (SEQ ID NO:57). This sequence includes location of basic residues that are targets for furin and trypsin like enzymes. Translational stop codons for C-terminal purification tags can be incorporated at the beginning to this sequence. If a C-terminal purification tag is included, then stop codon can be inserted at either the beginning or end of the sequence.

As noted herein, HIV env gp can be expressed with or without the following sequence at the C-terminus: AVGIGA VFLGFLGA RRVVEREKR (SEQ ID NO:58). Dotted line (........): This sequence includes location of basic residues that are targets for furin and trypsin like enzymes. Translational stop codons for C-terminal purification tags can be incorporated at the beginning to this sequence. If a C-terminal purification tag is included, then stop codon can be inserted at either the beginning or end of the sequence. Broken line (- - - - - -): C-terminal or 3' sequences not required for expression.

EXAMPLES

Below are examples of specific embodiments for carrying out the present invention. The examples are offered for illustrative purposes only and are not intended to limit the scope of the present invention in any way.

Efforts have been made to ensure accuracy with respect to numbers used (e.g., amounts, temperatures, etc.), but some experimental error and deviation should, of course, be allowed for.

Example 1

Identification of a Protease Mediating Cleavage of Gp120

Vaccines require an antigen that elicits neutralizing antibodies. Typically, the antigen is derived from the envelope protein of the virus. gp120 is a monomer of the trimeric envelope (Env) protein of HIV. gp120 was a major component the HIV vaccine antigen used in the RV144 clinical trial, which has been the only trial to result in efficacy at reducing rates of infection.

Figure 2A:
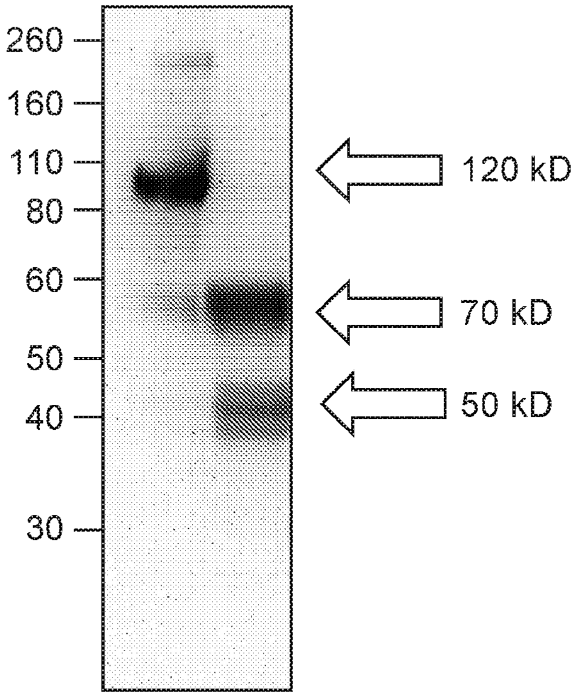
FIGS. 2A and 2B. Clade B gp120 is difficult to manufacture in Chinese Hamster Ovary cells: Typically, the 120 kD protein is cleaved into a 70 kD and 50 kD fragment.
Figure 2B:
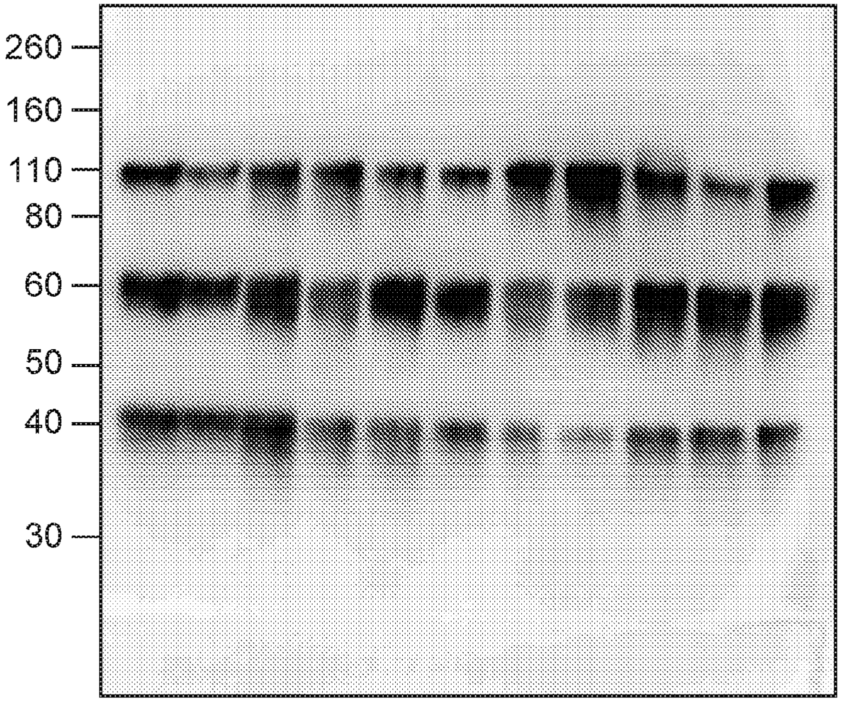

Clade B is a genetic subtype of HIV strains, prevalent in North America and Europe. Clade B gp120 is difficult to manufacture in Chinese Hamster Ovary cells. Typically, the 120 kD protein is cleaved into a 70 kD and 50 kD fragment. See FIG. 2, left panel: Lane 1. purified MN gp120 (clade B), Lane 2. purified MN gp120 (clade B) incubated with 10× concentrated CHO-S supernatant; right panel: Supernatant from clones of Bal gp120 (clade B) producing $MGAT^-$ CHO-S Bal cell line cultured in a 96-well plate for 1.5 days. All clones contain significant proteolytic activity against MN gp120 (clade B).

CHO cell lines are used for production of gp120 as well as other proteins for vaccines and other biopharmaceutical use. Thus, producing a CHO cell line that has reduced protease activity, such as, that of the protease responsible for cleavage of gp120 will be advantageous.

The following workflow was conducted to identify the protease(s) causing cleavage of gp120: Conventional protein chemistry to enrich for the protease in CHO cell culture supernatants; Identification of the protease in partially purified supernatants by mass spectroscopy; Identification of main protease responsible for cleavage of clade B gp120s in growth conditioned medium from CHO cells.

Proteolysis by a serine protease from CHO cells has been previously observed. Clements, G. J. et al. The V3 loops of the HIV-1 and HIV-2 surface glycoproteins contain proteolytic cleavage sites: a possible function in viral fusion? *AIDS Res. Hum. Retroviruses* 7, 3-16 (1991) identified that HIV1 and HIV2 gp is cleaved at GPGR↓AF by a thrombin-like serine protease. To overcome proteolysis, several methods unsuitable to large scale production have been used: Addition of protease inhibitors; Growth in serum containing cell culture medium; Selective purification of uncleaved gp120 using antibody immunoaffinity columns; and Production in human HEK 293 cells (lower productivity, non-standard manufacturing cell line).

Identifying the serine protease in CHO cells that mediate cleavage of gp120 is challenging because more than 2000 proteins are secreted from CHO cells and there are numerous proteases for protein degradation. Among serine proteases, there are four different types: HTRA1; HTRA2, mitochondrial; Calcium-dependent serine protease, C1s; and Cathepsin A.

Enrichment of protease from CHO cell culture supernatant was carried out using a series of chromatography columns to enrich for protein containing proteolytic activity. Individual chromatography fractions (CHO cell culture supernatant was fractionated based on size using size exclusion chromatography, followed by further purification on strong anion-exchange column) were assayed for the presence of protease activity against purified gp120. The fractions containing the protease resulted in the cleavage of the intact gp120, as seen by SDS-PAGE.

Figure 3:
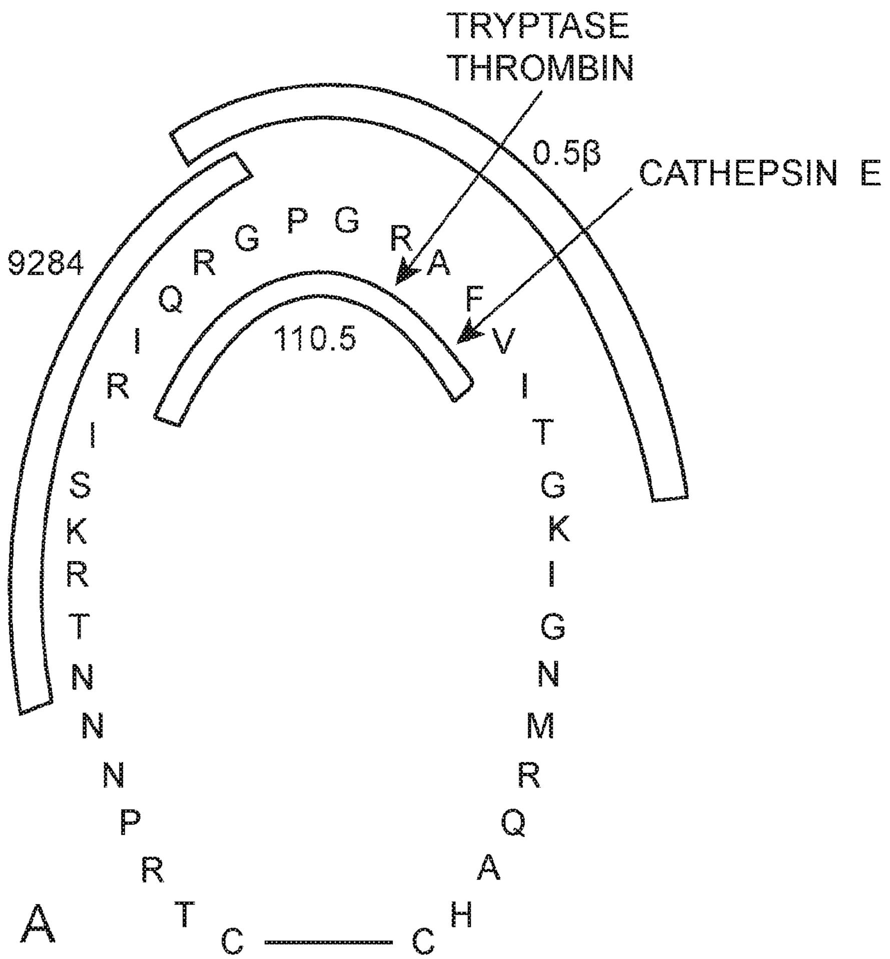
FIG. 3. Clements, G. J. et al. *AIDS Res. Hum. Retroviruses* 7, 3-16 (1991) reported that the V3 loops of the HIV-1 and HIV-2 surface glycoproteins contain proteolytic cleavage sites. (SEQ ID NO: 31)
Figure 4A:
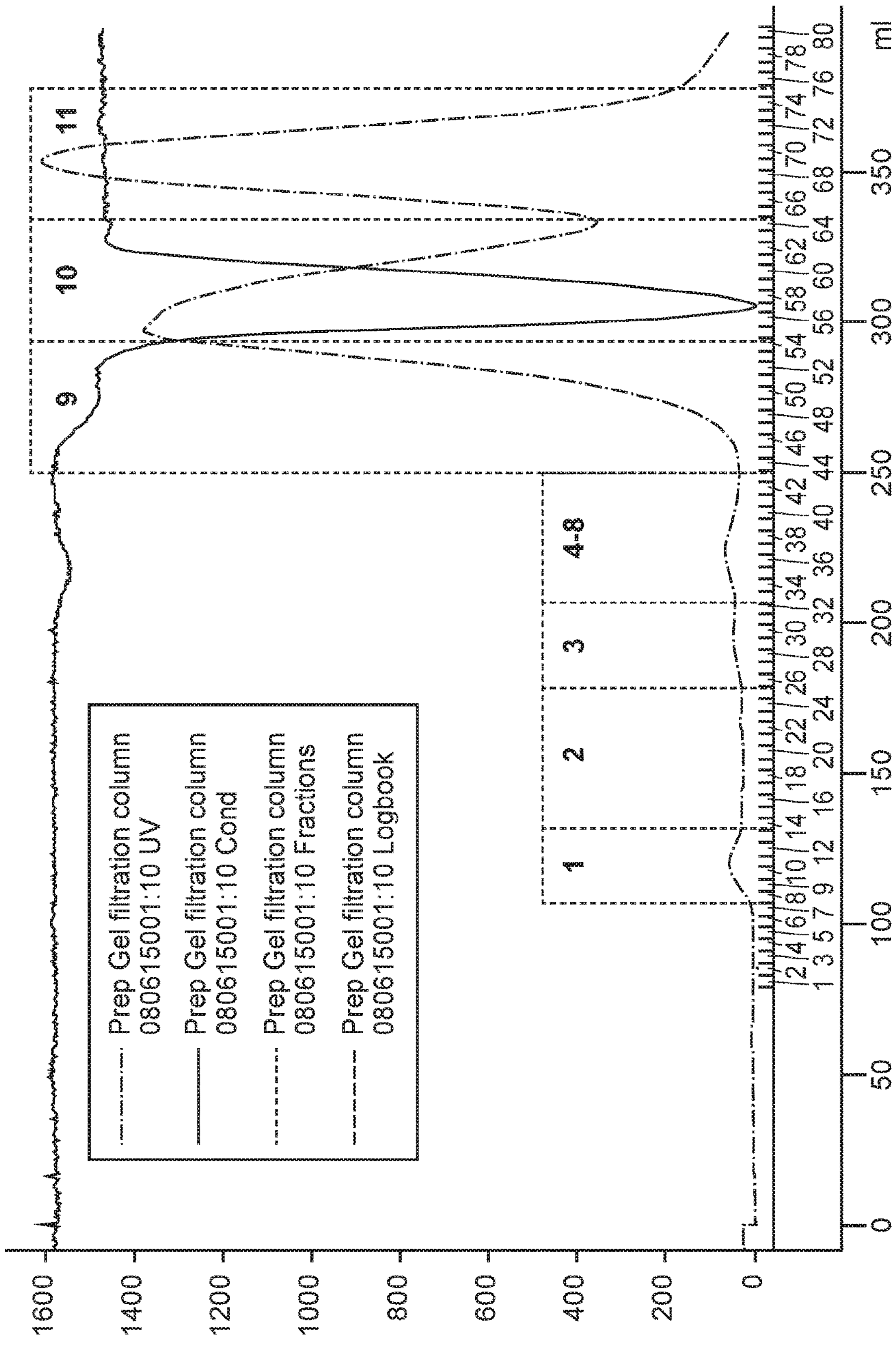
FIGS. 4A and 4B. Purification products from CHO cell supernatant purified in a size exclusion column. Fractions 2, 3 were capable of cleaving gp120 and were pooled and put onto a subsequent ion exchange column. Fraction 10 contained some cathepsins.
Figure 4B:
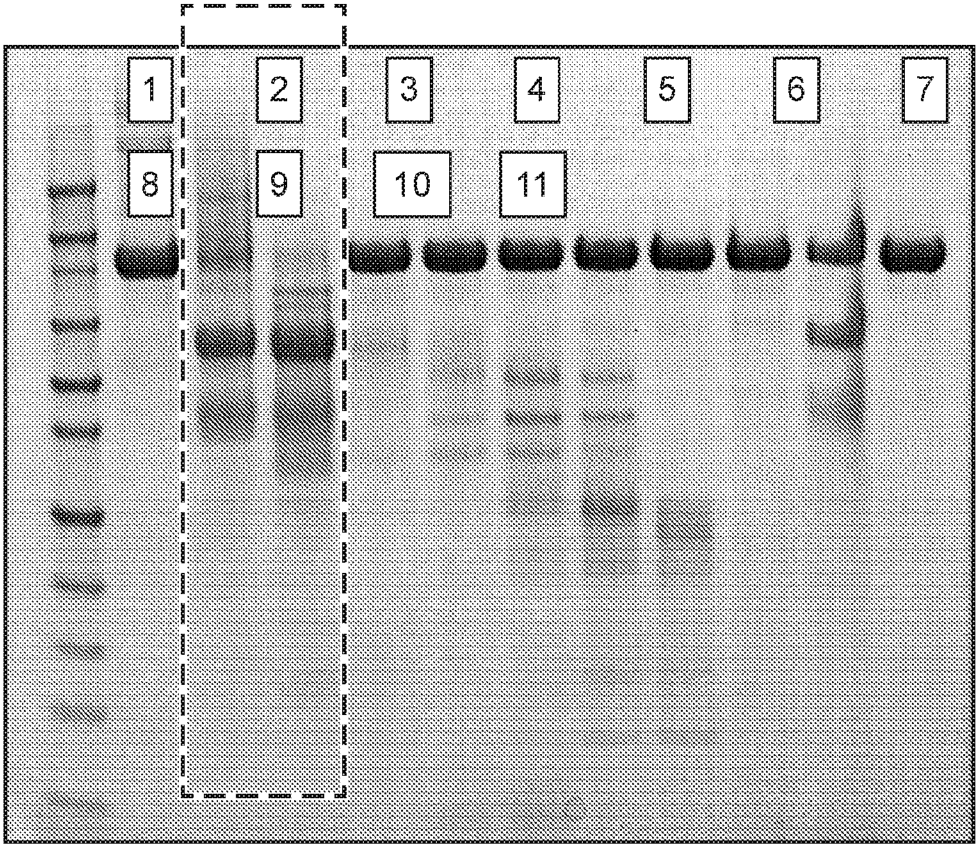

FIG. 3, Fractions 2, 3 were capable of cleaving gp120 and were pooled and put onto a subsequent ion exchange column. Fraction 10 contained some cathepsins FIG. 4, SDS-PAGE analysis of fractions 2 and 3 further purified by QHP ion-exchange chromatography.

Figure 5A:
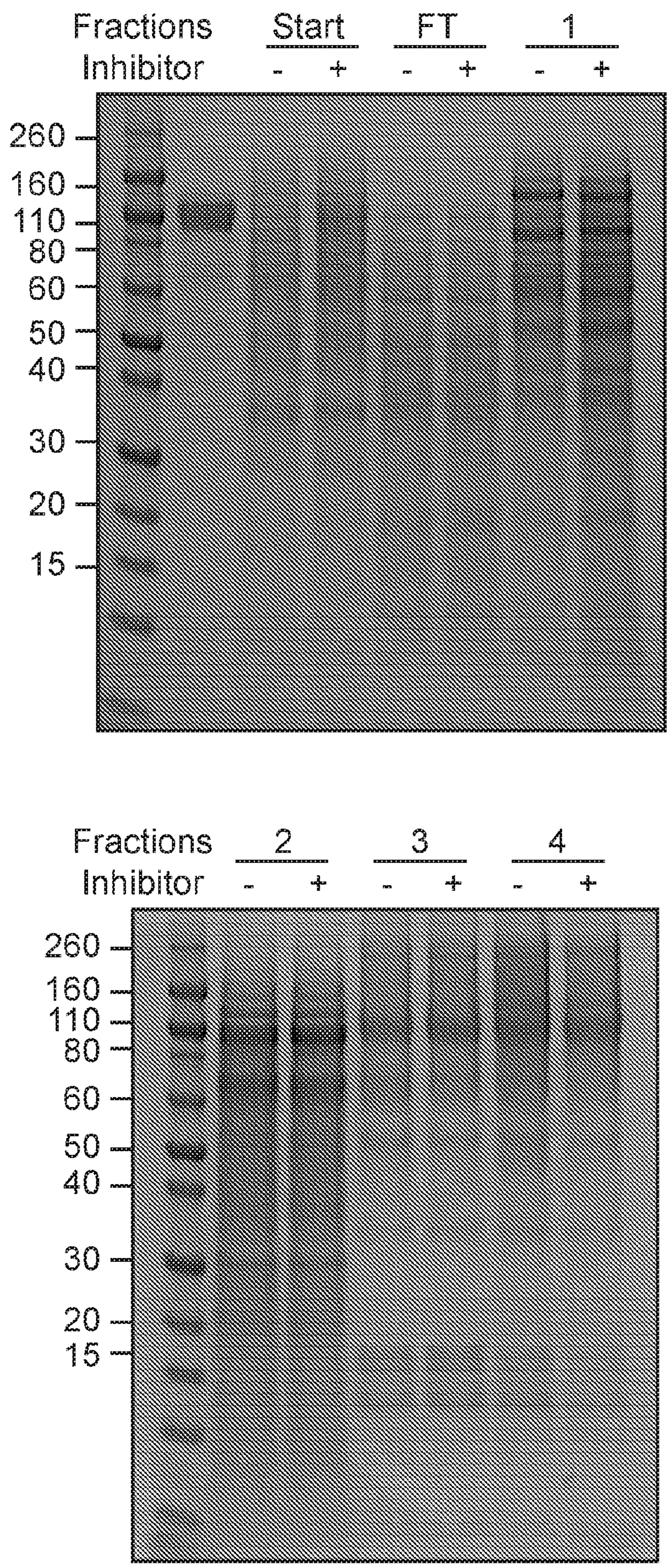
FIGS. 5A and 5B. Analysis of fractions 2 and 3 by Q-sepharose high performance (QHP) ion-exchange chromatography (SDS-PAGE).
Figure 5B:
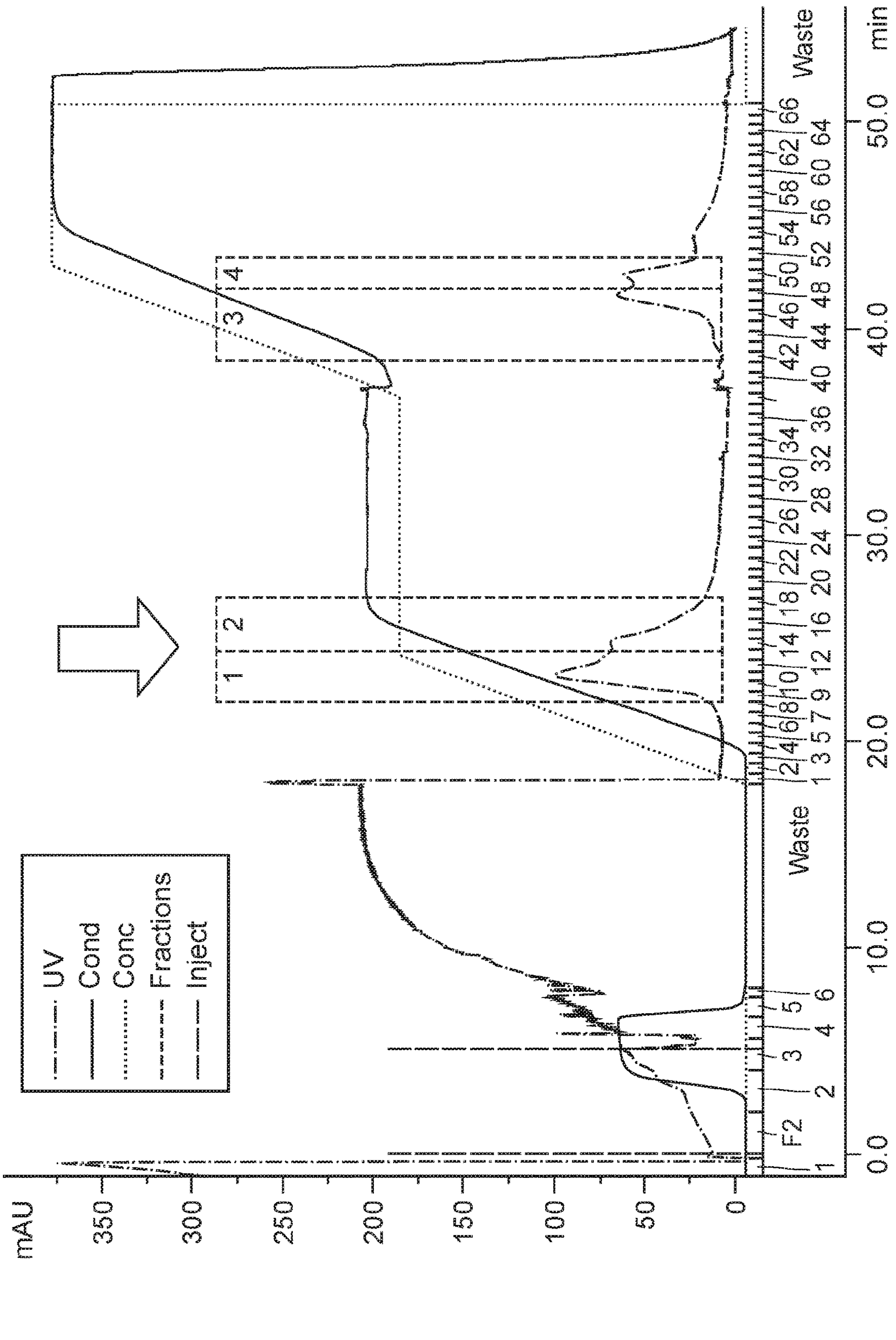

FIG. 5, Western blot of QHP, ion-exchange fractions to locate fractions with protease activity.

Figure 6A:
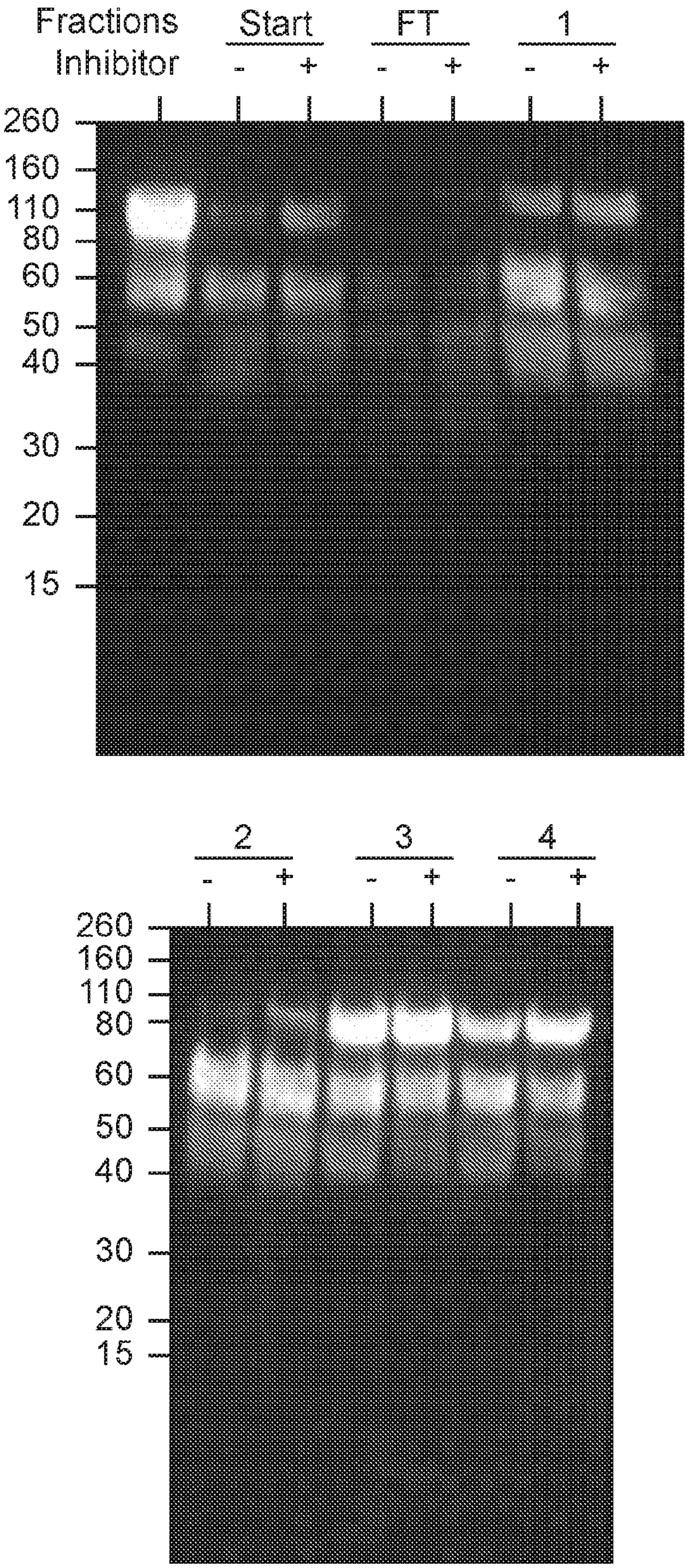
FIGS. 6A and 6B. Western blot of QHP, ion-exchange fractions to locate fractions with protease activity.
Figure 6B:
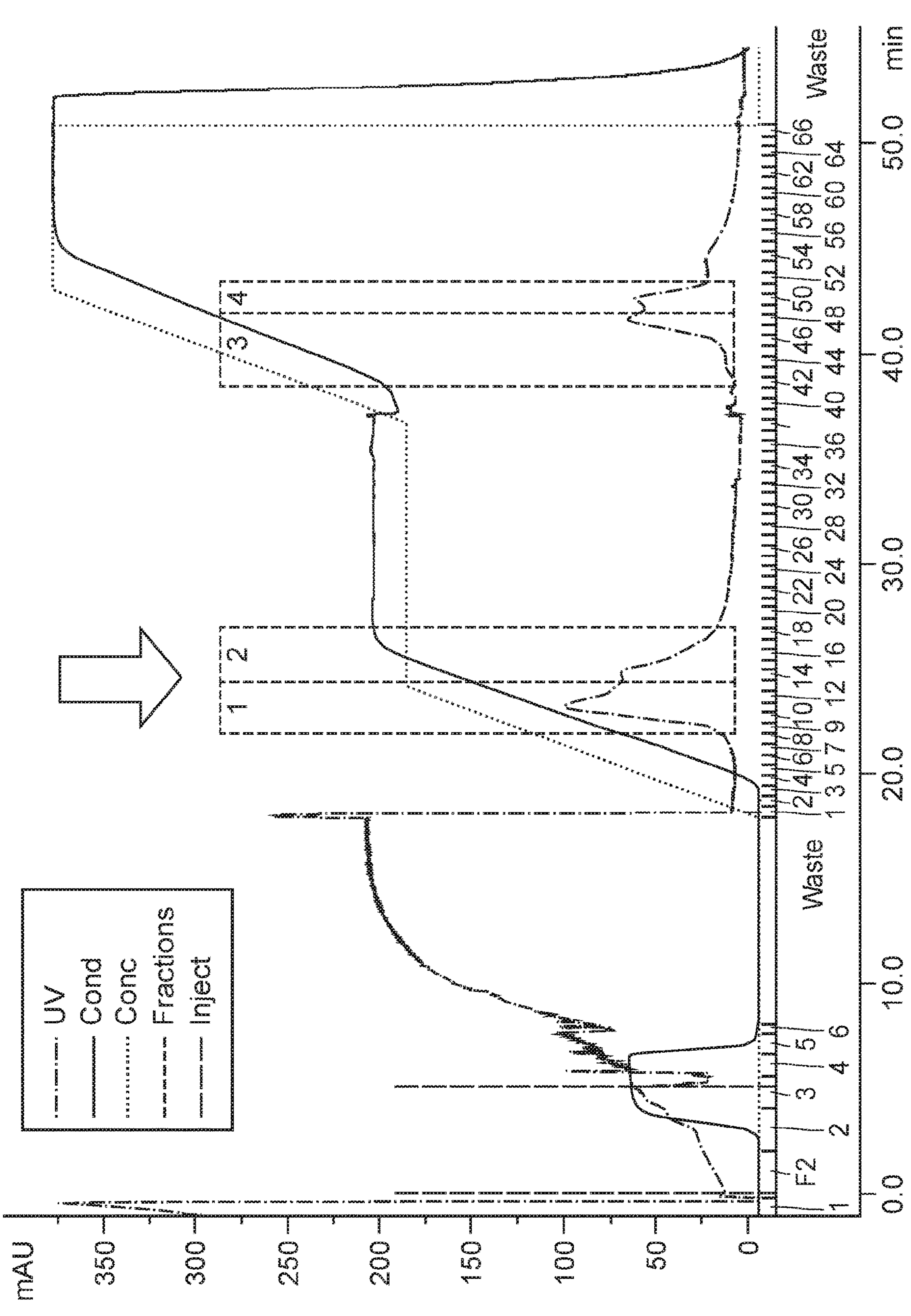

FIG. 6, Identification of protease present in fractions containing gp120 cleavage activity. Proteins from column fractions 1 and 2 were digested into peptides; Tandem mass spectroscopy (MS) provided the amino acid sequence of peptides; Uniprot database was searched to identify proteins containing the peptide sequence.

Figure 7:
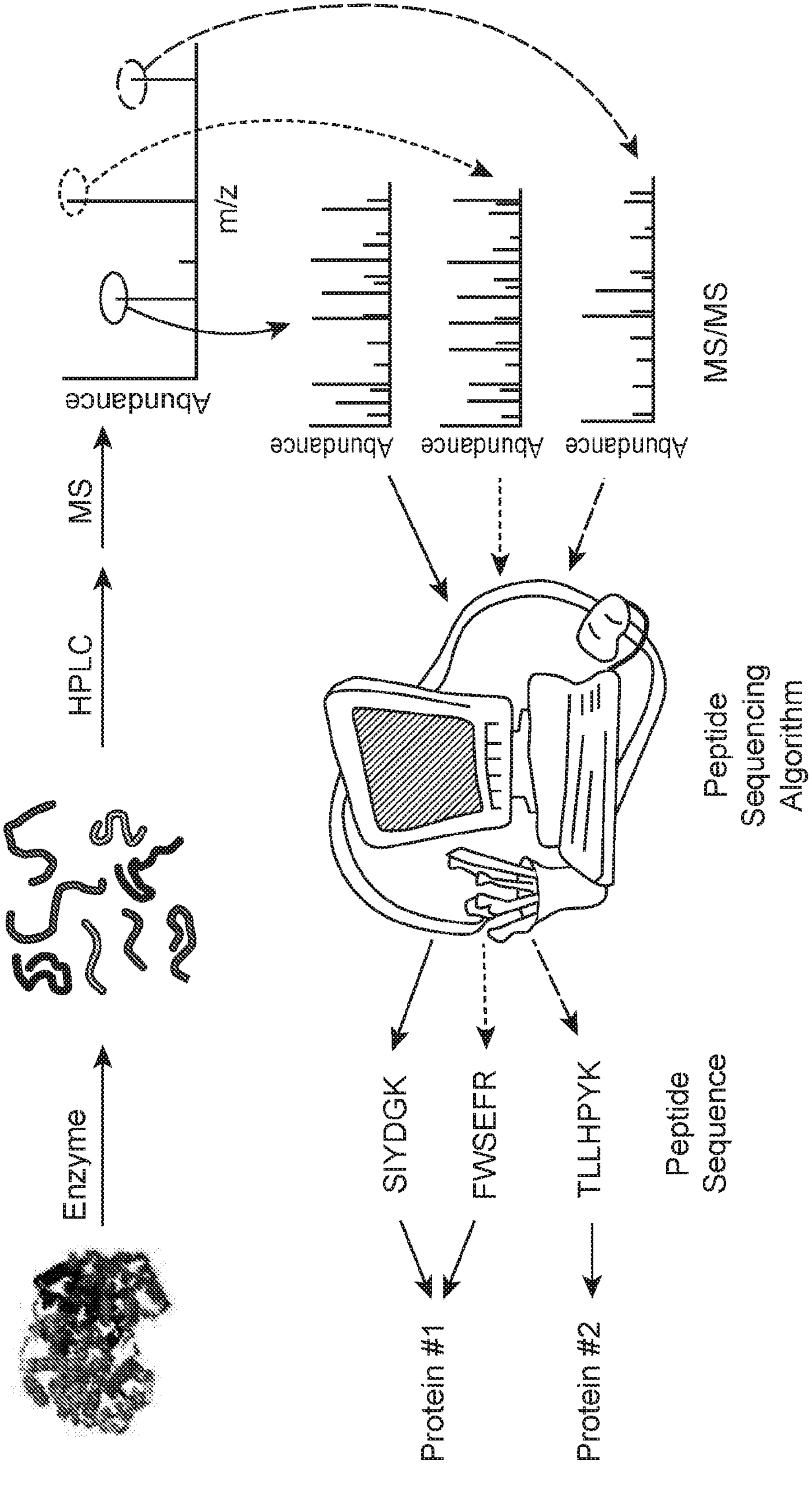
FIG. 7. Identification by mass spectroscopy of a calcium-dependent serine protease that cleaves gp120. Procedure involved: 1. Digest proteins from column fractions into peptides; 2. Tandem MS provides the amino acid sequence of peptides; 3. Search database to identify proteins containing the peptide sequence.

FIG. 7, Calcium-dependent serine proteinase OS (Accession No. G3GUR0) was identifies from a BLAST of the sequences identified by MS against the Uniprot database. Other proteins that were also identified as containing the sequences identified by MS includes chondroitin sulfate proteoglycan, Hsp90, and some extra cellular matrix proteins.

Figures 8A, 8B:
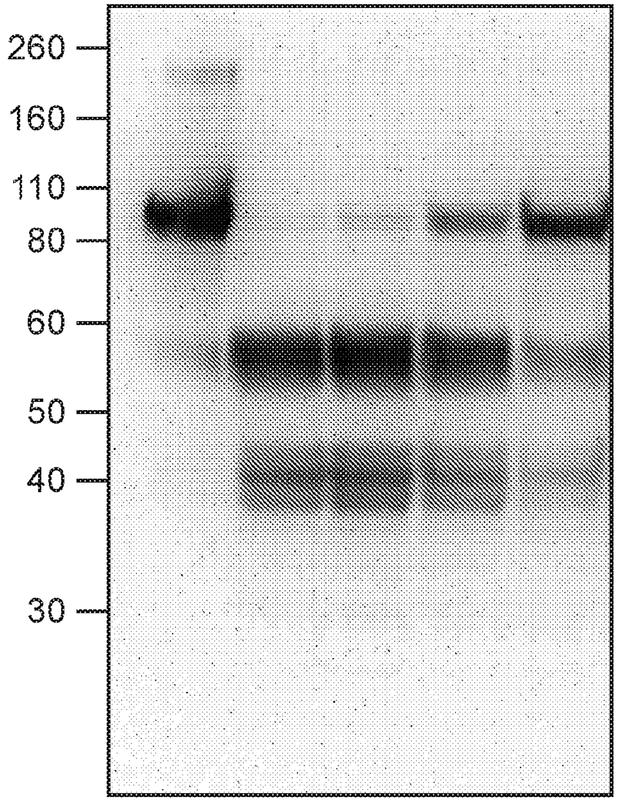
FIGS. 8A and 8B. Inhibition of proteolysis with EGTA, a calcium-chelating agent suggests C1s is the major protease.

FIG. 8, inhibition of proteolysis of gp120 in CHO cell supernatant with EGTA, a calcium-chelating agent suggested that C1s is the major protease responsible for gp120 cleavage.

Materials and Methods

Cells and Antibodies.

FreeStyle CHO-S cells (Thermo Fisher, Life Technologies, Carlsbad, CA, US) were used. A goat polyclonal antibody raised against gp120 was used for the western blot analysis.

Cell Culture Media.

CHO Growth A media (Irvine Scientific, Santa Ana, CA) was used to maintain CHO cell cultures. The additive feed was comprised of Proyield Cotton CNE50M-UF (FrieslandCampina, Delhi, NY) and TC Yeastolate Ultra-Filtered (BD Biosciences, San Jose, CA).

CRISPR/Cas9 Target Design and Plasmid Preparation.

The C1s gene is available at chogenome website. Each of the guide RNAs were cloned into the CRISPR Nuclease Vector (GeneArt, Thermo Fisher) which expresses Cas9 and an orange fluorescent protein reporter. Four target sequences were acquired from the CHO genome using CRISPy Cas9 target finder (Lasse Ebdrup Pedersen, Novo Nordisk Foundation Center for Biosustainability, Technical University of Denmark). The target sequences were as follows: sgRNA1 GATAATCTCAGGAGGCGTCG (SEQ ID NO: 17), sgRNA2 GCCAGTAAACCGCTCTTCGT (SEQ ID NO: 18), sgRNA3 GGGCTCTTATTGACGAGTAC and sgRNA4 GTTGACAGCCGCTCATGTTG (SEQ ID NO: 19). To ligate sgRNA inserts into the vector, DNA oligos were synthesized (Eurofins Genomics, Louisville, KY). Bacterial amplification of the completed vectors was done in One Shot TOP10 Chemically Competent *E. coli* following the recommended protocol (Thermo Fisher). Culture were grown in 15 ml LB broth overnight at 37° C. at 250 rpm. Minipreps (Qiagen, Redwood City, CA) were performed using the recommended protocol and submitted for Sanger sequencing (University of California Core Sequencing Facility, Berkeley, CA) with the U6 primer provided in the GeneArt CRISPR kit. 1 L Maxipreps (Qiagen) were performed using the recommended protocol. Plasmid DNA was eluted into endotoxin-free water at concentrations greater than 5 mg/ml for optimal transfection efficiency.

Electroporation.

Plasmids were transfected by electroporation using the Maxcyte STX scalable transfection system (MaxCyte Inc., Gaithersburg, MD). Cells were spun down at 250 g for 10 minutes and resuspended in MaxCyte EP buffer (MaxCyte) at a density of $200\times10^6$ cells/mL. $80\times10^6$ cells and 120 ug of CRISPR Nuclease Vector DNA were combined for a total volume of 400 ul in the OC-400 processing assembly (MaxCyte). The CHO protocol in the MaxCyte STX software was used for transfections. After electroporation, cells were transferred into a 125 ml Erlenmeyer flask and incubated without shaking at 37° C. for 40 minutes. 15 ml of pre-warmed CHO Growth A media (Irvine Scientific, Santa Ana, CA) with 2 mM Glutamax (Sigma-Aldrich St. Louis, MO) was added to the flasks, and the flasks were transferred to Kuhner shakers at 37° C., 8% $CO_2$, and 125 rpm.

Plating, Expansion, and Culture of CRISPR Transfected CHO-S Cells.

After three days, cells were analyzed for knockout efficiency using TIDE analysis (Desktop Genetics). $0.5\times10^6$ cells were spun down and boiled in 10 ul of milliQ water. 5 ul of cell lysate was used in a 25 ul PCR reaction with OneTaq Hot Start 2× Master Mix with Standard Buffer (New England BioLabs, Ipswitch, MA). PCR products were run on 2% agarose gels to confirm size and gel purified with a Zymoclean kit (Zymo Research, Irvine, CA) For TIDE analysis of sgRNA4, 404 bases from 10,392 to 10,796 bp was amplified by PCR with the forward primer GCCAGCATTGATTCCTGCATCTC (SEQ ID NO: 21) and the reverse primer CCCATTTTCACGGGGTCTTTCAG (SEQ ID NO: 24). Single cell cloning was performed three days after transfection and cells were diluted to 0.5 cells/well in Costar 96 well tissue-culture treated microplates (Corning, Corning, NY). Single cell colonies were grown for 14-21 days at 37 C, 8% $CO_2$ and 85% humidity. 15 ul of supernatant was assayed by immunoblot for proteolysis of Bal Experimental Protein Production.

Cells were maintained at 0.5-8e6 cells/ml and passaged every two to four days in 125- or 250-ml shake flasks. For scale-up protein production, 1 mM sodium butyrate was added to cultures and the temperature lowered to 32° C. Media was supplemented with a feed consisting of Proyield Cotton CNE50M-UF (FrieslandCampina, Delhi, NY) and TC Yeastolate Ultra-Filtered (BD Biosciences, San Jose, CA) given every three days at 10% of the culture volume.

Protein Purification

Supernatant was 0.2 um filtered (EMD Millipore, Hayward, CA) and purified by the gD tag using an immunoaffinity column consisting of the 34.1 mAb on AminoLink Plus Coupling resin (Thermo Fisher Scientific). Mobile phase A was 50 mM Tris, 0.5 M NaCl, pH 7.4 and mobile phase B was 0.1 M glycine, pH 3. 1M Tris was added to eluate at 1:10 ratio of eluate:buffer for neutralization. Subsequent size exclusion chromatography was performed on an S200 gel filtration column (General Electric Healthcare, Sunnyvale, CA) using TBS, pH 8.

Example 2

Generation of $C1s^-$ CHO Cell Line

This report describes the use of the CRISPR/Cas9 gene editing system to inactivate the C1s gene in CHO cells. The C1s target sequence has the following sequence:

5' GTTGACAGCCGCTCATGTTG*TGG 3' (SEQ ID NO:26)

The underlined sequence indicates region used to design the gRNA. CRISPER cut site between G and T is indicated by the *.

Figure 9:
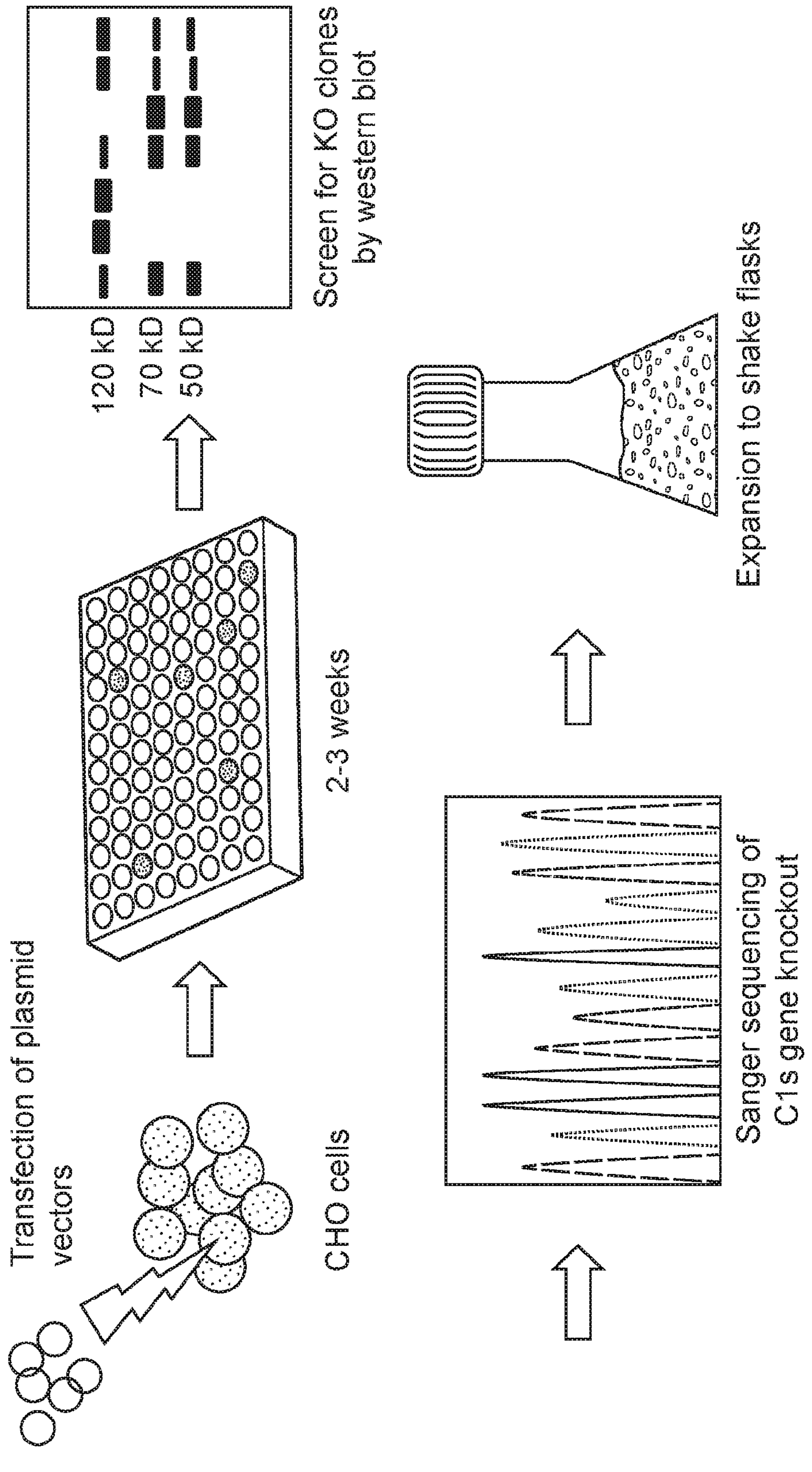
FIG. 9 illustrates procedure for knockout of C1s in CHO cells expressing Bal gp120, a clade B antigen.

FIG. 9 illustrates procedure for knockout of C1s in CHO cells expressing Bal gp120, a clade B antigen.

Figure 10:
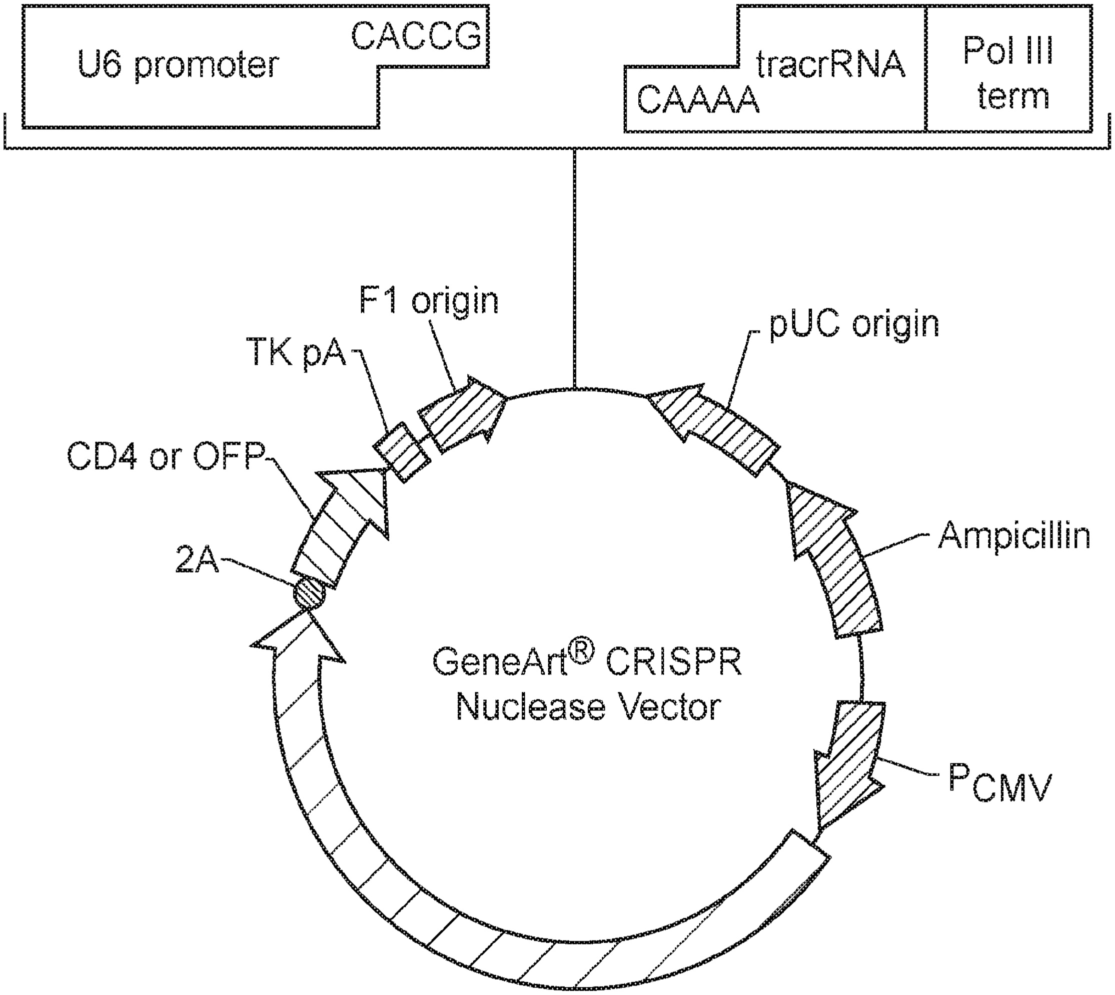
FIG. 10. Plasmid for transfection of Cas9 and guide RNA. The transfected plasmid contains the gene for Cas9 and the single guide RNA. Cas9 is the enzyme that cuts DNA. The guide RNA tells Cas9 where to cut. Target sequences were designed using CRISPy against the CHO-K1 genome: see web address "http://" followed by "staff.biosustain." followed by "dtu.dk/laeb/crispy".

FIG. 10. Plasmid for transfection of Cas9 and guide RNA. The transfected plasmid contains the gene for Cas9 and the single guide RNA. Cas9 is the enzyme that cuts DNA. The guide RNA tells Cas9 where to cut. Target sequences were designed using CRISPy against the CHO-K1 genome: see web address "http://" followed by "staff.biosustain." followed by "dtu.dk/laeb/crispy".

Figure 11:
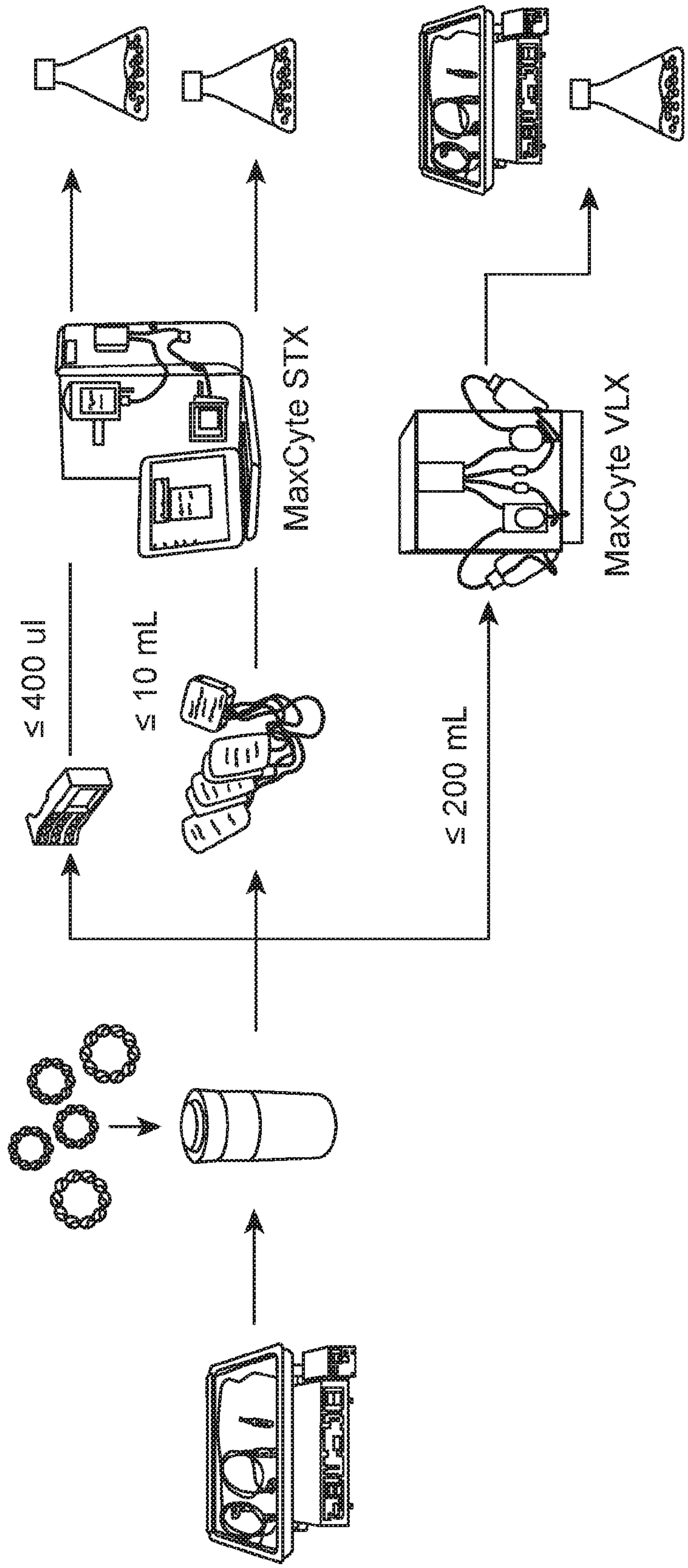
FIG. 11 provides a schematic of Maxcyte Electroporation for high transfection efficiency. Cas9/guide RNA plasmids are transfected into CHO cells using the Maxcyte electroporation system. Maxcyte electroporation system provides 95% transfection efficiency by electroporation, versus 30% by other chemical transfection methods.

FIG. 11 provides a schematic of Maxcyte Electroporation for high transfection efficiency. Cas9/guide RNA plasmids are transfected into CHO cells using the Maxcyte electroporation system. Maxcyte electroporation system provides 95% transfection efficiency by electroporation, versus 30% by other chemical transfection methods.

Figure 12A:
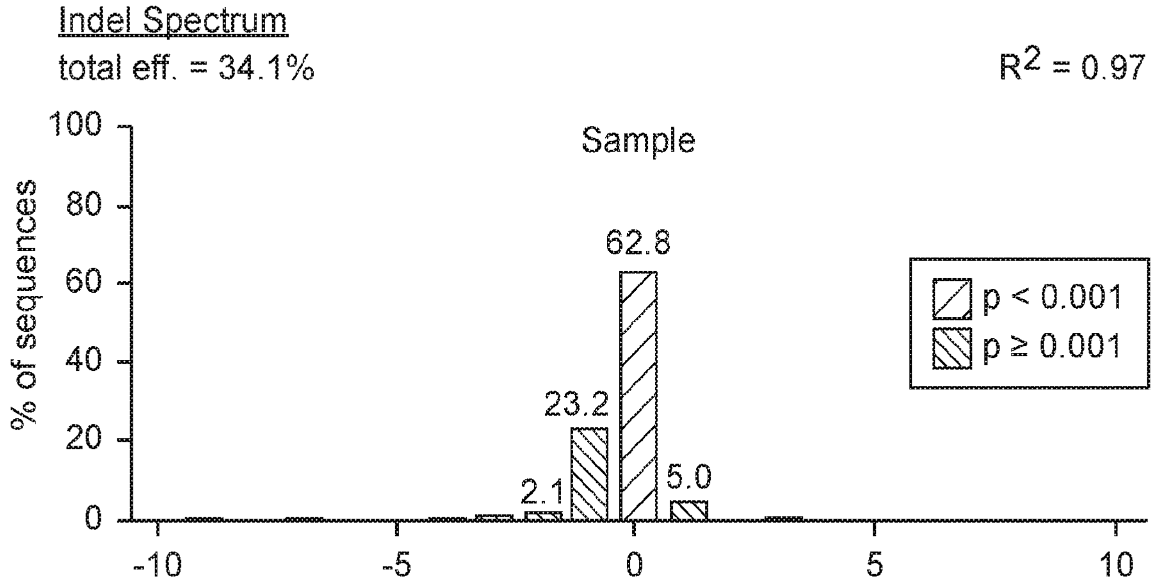
FIGS. 12A and 12B. Depict a bioinformatics tool for measurement of CRISPR knockout efficiency. Knockout efficiency is determined using an online webtool called TIDE or Tracking of Indels by Decomposition. Example data: Darker columns=Parent cells with gene knockout. 2.1 and 23.2, and 5.0% cells included and indel. Lighter column=wildtype without knockout. 62.8% of the cells did not contain an indel.
Figure 12B:
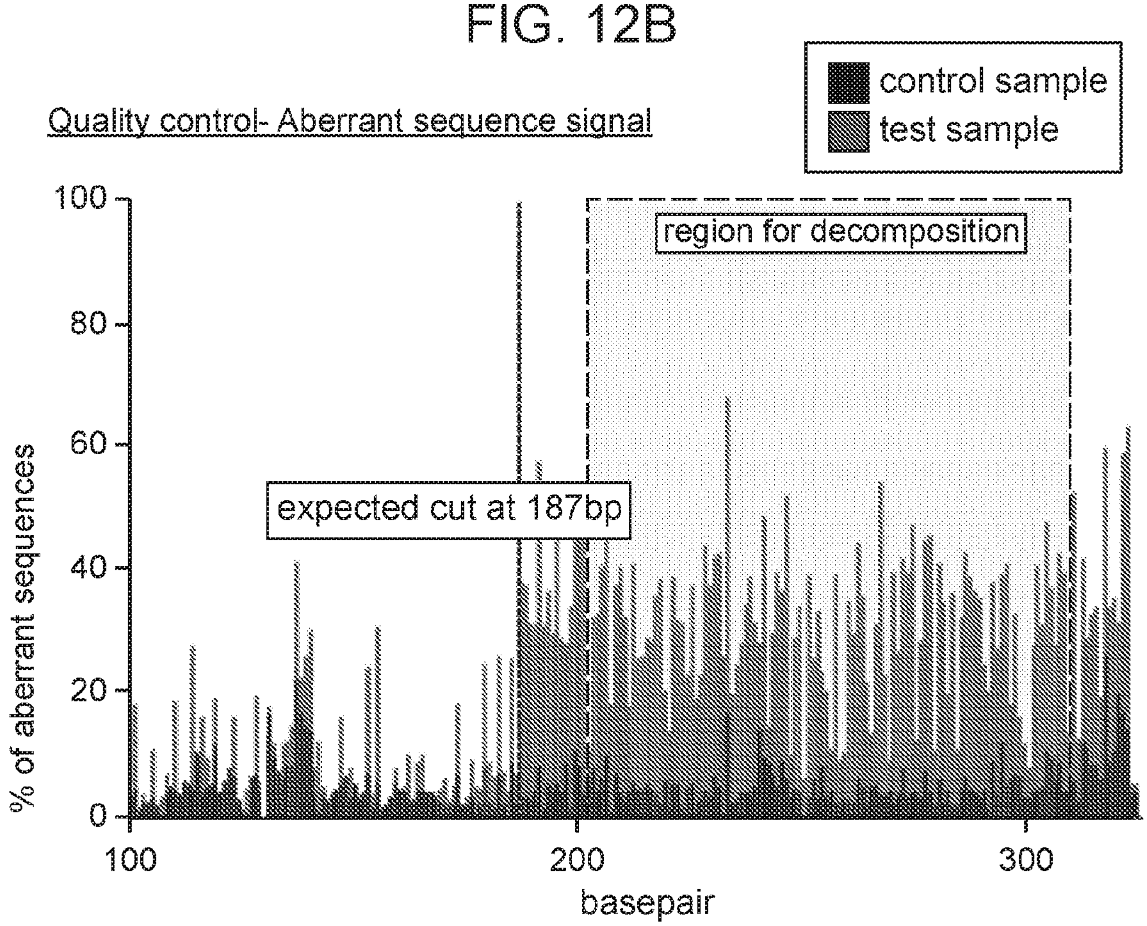

FIGS. 12A and 12B. Depict a bioinformatics tool for measurement of CRISPR knockout efficiency. Knockout efficiency is determined using an online webtool called TIDE or Tracking of Indels by Decomposition. Example data: Darker columns=Parent cells with gene knockout. 2.1 and 23.2, and 5.0% cells included and indel. Lighter column=wildtype without knockout. 62.8% of the cells did not contain an indel.

Figure 13A:
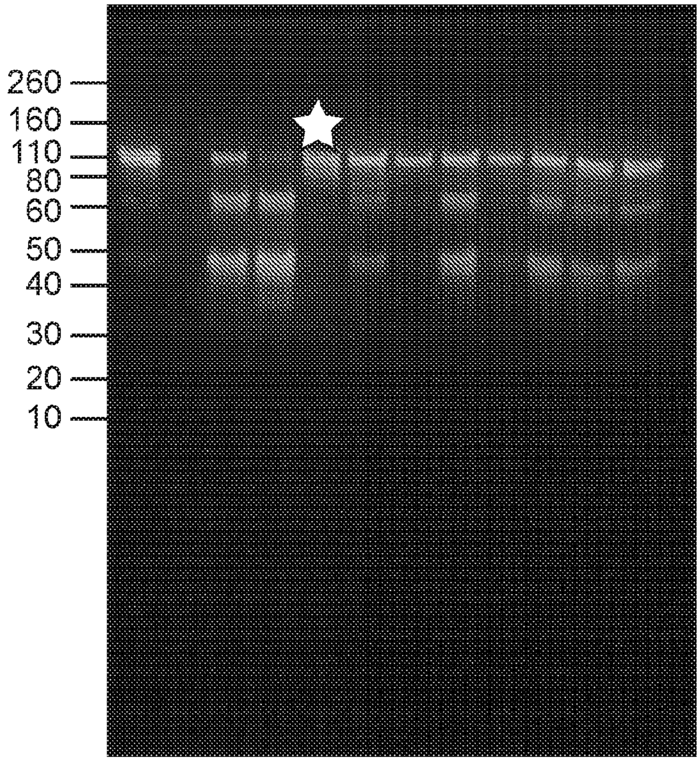
FIGS. 13A and 13B depict accumulation of uncleaved gp120 in clones with C1s knock-out. Single cell cloning: cells are diluted to 0.5 cells/well to generate homogenous clonal populations. Marked clones show accumulation of uncleaved gp120 and inactivation of C1s gene by genomic DNA sequencing.
Figure 13B:
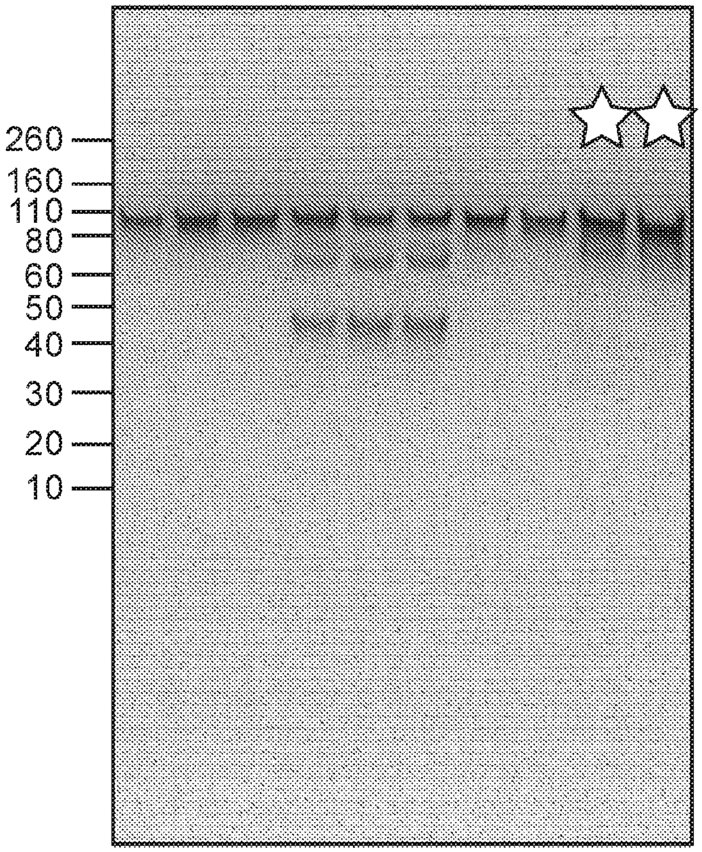

FIGS. 13A and 13B depict accumulation of full-length, uncleaved gp120 in clones with C1s knock-out. Single cell cloning: cells are diluted to 0.5 cells/well to generate homogenous clonal populations. Marked clones show accumulation of full-length, uncleaved gp120 and inactivation of C1s gene by genomic DNA sequencing.

Figure 14:
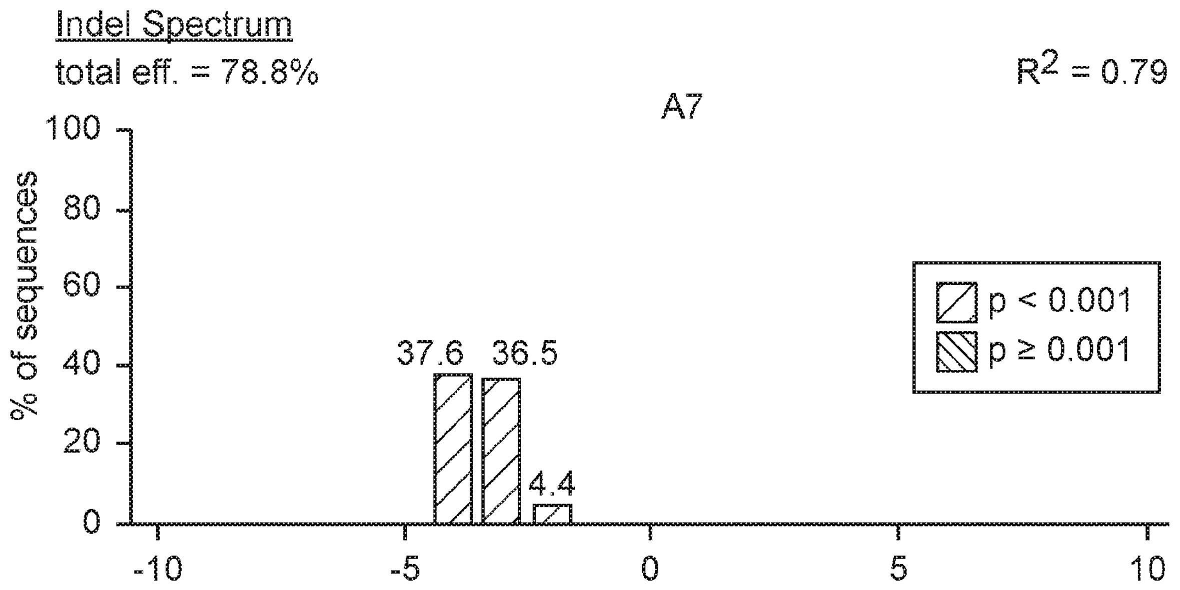
FIG. 14. Sequencing of clones matches expected Cas9-mediated gene edits as predicted by TIDE analysis.
Figure 14:
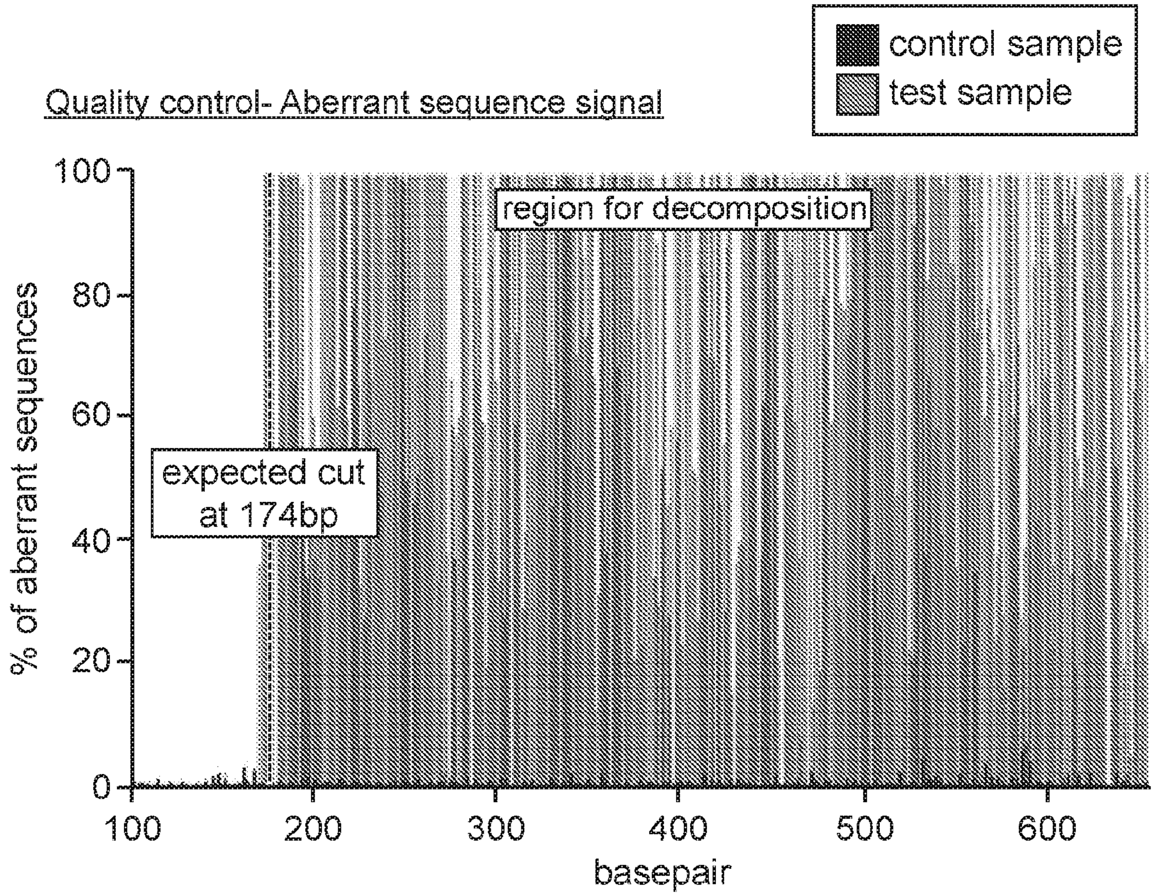

FIG. 14. Sequencing of clones matches expected Cas9-mediated gene edits as predicted by TIDE analysis.

Figures 15, 16:
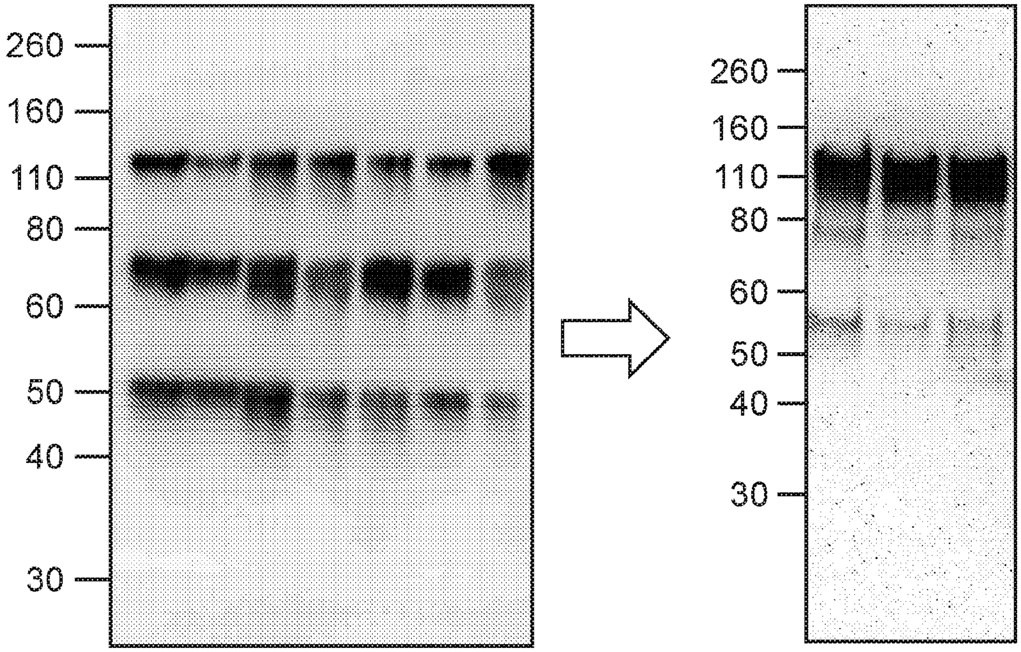
FIG. 15. Arrow indicates expected CRISPR cut site. Nucleotides in bold font depict the sequence of C1s used as the target sequence. Underlined nucleotides indicate deleted nucleotides. (top to bottom: SEQ ID NO: 26; SEQ ID NO: 29; SEQ ID NO: 30)
FIG. 16. CRISPR/Cas9 engineering of a protease-deficient CHO cell line. Proteolysis of Bal gp120 in $MGAT1^-$ CHO cell line vs. expression of full-length gp120 in C1s knockout $MGAT1^-$ CHO cell line.

FIG. 15, Blue arrow indicates expected CRISPR cut site. Nucleotides in bold font depict the sequence of C1s used as the target sequence. Underlined nucleotides indicate deleted nucleotides.

FIG. 16. CRISPR/Cas9 engineering of a protease-deficient CHO cell line. Proteolysis of Bal gp120 in $MGAT1^-$ CHO cell line vs. expression of gp120 in C1s knockout $MGAT1^-$ CHO cell line.

What is claimed is:

1. A genetically modified mammalian cell line comprising: a deletion in an endogenous c1s gene encoding a calcium-dependent serine (C1s) protease, wherein the deletion decreases calcium-dependent serine protease activity of the C1s protease, wherein the deletion consists of a deletion of (i) nucleotides 1448-1451 or (ii) nucleotides at positions 1444-1445 and 1447 with reference to wild type c1s mRNA sequence set forth in SEQ ID NO:4; and a heterologous nucleic acid comprising a nucleotide sequence encoding a gp120 polypeptide, wherein the gp120 polypeptide comprises a cleavage site for the C1s protease.

2. The genetically modified mammalian cell line of claim 1, wherein the gp120 polypeptide is a HIV-1 Clade B polypeptide.

3. The genetically modified mammalian cell line of claim 1, further comprising a mutation of an endogenous gene encoding mannosyl (alpha-1,3)-glycoprotein beta-1,2-N-Acetylglucosaminyltransferase (Mgat1), wherein the mutation prevents Mgat1-mediated addition of a N-acetylglucosamine moiety to a terminal mannose residue present at a N-linked glycosylation site of the gp120 polypeptide such that at least 75% of the gp120 polypeptide produced by the genetically modified mammalian cell line comprise terminal mannose-5, mannose-8, or mannose-9 glycans at the N-linked glycosylation site.

4. The genetically modified mammalian cell line of claim 1, wherein the gp120 polypeptide is fused to a heterologous signal sequence.

5. The genetically modified mammalian cell line of claim 4, wherein the heterologous signal sequence comprises the amino acid sequence of herpes simplex virus I glycoprotein D signal sequence (gD-1 ss) set forth in SEQ ID NO:44, fruit bat herpes simplex virus glycoprotein D signal sequence (FBgD-1 ss) set forth in SEQ ID NO:45, intracellular adhesion molecule signal sequence (ICAM-1 ss) set forth in SEQ ID NO:46, or tissue plasminogen activator signal sequence (TPA ss) set forth in SEQ ID NO: 47.

6. The genetically modified mammalian cell line of claim 1, wherein the gp120 polypeptide comprises a purification tag.

7. The genetically modified mammalian cell line of claim 6, wherein the purification tag comprises the amino acid sequence of gD-1 tag set forth in SEQ ID NO:48, FBgD-1 tag set forth in SEQ ID NO: 49, HIV gp120 tag set forth in-SEQ ID NO:50, 6×His tag, Avi tag set forth in ID NO: 52, Strep-Tactin (Strep) tag set forth in SEQ ID NO:53; His-Strep tag set forth in SEQ ID NO: 54, His-Strep-6×His tag (C-terminus) set forth in SEQ ID NO:55 or His-Strep-His (HSH) tag (N-terminus) set forth in SEQ ID NO:56.

8. The genetically modified mammalian cell line of claim 1, wherein the cell line is a Chinese hamster ovary (CHO) cell line.

9. The genetically modified mammalian cell line of claim 1, wherein the cell line is a CHO-K1 cell line.

10. The genetically modified mammalian cell line of claim 1, wherein the cell line is a CHO-S cell line.

11. The genetically modified mammalian cell line of claim 1, wherein the cell line comprises an endogenous gene encoding a glutamine synthetase (GS).

12. The genetically modified mammalian cell line of claim 1, wherein the cell line comprises an endogenous gene encoding a dihydrofolate reductase (DHFR).

13. A method of producing uncleaved gp120 polypeptide, the method comprising: culturing the cell line of claim 1 in a liquid culture medium under conditions sufficient for production of the gp120 polypeptide, wherein at least 50% of the gp120 polypeptide produced by the cell line is uncleaved.

14. The method of claim 13, wherein the gp120 polypeptide is fused to a heterologous signal sequence.

15. The method of claim 14, wherein the heterologous signal sequence comprises the amino acid sequence of herpes simplex virus I glycoprotein D signal sequence (gD-1 ss) set forth in SEQ ID NO:44, fruit bat herpes simplex virus glycoprotein D signal sequence (FBgD-1 ss) set forth in SEQ ID NO:45, intracellular adhesion molecule signal sequence (ICAM-1 ss) set forth in SEQ ID NO:46, or tissue plasminogen activator signal sequence (TPA ss) set forth in SEQ ID NO:47.

16. The method of claim 13, wherein the polypeptide comprises a purification tag.

17. The method of claim 16, wherein the purification tag comprises the amino acid sequence gD-1 tag set forth in SEQ ID NO:48, FBgD-1 tag set forth in SEQ ID NO:49, HIV gp120 tag set forth in SEQ ID NO:50, 6×His tag, Avi tag set forth in SEQ ID NO:52, Strep-Tactin (Strep) tag set forth in SEQ ID NO: 53; His-Strep tag set forth in SEQ ID NO: 54, His-Strep-6×His tag (C-terminus) set forth in SEQ ID NO: 55 or His-Strep-His (HSH) tag (N-terminus) set forth in SEQ ID NO:56.

18. The genetically modified mammalian cell line of claim 1, wherein the deletion consists of the deletion of nucleotides 1448-1451.

19. The genetically modified mammalian cell line of claim 1, wherein the deletion consists of the deletion of nucleotides at positions 1444-1445 and 1447.

* * * * *

SEQUENCE LISTING

```
<160> NUMBER OF SEQ ID NOS: 58

<210> SEQ ID NO 1
<211> LENGTH: 472
<212> TYPE: PRT
<213> ORGANISM: Artificial sequence
<220> FEATURE:
<223> OTHER INFORMATION: synthetic sequence

<400> SEQUENCE: 1

Val Pro Val Trp Lys Glu Ala Asp Thr Thr Leu Phe Cys Ala Ser Asp
1               5                   10                  15

Ala Lys Ala His Glu Thr Glu Val His Asn Val Trp Ala Thr His Ala
            20                  25                  30

Cys Val Pro Thr Asp Pro Asn Pro Gln Glu Ile Asp Leu Glu Asn Val
```

-continued

```
        35                  40                  45

Thr Glu Asn Phe Asn Met Trp Lys Asn Asn Met Val Glu Gln Met Gln
    50                  55                  60

Glu Asp Val Ile Ser Leu Trp Asp Gln Ser Leu Lys Pro Cys Val Lys
65                  70                  75                  80

Leu Thr Pro Pro Cys Val Thr Leu His Cys Thr Asn Ala Asn Leu Thr
                85                  90                  95

Lys Ala Asn Leu Thr Asn Val Asn Asn Arg Thr Asn Val Ser Asn Ile
            100                 105                 110

Ile Gly Asn Ile Thr Asp Glu Val Arg Asn Cys Ser Phe Asn Met Thr
        115                 120                 125

Thr Glu Leu Arg Asp Lys Lys Gln Lys Val His Ala Leu Phe Tyr Lys
    130                 135                 140

Leu Asp Ile Val Pro Ile Glu Asp Asn Asn Asp Ser Ser Glu Tyr Arg
145                 150                 155                 160

Leu Ile Asn Cys Asn Thr Ser Val Ile Lys Gln Ala Cys Pro Lys Ile
                165                 170                 175

Ser Phe Asp Pro Ile Pro Ile His Tyr Cys Thr Pro Ala Gly Tyr Ala
            180                 185                 190

Ile Leu Lys Cys Asn Asp Lys Asn Phe Asn Gly Thr Gly Pro Cys Lys
        195                 200                 205

Asn Val Ser Ser Val Gln Cys Thr His Gly Ile Lys Pro Val Val Ser
    210                 215                 220

Thr Gln Leu Leu Leu Asn Gly Ser Leu Ala Glu Glu Glu Ile Ile Ile
225                 230                 235                 240

Arg Ser Glu Asn Leu Thr Asn Asn Ala Lys Thr Ile Ile Val His Leu
                245                 250                 255

Asn Lys Ser Val Val Ile Asn Cys Thr Arg Pro Ser Asn Asn Thr Arg
            260                 265                 270

Thr Ser Ile Thr Ile Gly Pro Gly Gln Val Phe Tyr Arg Thr Gly Asp
        275                 280                 285

Ile Ile Gly Asp Ile Arg Lys Ala Tyr Cys Asn Ile Ser Gly Thr Glu
    290                 295                 300

Trp Asn Lys Ala Leu Lys Gln Val Thr Glu Lys Leu Lys Glu His Phe
305                 310                 315                 320

Asn Asn Lys Pro Ile Ile Phe Gln Pro Pro Ser Gly Gly Asp Leu Glu
                325                 330                 335

Ile Thr Met His His Phe Asn Cys Arg Gly Glu Phe Phe Tyr Cys Asn
            340                 345                 350

Thr Thr Arg Leu Phe Asn Asn Thr Cys Ile Ala Asn Gly Thr Ile Glu
        355                 360                 365

Gly Cys Asn Gly Asn Ile Thr Leu Pro Cys Lys Ile Lys Gln Ile Ile
    370                 375                 380

Asn Met Trp Gln Gly Ala Gly Gln Ala Met Tyr Ala Pro Pro Ile Ser
385                 390                 395                 400

Gly Thr Ile Asn Cys Val Ser Asn Ile Thr Gly Ile Leu Leu Thr Arg
                405                 410                 415

Asp Gly Gly Ala Thr Asn Asn Thr Asn Asn Glu Thr Phe Arg Pro Gly
            420                 425                 430

Gly Gly Asn Ile Lys Asp Asn Trp Arg Asn Glu Leu Tyr Lys Tyr Lys
        435                 440                 445

Val Val Gln Ile Glu Pro Leu Gly Val Ala Pro Thr Arg Ala Lys Arg
    450                 455                 460
```

Arg Val Val Glu Arg Glu Lys Arg
465 470

<210> SEQ ID NO 2
<211> LENGTH: 462
<212> TYPE: PRT
<213> ORGANISM: Artificial sequence
<220> FEATURE:
<223> OTHER INFORMATION: synthetic sequence

<400> SEQUENCE: 2

Val Pro Val Trp Lys Glu Ala Asp Thr Thr Leu Phe Cys Ala Ser Asp
1 5 10 15

Ala Lys Ala His Glu Thr Glu Val His Asn Val Trp Ala Thr His Ala
20 25 30

Cys Val Pro Thr Asp Pro Asn Pro Gln Glu Ile Asp Leu Glu Asn Val
35 40 45

Thr Glu Asn Phe Asn Met Trp Lys Asn Asn Met Val Glu Gln Met Gln
50 55 60

Glu Asp Val Ile Ser Leu Trp Asp Gln Ser Leu Lys Pro Cys Val Lys
65 70 75 80

Leu Thr Pro Pro Cys Val Thr Leu His Cys Thr Asn Ala Asn Leu Thr
85 90 95

Lys Ala Asn Leu Thr Asn Val Asn Asn Arg Thr Asn Val Ser Asn Ile
100 105 110

Ile Gly Asn Ile Thr Asp Glu Val Arg Asn Cys Ser Phe Asn Met Thr
115 120 125

Thr Glu Leu Arg Asp Lys Lys Gln Lys Val His Ala Leu Phe Tyr Lys
130 135 140

Leu Asp Ile Val Pro Ile Glu Asp Asn Asn Asp Ser Ser Glu Tyr Arg
145 150 155 160

Leu Ile Asn Cys Asn Thr Ser Val Ile Lys Gln Ala Cys Pro Lys Ile
165 170 175

Ser Phe Asp Pro Ile Pro Ile His Tyr Cys Thr Pro Ala Gly Tyr Ala
180 185 190

Ile Leu Lys Cys Asn Asp Lys Asn Phe Asn Gly Thr Gly Pro Cys Lys
195 200 205

Asn Val Ser Ser Val Gln Cys Thr His Gly Ile Lys Pro Val Val Ser
210 215 220

Thr Gln Leu Leu Leu Asn Gly Ser Leu Ala Glu Glu Glu Ile Ile Ile
225 230 235 240

Arg Ser Glu Asn Leu Thr Asn Asn Ala Lys Thr Ile Ile Val His Leu
245 250 255

Asn Lys Ser Val Val Ile Asn Cys Thr Arg Pro Ser Asn Asn Thr Arg
260 265 270

Thr Ser Ile Thr Ile Gly Pro Gly Gln Val Phe Tyr Arg Thr Gly Asp
275 280 285

Ile Ile Gly Asp Ile Arg Lys Ala Tyr Cys Asn Ile Ser Gly Thr Glu
290 295 300

Trp Asn Lys Ala Leu Lys Gln Val Thr Glu Lys Leu Lys Glu His Phe
305 310 315 320

Asn Asn Lys Pro Ile Ile Phe Gln Pro Pro Ser Gly Gly Asp Leu Glu
325 330 335

Ile Thr Met His His Phe Asn Cys Arg Gly Glu Phe Phe Tyr Cys Asn
340 345 350

```
Thr Thr Arg Leu Phe Asn Asn Thr Cys Ile Ala Asn Gly Thr Ile Glu
        355                 360                 365

Gly Cys Asn Gly Asn Ile Thr Leu Pro Cys Lys Ile Lys Gln Ile Ile
    370                 375                 380

Asn Met Trp Gln Gly Ala Gly Gln Ala Met Tyr Ala Pro Pro Ile Ser
385                 390                 395                 400

Gly Thr Ile Asn Cys Val Ser Asn Ile Thr Gly Ile Leu Leu Thr Arg
                405                 410                 415

Asp Gly Gly Ala Thr Asn Asn Thr Asn Asn Glu Thr Phe Arg Pro Gly
            420                 425                 430

Gly Gly Asn Ile Lys Asp Asn Trp Arg Asn Glu Leu Tyr Lys Tyr Lys
        435                 440                 445

Val Val Gln Ile Glu Pro Leu Gly Val Ala Pro Thr Arg Ala
    450                 455                 460


<210> SEQ ID NO 3
<211> LENGTH: 517
<212> TYPE: PRT
<213> ORGANISM: Artificial sequence
<220> FEATURE:
<223> OTHER INFORMATION: synthetic sequence

<400> SEQUENCE: 3

Met Gly Gly Ala Ala Ala Arg Leu Gly Ala Val Ile Leu Phe Val Val
1               5                   10                  15

Ile Val Gly Leu His Gly Val Arg Gly Lys Tyr Ala Leu Ala Asp Ala
            20                  25                  30

Ser Leu Lys Met Ala Asp Pro Asn Arg Phe Arg Gly Lys Asp Leu Pro
        35                  40                  45

Val Leu Asp Gln Leu Leu Glu Val Pro Val Trp Lys Glu Ala Asp Thr
    50                  55                  60

Thr Leu Phe Cys Ala Ser Asp Ala Lys Ala His Glu Thr Glu Val His
65                  70                  75                  80

Asn Val Trp Ala Thr His Ala Cys Val Pro Thr Asp Pro Asn Pro Gln
                85                  90                  95

Glu Ile Asp Leu Glu Asn Val Thr Glu Asn Phe Asn Met Trp Lys Asn
            100                 105                 110

Asn Met Val Glu Gln Met Gln Glu Asp Val Ile Ser Leu Trp Asp Gln
        115                 120                 125

Ser Leu Lys Pro Cys Val Lys Leu Thr Pro Pro Cys Val Thr Leu His
    130                 135                 140

Cys Thr Asn Ala Asn Leu Thr Lys Ala Asn Leu Thr Asn Val Asn Asn
145                 150                 155                 160

Arg Thr Asn Val Ser Asn Ile Ile Gly Asn Ile Thr Asp Glu Val Arg
                165                 170                 175

Asn Cys Ser Phe Asn Met Thr Thr Glu Leu Arg Asp Lys Lys Gln Lys
            180                 185                 190

Val His Ala Leu Phe Tyr Lys Leu Asp Ile Val Pro Ile Glu Asp Asn
        195                 200                 205

Asn Asp Ser Ser Glu Tyr Arg Leu Ile Asn Cys Asn Thr Ser Val Ile
    210                 215                 220

Lys Gln Ala Cys Pro Lys Ile Ser Phe Asp Pro Ile Pro Ile His Tyr
225                 230                 235                 240

Cys Thr Pro Ala Gly Tyr Ala Ile Leu Lys Cys Asn Asp Lys Asn Phe
                245                 250                 255
```

```
Asn Gly Thr Gly Pro Cys Lys Asn Val Ser Ser Val Gln Cys Thr His
            260                 265                 270

Gly Ile Lys Pro Val Val Ser Thr Gln Leu Leu Leu Asn Gly Ser Leu
        275                 280                 285

Ala Glu Glu Glu Ile Ile Ile Arg Ser Glu Asn Leu Thr Asn Asn Ala
    290                 295                 300

Lys Thr Ile Ile Val His Leu Asn Lys Ser Val Val Ile Asn Cys Thr
305                 310                 315                 320

Arg Pro Ser Asn Asn Thr Arg Thr Ser Ile Thr Ile Gly Pro Gly Gln
                325                 330                 335

Val Phe Tyr Arg Thr Gly Asp Ile Ile Gly Asp Ile Arg Lys Ala Tyr
            340                 345                 350

Cys Asn Ile Ser Gly Thr Glu Trp Asn Lys Ala Leu Lys Gln Val Thr
        355                 360                 365

Glu Lys Leu Lys Glu His Phe Asn Asn Lys Pro Ile Ile Phe Gln Pro
    370                 375                 380

Pro Ser Gly Gly Asp Leu Glu Ile Thr Met His His Phe Asn Cys Arg
385                 390                 395                 400

Gly Glu Phe Phe Tyr Cys Asn Thr Thr Arg Leu Phe Asn Asn Thr Cys
                405                 410                 415

Ile Ala Asn Gly Thr Ile Glu Gly Cys Asn Gly Asn Ile Thr Leu Pro
            420                 425                 430

Cys Lys Ile Lys Gln Ile Ile Asn Met Trp Gln Gly Ala Gly Gln Ala
        435                 440                 445

Met Tyr Ala Pro Pro Ile Ser Gly Thr Ile Asn Cys Val Ser Asn Ile
    450                 455                 460

Thr Gly Ile Leu Leu Thr Arg Asp Gly Gly Ala Thr Asn Asn Thr Asn
465                 470                 475                 480

Asn Glu Thr Phe Arg Pro Gly Gly Gly Asn Ile Lys Asp Asn Trp Arg
                485                 490                 495

Asn Glu Leu Tyr Lys Tyr Lys Val Val Gln Ile Glu Pro Leu Gly Val
            500                 505                 510

Ala Pro Thr Arg Ala
        515
```

<210> SEQ ID NO 4
<211> LENGTH: 2088
<212> TYPE: DNA
<213> ORGANISM: Cricetulus griseus

<400> SEQUENCE: 4

```
atgggcaaat caccagaggc atggtgcatt gtcttgtttt ctgttttggc atcattttct      60

gccgagccta ccatgcatgg ggagatcctg tcccctaact atcctcaggc gtaccccaat     120

gagatcgaga aaacgtggga catagaagtc ccagaagggt ttgggattcg cctctacttc     180

acccatctgg acatggagct gtcagagaac tgcgaatatg actcggtgca gataatctca     240

ggaggcgtcg aggaagggag actctgtggg cagaggacca gcaagaatgc caactccccc     300

attgtggaag agtttcaaat gccatacaat aaactccagg tgatctttag gtcagacttc     360

tccaacgaag agcggtttac tggctttgct gcatattacg ctgccgtaga tataaatgaa     420

tgcacagatt ttacagatgt cccttgcagc cacttctgca ataatttcat tggtggttac     480

ttctgctcct gtcccccaga atacttcctc cacgatgaca tgaggaactg cggagtcaat     540

tgtagtggga atgtattcac tgccctgatt ggggagattt caagccccaa ttatcccagt     600
```

```
ccataccccg agaactcaag gtgtgaatac cagattttgc tggaggaggg gttccaagtg    660
gtggtgacta tccggagaga agattttgat gtggaaccag ctgactcgga ggggaactgc    720
caggacagtt tactctttgc tgcaaaaaat caactatttg gtccttactg tggcaatggg    780
ttccctgggc cactaactat tgaaacccac agtaacactc ttgacattgt ctttcaaacg    840
gacctaacag agcaaagaaa aggctggaag cttcgttacc atggagaccc aatcccttgt    900
cccaaggaaa tcactgccaa ttctgtttgg gtgcctgaaa aggcaaaata tgtgtttaaa    960
gatgtggtga agatatcctg tgtggacgga tttgaagttg tagagggaaa tgttggctca   1020
gcattcttct attctacttg tcaaagcaat ggacagtgga gtaattccag actacaatgt   1080
cagcctgtgg actgtggtat tccggaaccc attcagaatg gtaaagttga cgatccagaa   1140
aacactgtgt ttggctctgt catccagtac tcgtgcgagg agccatatta ctacatggaa   1200
catgaagaac acggcgggga gtatcgctgc gctgctaatg ggagctgggt gaatgacgaa   1260
ctgggcatag agctcccaaa atgtgttcca gtctgtgggg tacccactga gcccattgca   1320
ttacagcaga ggatatttgg aggattccct gcaaagatcc agagttttcc ttggcaagtc   1380
ttctttgagt ccccacgggc cggtggggct cttattgacg agtactgggt gttgacagcc   1440
gctcatgttg tggagggaaa ctctgaccca tctatgtatg tggggaccac atttgtgaga   1500
atggaacatc tggcgaatgc ccagaggctc accgctgaac gtgtgattat tcatccaggc   1560
tggaagccag cggatgacct agaaacacgg acaaattttg acaatgacat tgcactggtg   1620
cagctgaaag accccgtgaa aatggggccc actgtctccc ccatctgcct gccaggtacc   1680
tcctcagagt acaacccctc aaagaatgac ctgggactga tctcagggtg gggccgaaca   1740
gagaagagaa atattgttcc ccaactcaaa ggggcaaagt tacctgtgac ctctttagag   1800
aagtgccaac aggtgaaagg ggagaactcc aaagtgaggg cggatgacta cgttttcacc   1860
agcaacatga tctgtgctgg agagaaaggt gttgatagct gtcaggggga cagtggtggg   1920
gcttttgctt tgcaggtccc caatgtaaag gaccccaaat tctatgtggc aggcctagtg   1980
tcctggggga aaaagtgtgg gacctatgga atctacacaa aggtaaagaa ctacatggat   2040
tggatcgtga agacgatgca ggagaatagt gtccccagta aggactaa                2088
```

<210> SEQ ID NO 5
<211> LENGTH: 684
<212> TYPE: PRT
<213> ORGANISM: Cricetulus griseus

<400> SEQUENCE: 5

```
Met Arg Val Lys Glu Thr Gln Met Asn Trp Pro Asn Leu Trp Lys Trp
1               5                   10                  15

Gly Thr Leu Ile Leu Gly Leu Val Ile Ile Cys Ser Ala Ser Asp Asn
            20                  25                  30

Leu Trp Val Thr Val Tyr Tyr Gly Val Pro Val Trp Lys Glu Ala Asp
        35                  40                  45

Thr Thr Leu Phe Cys Ala Ser Asp Ala Lys Ala His Glu Thr Glu Val
    50                  55                  60

His Asn Val Trp Ala Thr His Ala Cys Val Pro Thr Asp Pro Asn Pro
65                  70                  75                  80

Gln Glu Ile Asp Leu Glu Asn Val Thr Glu Asn Phe Asn Met Trp Lys
                85                  90                  95

Asn Asn Met Val Glu Gln Met Gln Glu Asp Val Ile Ser Leu Trp Asp
            100                 105                 110
```

-continued

```
Gln Ser Leu Lys Pro Cys Val Lys Leu Thr Pro Leu Cys Val Thr Leu
        115                 120                 125

His Cys Thr Asn Ala Asn Leu Thr Lys Ala Asn Leu Thr Asn Val Asn
    130                 135                 140

Asn Arg Thr Asn Val Ser Asn Ile Ile Gly Asn Ile Thr Asp Glu Val
145                 150                 155                 160

Arg Asn Cys Ser Phe Asn Met Thr Thr Glu Leu Arg Asp Lys Lys Gln
                165                 170                 175

Lys Val His Ala Leu Phe Tyr Lys Leu Asp Ile Val Pro Ile Glu Asp
            180                 185                 190

Asn Asn Asp Ser Ser Glu Tyr Arg Leu Ile Asn Cys Asn Thr Ser Val
        195                 200                 205

Ile Lys Gln Ala Cys Pro Lys Ile Ser Phe Asp Pro Ile Pro Ile His
    210                 215                 220

Tyr Cys Thr Pro Ala Gly Tyr Ala Ile Leu Lys Cys Asn Asp Lys Asn
225                 230                 235                 240

Phe Asn Gly Thr Gly Pro Cys Lys Asn Val Ser Ser Val Gln Cys Thr
                245                 250                 255

His Gly Ile Lys Pro Val Val Ser Thr Gln Leu Leu Leu Asn Gly Ser
            260                 265                 270

Leu Ala Glu Glu Glu Ile Ile Ile Arg Ser Asp Asn Leu Thr Asn Asn
        275                 280                 285

Ala Lys Thr Ile Ile Val His Leu Asn Lys Ser Val Val Ile Asn Cys
    290                 295                 300

Thr Arg Pro Ser Asn Asn Thr Arg Thr Ser Ile Thr Ile Gly Pro Gly
305                 310                 315                 320

Gln Val Phe Tyr Arg Thr Gly Asp Ile Ile Gly Asp Ile Arg Lys Ala
                325                 330                 335

Tyr Cys Glu Ile Asn Gly Thr Glu Trp Asn Lys Ala Leu Lys Gln Val
            340                 345                 350

Thr Glu Lys Leu Lys Glu His Phe Asn Asn Lys Pro Ile Ile Phe Gln
        355                 360                 365

Pro Pro Ser Gly Gly Asp Leu Glu Ile Thr Met His His Phe Asn Cys
    370                 375                 380

Arg Gly Glu Phe Phe Tyr Cys Asn Thr Thr Arg Leu Phe Asn Asn Thr
385                 390                 395                 400

Cys Ile Ala Asn Gly Thr Ile Glu Gly Cys Asn Gly Asn Ile Thr Leu
                405                 410                 415

Pro Cys Lys Ile Lys Gln Ile Ile Asn Met Trp Gln Gly Ala Gly Gln
            420                 425                 430

Ala Met Tyr Ala Pro Pro Ile Ser Gly Thr Ile Asn Cys Val Ser Asn
        435                 440                 445

Ile Thr Gly Ile Leu Leu Thr Arg Asp Gly Gly Ala Thr Asn Asn Thr
    450                 455                 460

Asn Asn Glu Thr Phe Arg Pro Gly Gly Gly Asn Ile Lys Asp Asn Trp
465                 470                 475                 480

Arg Asn Glu Leu Tyr Lys Tyr Lys Val Val Gln Ile Glu Pro Leu Gly
                485                 490                 495

Val Ala Pro Thr Arg Ala Lys Arg Arg Val Val Glu Arg Glu Lys Arg
            500                 505                 510

Ala Val Gly Ile Gly Ala Met Ile Phe Gly Phe Leu Gly Ala Ala Gly
        515                 520                 525
```

```
Ser Thr Met Gly Ala Ala Ser Ile Thr Leu Thr Val Gln Ala Arg Gln
    530                 535                 540

Leu Leu Ser Gly Ile Val Gln Gln Gln Ser Asn Leu Leu Arg Ala Ile
545                 550                 555                 560

Glu Ala Gln Gln His Leu Leu Gln Leu Thr Val Trp Gly Ile Lys Gln
                565                 570                 575

Leu Gln Ala Arg Val Leu Ala Val Glu Arg Tyr Leu Lys Asp Gln Lys
            580                 585                 590

Phe Leu Gly Leu Trp Gly Cys Ser Gly Lys Ile Ile Cys Thr Thr Ala
        595                 600                 605

Val Pro Trp Asn Ser Thr Trp Ser Asn Lys Ser Leu Glu Glu Ile Trp
    610                 615                 620

Ser Asn Met Thr Trp Ile Glu Trp Glu Arg Glu Ile Ser Asn Tyr Thr
625                 630                 635                 640

Asn Gln Ile Tyr Glu Ile Leu Thr Lys Ser Gln Asp Gln Gln Asp Arg
                645                 650                 655

Asn Glu Lys Asp Leu Leu Glu Leu Asp Lys Trp Ala Ser Leu Trp Thr
            660                 665                 670

Trp Phe Asp Ile Thr Asn Trp Leu Trp Tyr Ile Lys
        675                 680


<210> SEQ ID NO 6
<211> LENGTH: 695
<212> TYPE: PRT
<213> ORGANISM: Artificial sequence
<220> FEATURE:
<223> OTHER INFORMATION: synthetic sequence

<400> SEQUENCE: 6

Met Gly Lys Ser Pro Glu Ala Trp Cys Ile Val Leu Phe Ser Val Leu
1               5                   10                  15

Ala Ser Phe Ser Ala Glu Pro Thr Met His Gly Glu Ile Leu Ser Pro
            20                  25                  30

Asn Tyr Pro Gln Ala Tyr Pro Asn Glu Ile Glu Lys Thr Trp Asp Ile
        35                  40                  45

Glu Val Pro Glu Gly Phe Gly Ile Arg Leu Tyr Phe Thr His Leu Asp
    50                  55                  60

Met Glu Leu Ser Glu Asn Cys Glu Tyr Asp Ser Val Gln Ile Ile Ser
65                  70                  75                  80

Gly Gly Val Glu Glu Gly Arg Leu Cys Gly Gln Arg Thr Ser Lys Asn
                85                  90                  95

Ala Asn Ser Pro Ile Val Glu Glu Phe Gln Met Pro Tyr Asn Lys Leu
            100                 105                 110

Gln Val Ile Phe Arg Ser Asp Phe Ser Asn Glu Glu Arg Phe Thr Gly
        115                 120                 125

Phe Ala Ala Tyr Tyr Ala Ala Val Asp Ile Asn Glu Cys Thr Asp Phe
    130                 135                 140

Thr Asp Val Pro Cys Ser His Phe Cys Asn Asn Phe Ile Gly Gly Tyr
145                 150                 155                 160

Phe Cys Ser Cys Pro Pro Glu Tyr Phe Leu His Asp Asp Met Arg Asn
                165                 170                 175

Cys Gly Val Asn Cys Ser Gly Asn Val Phe Thr Ala Leu Ile Gly Glu
            180                 185                 190

Ile Ser Ser Pro Asn Tyr Pro Ser Pro Tyr Pro Glu Asn Ser Arg Cys
        195                 200                 205
```

-continued

```
Glu Tyr Gln Ile Leu Leu Glu Glu Gly Phe Gln Val Val Val Thr Ile
    210                 215                 220

Arg Arg Glu Asp Phe Asp Val Glu Pro Ala Asp Ser Glu Gly Asn Cys
225                 230                 235                 240

Gln Asp Ser Leu Leu Phe Ala Ala Lys Asn Gln Leu Phe Gly Pro Tyr
                245                 250                 255

Cys Gly Asn Gly Phe Pro Gly Pro Leu Thr Ile Glu Thr His Ser Asn
            260                 265                 270

Thr Leu Asp Ile Val Phe Gln Thr Asp Leu Thr Glu Gln Arg Lys Gly
        275                 280                 285

Trp Lys Leu Arg Tyr His Gly Asp Pro Ile Pro Cys Pro Lys Glu Ile
    290                 295                 300

Thr Ala Asn Ser Val Trp Val Pro Glu Lys Ala Lys Tyr Val Phe Lys
305                 310                 315                 320

Asp Val Val Lys Ile Ser Cys Val Asp Gly Phe Glu Val Val Glu Gly
                325                 330                 335

Asn Val Gly Ser Ala Phe Phe Tyr Ser Thr Cys Gln Ser Asn Gly Gln
            340                 345                 350

Trp Ser Asn Ser Arg Leu Gln Cys Gln Pro Val Asp Cys Gly Ile Pro
        355                 360                 365

Glu Pro Ile Gln Asn Gly Lys Val Asp Asp Pro Glu Asn Thr Val Phe
    370                 375                 380

Gly Ser Val Ile Gln Tyr Ser Cys Glu Glu Pro Tyr Tyr Tyr Met Glu
385                 390                 395                 400

His Glu Glu His Gly Gly Glu Tyr Arg Cys Ala Ala Asn Gly Ser Trp
                405                 410                 415

Val Asn Asp Glu Leu Gly Ile Glu Leu Pro Lys Cys Val Pro Val Cys
            420                 425                 430

Gly Val Pro Thr Glu Pro Ile Ala Leu Gln Gln Arg Ile Phe Gly Gly
        435                 440                 445

Phe Pro Ala Lys Ile Gln Ser Phe Pro Trp Gln Val Phe Phe Glu Ser
    450                 455                 460

Pro Arg Ala Gly Gly Ala Leu Ile Asp Glu Tyr Trp Val Leu Thr Ala
465                 470                 475                 480

Ala His Val Val Glu Gly Asn Ser Asp Pro Ser Met Tyr Val Gly Thr
                485                 490                 495

Thr Phe Val Arg Met Glu His Leu Ala Asn Ala Gln Arg Leu Thr Ala
            500                 505                 510

Glu Arg Val Ile Ile His Pro Gly Trp Lys Pro Ala Asp Asp Leu Glu
        515                 520                 525

Thr Arg Thr Asn Phe Asp Asn Asp Ile Ala Leu Val Gln Leu Lys Asp
    530                 535                 540

Pro Val Lys Met Gly Pro Thr Val Ser Pro Ile Cys Leu Pro Gly Thr
545                 550                 555                 560

Ser Ser Glu Tyr Asn Pro Ser Lys Asn Asp Leu Gly Leu Ile Ser Gly
                565                 570                 575

Trp Gly Arg Thr Glu Lys Arg Asn Ile Val Pro Gln Leu Lys Gly Ala
            580                 585                 590

Lys Leu Pro Val Thr Ser Leu Glu Lys Cys Gln Gln Val Lys Gly Glu
        595                 600                 605

Asn Ser Lys Val Arg Ala Asp Asp Tyr Val Phe Thr Ser Asn Met Ile
    610                 615                 620

Cys Ala Gly Glu Lys Gly Val Asp Ser Cys Gln Gly Asp Ser Gly Gly
```

```
625                 630                 635                 640

Ala Phe Ala Leu Gln Val Pro Asn Val Lys Asp Pro Lys Phe Tyr Val
                645                 650                 655

Ala Gly Leu Val Ser Trp Gly Lys Lys Cys Gly Thr Tyr Gly Ile Tyr
            660                 665                 670

Thr Lys Val Lys Asn Tyr Met Asp Trp Ile Val Lys Thr Met Gln Glu
        675                 680                 685

Asn Ser Val Pro Ser Lys Asp
    690                 695


<210> SEQ ID NO 7
<211> LENGTH: 684
<212> TYPE: PRT
<213> ORGANISM: Artificial sequence
<220> FEATURE:
<223> OTHER INFORMATION: synthetic sequence

<400> SEQUENCE: 7

Met Arg Val Lys Glu Thr Gln Met Asn Trp Pro Asn Leu Trp Lys Trp
1               5                   10                  15

Gly Thr Leu Ile Leu Gly Leu Val Ile Ile Cys Ser Ala Ser Asp Asn
            20                  25                  30

Leu Trp Val Thr Val Tyr Tyr Gly Val Pro Val Trp Lys Glu Ala Asp
        35                  40                  45

Thr Thr Leu Phe Cys Ala Ser Asp Ala Lys Ala His Glu Thr Glu Val
    50                  55                  60

His Asn Val Trp Ala Thr His Ala Cys Val Pro Thr Asp Pro Asn Pro
65                  70                  75                  80

Gln Glu Ile Asp Leu Glu Asn Val Thr Glu Asn Phe Asn Met Trp Lys
                85                  90                  95

Asn Asn Met Val Glu Gln Met Gln Glu Asp Val Ile Ser Leu Trp Asp
            100                 105                 110

Gln Ser Leu Lys Pro Cys Val Lys Leu Thr Pro Leu Cys Val Thr Leu
        115                 120                 125

His Cys Thr Asn Ala Asn Leu Thr Lys Ala Asn Leu Thr Asn Val Asn
    130                 135                 140

Asn Arg Thr Asn Val Ser Asn Ile Ile Gly Asn Ile Thr Asp Glu Val
145                 150                 155                 160

Arg Asn Cys Ser Phe Asn Met Thr Thr Glu Leu Arg Asp Lys Lys Gln
                165                 170                 175

Lys Val His Ala Leu Phe Tyr Lys Leu Asp Ile Val Pro Ile Glu Asp
            180                 185                 190

Asn Asn Asp Ser Ser Glu Tyr Arg Leu Ile Asn Cys Asn Thr Ser Val
        195                 200                 205

Ile Lys Gln Ala Cys Pro Lys Ile Ser Phe Asp Pro Ile Pro Ile His
    210                 215                 220

Tyr Cys Thr Pro Ala Gly Tyr Ala Ile Leu Lys Cys Asn Asp Lys Asn
225                 230                 235                 240

Phe Asn Gly Thr Gly Pro Cys Lys Asn Val Ser Ser Val Gln Cys Thr
                245                 250                 255

His Gly Ile Lys Pro Val Val Ser Thr Gln Leu Leu Leu Asn Gly Ser
            260                 265                 270

Leu Ala Glu Glu Glu Ile Ile Ile Arg Ser Asp Asn Leu Thr Asn Asn
        275                 280                 285

Ala Lys Thr Ile Ile Val His Leu Asn Lys Ser Val Val Ile Asn Cys
```

```
    290                 295                 300

Thr Arg Pro Ser Asn Asn Thr Arg Thr Ser Ile Thr Ile Gly Pro Gly
305                 310                 315                 320

Gln Val Phe Tyr Arg Thr Gly Asp Ile Ile Gly Asp Ile Arg Lys Ala
                325                 330                 335

Tyr Cys Asn Ile Ser Gly Thr Glu Trp Asn Lys Ala Leu Lys Gln Val
            340                 345                 350

Thr Glu Lys Leu Lys Glu His Phe Asn Asn Lys Pro Ile Ile Phe Gln
        355                 360                 365

Pro Pro Ser Gly Gly Asp Leu Glu Ile Thr Met His His Phe Asn Cys
    370                 375                 380

Arg Gly Glu Phe Phe Tyr Cys Asn Thr Thr Arg Leu Phe Asn Asn Thr
385                 390                 395                 400

Cys Ile Ala Asn Gly Thr Ile Glu Gly Cys Asn Gly Asn Ile Thr Leu
                405                 410                 415

Pro Cys Lys Ile Lys Gln Ile Ile Asn Met Trp Gln Gly Ala Gly Gln
            420                 425                 430

Ala Met Tyr Ala Pro Pro Ile Ser Gly Thr Ile Asn Cys Val Ser Asn
        435                 440                 445

Ile Thr Gly Ile Leu Leu Thr Arg Asp Gly Gly Ala Thr Asn Asn Thr
    450                 455                 460

Asn Asn Glu Thr Phe Arg Pro Gly Gly Gly Asn Ile Lys Asp Asn Trp
465                 470                 475                 480

Arg Asn Glu Leu Tyr Lys Tyr Lys Val Val Gln Ile Glu Pro Leu Gly
                485                 490                 495

Val Ala Pro Thr Arg Ala Lys Arg Arg Val Val Glu Arg Glu Lys Arg
            500                 505                 510

Ala Val Gly Ile Gly Ala Met Ile Phe Gly Phe Leu Gly Ala Ala Gly
        515                 520                 525

Ser Thr Met Gly Ala Ala Ser Ile Thr Leu Thr Val Gln Ala Arg Gln
    530                 535                 540

Leu Leu Ser Gly Ile Val Gln Gln Gln Ser Asn Leu Leu Arg Ala Ile
545                 550                 555                 560

Glu Ala Gln Gln His Leu Leu Gln Leu Thr Val Trp Gly Ile Lys Gln
                565                 570                 575

Leu Gln Ala Arg Val Leu Ala Val Glu Arg Tyr Leu Lys Asp Gln Lys
            580                 585                 590

Phe Leu Gly Leu Trp Gly Cys Ser Gly Lys Ile Ile Cys Thr Thr Ala
        595                 600                 605

Val Pro Trp Asn Ser Thr Trp Ser Asn Lys Ser Leu Glu Glu Ile Trp
    610                 615                 620

Ser Asn Met Thr Trp Ile Glu Trp Glu Arg Glu Ile Ser Asn Tyr Thr
625                 630                 635                 640

Asn Gln Ile Tyr Glu Ile Leu Thr Lys Ser Gln Asp Gln Gln Asp Arg
                645                 650                 655

Asn Glu Lys Asp Leu Leu Glu Leu Asp Lys Trp Ala Ser Leu Trp Thr
            660                 665                 670

Trp Phe Asp Ile Thr Asn Trp Leu Trp Tyr Ile Lys
        675                 680
```

<210> SEQ ID NO 8
<211> LENGTH: 2084
<212> TYPE: DNA
<213> ORGANISM: Artificial sequence
<220> FEATURE:
<223> OTHER INFORMATION: synthetic sequence

<400> SEQUENCE: 8

```
atgggcaaat caccagaggc atggtgcatt gtcttgtttt ctgttttggc atcattttct     60
gccgagccta ccatgcatgg ggagatcctg tcccctaact atcctcaggc gtaccccaat    120
gagatcgaga aaacgtggga catagaagtc ccagaagggt ttgggattcg cctctacttc    180
acccatctgg acatggagct gtcagagaac tgcgaatatg actcggtgca gataatctca    240
ggaggcgtcg aggaagggag actctgtggg cagaggacca gcaagaatgc caactccccc    300
attgtggaag agtttcaaat gccatacaat aaactccagg tgatctttag gtcagacttc    360
tccaacgaag agcggtttac tggctttgct gcatattacg ctgccgtaga tataaatgaa    420
tgcacagatt ttacagatgt cccttgcagc cacttctgca ataatttcat tggtggttac    480
ttctgctcct gtcccccaga atacttcctc cacgatgaca tgaggaactg cggagtcaat    540
tgtagtggga atgtattcac tgccctgatt ggggagattt caagccccaa ttatcccagt    600
ccataccccg agaactcaag gtgtgaatac cagattttgc tggaggaggg gttccaagtg    660
gtggtgacta tccggagaga agattttgat gtggaaccag ctgactcgga ggggaactgc    720
caggacagtt tactctttgc tgcaaaaaat caactatttg gtccttactg tggcaatggg    780
ttccctgggc cactaactat tgaaacccac agtaacactc ttgacattgt ctttcaaacg    840
gacctaacag agcaaagaaa aggctggaag cttcgttacc atggagaccc aatcccttgt    900
cccaaggaaa tcactgccaa ttctgtttgg gtgcctgaaa aggcaaaata tgtgtttaaa    960
gatgtggtga agatatcctg tgtggacgga tttgaagttg tagagggaaa tgttggctca   1020
gcattcttct attctacttg tcaaagcaat ggacagtgga gtaattccag actacaatgt   1080
cagcctgtgg actgtggtat tccggaaccc attcagaatg gtaaagttga cgatccagaa   1140
aacactgtgt ttggctctgt catccagtac tcgtgcgagg agccatatta ctacatggaa   1200
catgaagaac acggcgggga gtatcgctgc gctgctaatg ggagctgggt gaatgacgaa   1260
ctgggcatag agctcccaaa atgtgttcca gtctgtgggg tacccactga gcccattgca   1320
ttacagcaga ggatatttgg aggattccct gcaaagatcc agagttttcc ttggcaagtc   1380
ttctttgagt ccccacgggc cggtggggct cttattgacg agtactgggt gttgacagcc   1440
gctcatggga gggaaactct gacccatcta tgtatgtggg gaccacattt gtgagaatgg   1500
aacatctggc gaatgcccag aggctcaccg ctgaacgtgt gattattcat ccaggctgga   1560
agccagcgga tgacctagaa acacggacaa attttgacaa tgacattgca ctggtgcagc   1620
tgaaagaccc cgtgaaaatg ggccccactg tctcccccat ctgcctgcca ggtacctcct   1680
cagagtacaa cccctcaaag aatgacctgg gactgatctc agggtggggc cgaacagaga   1740
agagaaatat tgttccccaa ctcaaagggg caaagttacc tgtgacctct ttagagaagt   1800
gccaacaggt gaaaggggag aactccaaag tgagggcgga tgactacgtt ttcaccagca   1860
acatgatctg tgctggagag aaaggtgttg atagctgtca gggggacagt ggtggggctt   1920
ttgctttgca ggtccccaat gtaaaggacc ccaaattcta tgtggcaggc ctagtgtcct   1980
gggggaaaaa gtgtgggacc tatggaatct acacaaaggt aaagaactac atggattgga   2040
tcgtgaagac gatgcaggag aatagtgtcc ccagtaagga ctaa                    2084
```

<210> SEQ ID NO 9
<211> LENGTH: 463
<212> TYPE: PRT

```
<213> ORGANISM: Artificial sequence
<220> FEATURE:
<223> OTHER INFORMATION: synthetic sequence
<220> FEATURE:
<221> NAME/KEY: misc_feature
<222> LOCATION: (191)..(191)
<223> OTHER INFORMATION: Xaa can be any naturally occurring amino acid

<400> SEQUENCE: 9

Val Pro Val Trp Lys Glu Ala Thr Thr Thr Leu Phe Cys Ala Ser Asp
1               5                   10                  15

Ala Lys Ala Tyr Asp Thr Glu Ala His Asn Val Trp Ala Thr His Ala
            20                  25                  30

Cys Val Pro Thr Asp Pro Asn Pro Gln Glu Val Glu Leu Val Asn Val
        35                  40                  45

Thr Glu Asn Phe Asn Met Trp Lys Asn Asn Met Val Glu Gln Met His
    50                  55                  60

Glu Asp Ile Ile Ser Leu Trp Asp Gln Ser Leu Lys Pro Cys Val Lys
65                  70                  75                  80

Leu Thr Pro Leu Cys Val Thr Leu Asn Cys Thr Asp Leu Arg Asn Thr
                85                  90                  95

Thr Asn Thr Asn Asn Ser Thr Asp Asn Asn Asn Ser Lys Ser Glu Gly
            100                 105                 110

Thr Ile Lys Gly Gly Glu Met Lys Asn Cys Ser Phe Asn Ile Thr Thr
        115                 120                 125

Ser Ile Gly Asp Lys Met Gln Lys Glu Tyr Ala Leu Leu Tyr Lys Leu
    130                 135                 140

Asp Ile Glu Pro Ile Asp Asn Asp Ser Thr Ser Tyr Arg Leu Ile Ser
145                 150                 155                 160

Cys Asn Thr Ser Val Ile Thr Gln Ala Cys Pro Lys Ile Ser Phe Glu
                165                 170                 175

Pro Ile Pro Ile His Tyr Cys Ala Pro Ala Gly Phe Ala Ile Xaa Lys
            180                 185                 190

Cys Asn Asp Lys Lys Phe Ser Gly Lys Gly Ser Cys Lys Asn Val Ser
        195                 200                 205

Thr Val Gln Cys Thr His Gly Ile Arg Pro Val Val Ser Thr Gln Leu
    210                 215                 220

Leu Leu Asn Gly Ser Leu Ala Glu Glu Glu Val Val Ile Arg Ser Glu
225                 230                 235                 240

Asp Phe Thr Asp Asn Ala Lys Thr Ile Ile Val His Leu Asn Glu Ser
                245                 250                 255

Val Gln Ile Asn Cys Thr Arg Pro Asn Asn Asn Thr Arg Lys Arg Ile
            260                 265                 270

His Ile Gly Pro Gly Arg Ala Phe Tyr Thr Thr Lys Asn Ile Lys Gly
        275                 280                 285

Thr Ile Arg Gln Ala His Cys Asn Ile Ser Arg Ala Lys Trp Asn Asp
    290                 295                 300

Thr Leu Arg Gln Ile Val Ser Lys Leu Lys Glu Gln Phe Lys Asn Lys
305                 310                 315                 320

Thr Ile Val Phe Asn Pro Ser Ser Gly Gly Asp Pro Glu Ile Val Met
                325                 330                 335

His Ser Phe Asn Cys Gly Gly Glu Phe Phe Tyr Cys Asn Thr Ser Pro
            340                 345                 350

Leu Phe Asn Ser Ile Trp Asn Gly Asn Asn Thr Trp Asn Asn Thr Thr
        355                 360                 365
```

```
Gly Ser Asn Asn Asn Ile Thr Leu Gln Cys Lys Ile Lys Gln Ile Ile
    370                 375                 380

Asn Met Trp Gln Lys Val Gly Lys Ala Met Tyr Ala Pro Pro Ile Glu
385                 390                 395                 400

Gly Gln Ile Arg Cys Ser Ser Asn Ile Thr Gly Leu Leu Leu Thr Arg
                405                 410                 415

Asp Gly Gly Glu Asp Thr Asp Thr Asn Asp Thr Glu Ile Phe Arg Pro
            420                 425                 430

Gly Gly Gly Asp Met Arg Asp Asn Trp Arg Ser Glu Leu Tyr Lys Tyr
        435                 440                 445

Lys Val Val Thr Ile Glu Pro Leu Gly Val Ala Pro Thr Lys Ala
    450                 455                 460


<210> SEQ ID NO 10
<211> LENGTH: 526
<212> TYPE: PRT
<213> ORGANISM: Artificial sequence
<220> FEATURE:
<223> OTHER INFORMATION: synthetic sequence
<220> FEATURE:
<221> NAME/KEY: misc_feature
<222> LOCATION: (246)..(246)
<223> OTHER INFORMATION: Xaa can be any naturally occurring amino acid

<400> SEQUENCE: 10

Met Gly Gly Ala Ala Ala Arg Leu Gly Ala Val Ile Leu Phe Val Val
1               5                   10                  15

Ile Val Gly Leu His Gly Val Arg Gly Lys Tyr Ala Leu Ala Asp Ala
            20                  25                  30

Ser Leu Lys Met Ala Asp Pro Asn Arg Phe Arg Gly Lys Asp Leu Pro
        35                  40                  45

Val Leu Asp Gln Leu Leu Glu Val Pro Val Trp Lys Glu Ala Thr Thr
    50                  55                  60

Thr Leu Phe Cys Ala Ser Asp Ala Lys Ala Tyr Asp Thr Glu Ala His
65                  70                  75                  80

Asn Val Trp Ala Thr His Ala Cys Val Pro Thr Asp Pro Asn Pro Gln
                85                  90                  95

Glu Val Glu Leu Val Asn Val Thr Glu Asn Phe Asn Met Trp Lys Asn
            100                 105                 110

Asn Met Val Glu Gln Met His Glu Asp Ile Ile Ser Leu Trp Asp Gln
        115                 120                 125

Ser Leu Lys Pro Cys Val Lys Leu Thr Pro Leu Cys Val Thr Leu Asn
    130                 135                 140

Cys Thr Asp Leu Arg Asn Thr Thr Asn Thr Asn Asn Ser Thr Asp Asn
145                 150                 155                 160

Asn Asn Ser Lys Ser Glu Gly Thr Ile Lys Gly Gly Glu Met Lys Asn
                165                 170                 175

Cys Ser Phe Asn Ile Thr Thr Ser Ile Gly Asp Lys Met Gln Lys Glu
            180                 185                 190

Tyr Ala Leu Leu Tyr Lys Leu Asp Ile Glu Pro Ile Asp Asn Asp Ser
        195                 200                 205

Thr Ser Tyr Arg Leu Ile Ser Cys Asn Thr Ser Val Ile Thr Gln Ala
    210                 215                 220

Cys Pro Lys Ile Ser Phe Glu Pro Ile Pro Ile His Tyr Cys Ala Pro
225                 230                 235                 240

Ala Gly Phe Ala Ile Xaa Lys Cys Asn Asp Lys Lys Phe Ser Gly Lys
                245                 250                 255
```

-continued

Gly Ser Cys Lys Asn Val Ser Thr Val Gln Cys Thr His Gly Ile Arg
260 265 270

Pro Val Val Ser Thr Gln Leu Leu Leu Asn Gly Ser Leu Ala Glu Glu
275 280 285

Glu Val Val Ile Arg Ser Glu Asp Phe Thr Asp Asn Ala Lys Thr Ile
290 295 300

Ile Val His Leu Asn Glu Ser Val Gln Ile Asn Cys Thr Arg Pro Asn
305 310 315 320

Asn Asn Thr Arg Lys Arg Ile His Ile Gly Pro Gly Arg Ala Phe Tyr
325 330 335

Thr Thr Lys Asn Ile Lys Gly Thr Ile Arg Gln Ala His Cys Asn Ile
340 345 350

Ser Arg Ala Lys Trp Asn Asp Thr Leu Arg Gln Ile Val Ser Lys Leu
355 360 365

Lys Glu Gln Phe Lys Asn Lys Thr Ile Val Phe Asn Pro Ser Ser Gly
370 375 380

Gly Asp Pro Glu Ile Val Met His Ser Phe Asn Cys Gly Gly Glu Phe
385 390 395 400

Phe Tyr Cys Asn Thr Ser Pro Leu Phe Asn Ser Ile Trp Asn Gly Asn
405 410 415

Asn Thr Trp Asn Asn Thr Thr Gly Ser Asn Asn Asn Ile Thr Leu Gln
420 425 430

Cys Lys Ile Lys Gln Ile Ile Asn Met Trp Gln Lys Val Gly Lys Ala
435 440 445

Met Tyr Ala Pro Pro Ile Glu Gly Gln Ile Arg Cys Ser Ser Asn Ile
450 455 460

Thr Gly Leu Leu Leu Thr Arg Asp Gly Gly Glu Asp Thr Asp Thr Asn
465 470 475 480

Asp Thr Glu Ile Phe Arg Pro Gly Gly Gly Asp Met Arg Asp Asn Trp
485 490 495

Arg Ser Glu Leu Tyr Lys Tyr Lys Val Val Thr Ile Glu Pro Leu Gly
500 505 510

Val Ala Pro Thr Lys Ala Lys Arg Arg Val Val Gln Arg Glu
515 520 525

<210> SEQ ID NO 11
<211> LENGTH: 497
<212> TYPE: PRT
<213> ORGANISM: Artificial sequence
<220> FEATURE:
<223> OTHER INFORMATION: synthetic sequence

<400> SEQUENCE: 11

Met Gly Lys Ser Pro Glu Ala Trp Cys Ile Val Leu Phe Ser Val Leu
1 5 10 15

Ala Ser Phe Ser Ala Glu Pro Thr Met His Gly Glu Ile Leu Ser Pro
20 25 30

Asn Tyr Pro Gln Ala Tyr Pro Asn Glu Ile Glu Lys Thr Trp Asp Ile
35 40 45

Glu Val Pro Glu Gly Phe Gly Ile Arg Leu Tyr Phe Thr His Leu Asp
50 55 60

Met Glu Leu Ser Glu Asn Cys Glu Tyr Asp Ser Val Gln Ile Ile Ser
65 70 75 80

Gly Gly Val Glu Glu Gly Arg Leu Cys Gly Gln Arg Thr Ser Lys Asn
85 90 95

```
Ala Asn Ser Pro Ile Val Glu Glu Phe Gln Met Pro Tyr Asn Lys Leu
            100                 105                 110

Gln Val Ile Phe Arg Ser Asp Phe Ser Asn Glu Glu Arg Phe Thr Gly
        115                 120                 125

Phe Ala Ala Tyr Tyr Ala Ala Val Asp Ile Asn Glu Cys Thr Asp Phe
    130                 135                 140

Thr Asp Val Pro Cys Ser His Phe Cys Asn Asn Phe Ile Gly Gly Tyr
145                 150                 155                 160

Phe Cys Ser Cys Pro Pro Glu Tyr Phe Leu His Asp Asp Met Arg Asn
                165                 170                 175

Cys Gly Val Asn Cys Ser Gly Asn Val Phe Thr Ala Leu Ile Gly Glu
            180                 185                 190

Ile Ser Ser Pro Asn Tyr Pro Ser Pro Tyr Pro Glu Asn Ser Arg Cys
        195                 200                 205

Glu Tyr Gln Ile Leu Leu Glu Glu Gly Phe Gln Val Val Val Thr Ile
    210                 215                 220

Arg Arg Glu Asp Phe Asp Val Glu Pro Ala Asp Ser Glu Gly Asn Cys
225                 230                 235                 240

Gln Asp Ser Leu Leu Phe Ala Ala Lys Asn Gln Leu Phe Gly Pro Tyr
                245                 250                 255

Cys Gly Asn Gly Phe Pro Gly Pro Leu Thr Ile Glu Thr His Ser Asn
            260                 265                 270

Thr Leu Asp Ile Val Phe Gln Thr Asp Leu Thr Glu Gln Arg Lys Gly
        275                 280                 285

Trp Lys Leu Arg Tyr His Gly Asp Pro Ile Pro Cys Pro Lys Glu Ile
    290                 295                 300

Thr Ala Asn Ser Val Trp Val Pro Glu Lys Ala Lys Tyr Val Phe Lys
305                 310                 315                 320

Asp Val Val Lys Ile Ser Cys Val Asp Gly Phe Glu Val Val Glu Gly
                325                 330                 335

Asn Val Gly Ser Ala Phe Phe Tyr Ser Thr Cys Gln Ser Asn Gly Gln
            340                 345                 350

Trp Ser Asn Ser Arg Leu Gln Cys Gln Pro Val Asp Cys Gly Ile Pro
        355                 360                 365

Glu Pro Ile Gln Asn Gly Lys Val Asp Asp Pro Glu Asn Thr Val Phe
    370                 375                 380

Gly Ser Val Ile Gln Tyr Ser Cys Glu Glu Pro Tyr Tyr Tyr Met Glu
385                 390                 395                 400

His Glu Glu His Gly Gly Glu Tyr Arg Cys Ala Ala Asn Gly Ser Trp
                405                 410                 415

Val Asn Asp Glu Leu Gly Ile Glu Leu Pro Lys Cys Val Pro Val Cys
            420                 425                 430

Gly Val Pro Thr Glu Pro Ile Ala Leu Gln Gln Arg Ile Phe Gly Gly
        435                 440                 445

Phe Pro Ala Lys Ile Gln Ser Phe Pro Trp Gln Val Phe Phe Glu Ser
    450                 455                 460

Pro Arg Ala Gly Gly Ala Leu Ile Asp Glu Tyr Trp Val Leu Thr Ala
465                 470                 475                 480

Ala His Gly Arg Glu Thr Leu Thr His Leu Cys Met Trp Gly Pro His
                485                 490                 495

Leu
```

<210> SEQ ID NO 12
<211> LENGTH: 461
<212> TYPE: PRT
<213> ORGANISM: Artificial sequence
<220> FEATURE:
<223> OTHER INFORMATION: synthetic sequence

<400> SEQUENCE: 12

```
Val Pro Val Trp Lys Glu Ala Thr Thr Thr Leu Phe Cys Ala Ser Asp
1               5                   10                  15

Ala Lys Ala Tyr Asp Thr Glu Ala His Asn Val Trp Ala Thr His Ala
            20                  25                  30

Cys Val Pro Thr Asp Pro Asn Pro Gln Glu Val Glu Leu Val Asn Val
        35                  40                  45

Thr Glu Asn Phe Asn Met Trp Lys Asn Asn Met Val Glu Gln Met His
    50                  55                  60

Glu Asp Ile Ile Ser Leu Trp Asp Gln Ser Leu Lys Pro Cys Val Lys
65                  70                  75                  80

Leu Thr Pro Leu Cys Val Thr Leu Asn Cys Thr Asp Leu Arg Asn Thr
                85                  90                  95

Thr Asn Thr Asn Asn Ser Thr Asp Asn Asn Asn Ser Lys Ser Glu Gly
            100                 105                 110

Thr Ile Lys Gly Gly Glu Met Lys Asn Cys Ser Phe Asn Ile Thr Thr
        115                 120                 125

Ser Ile Gly Asp Lys Met Gln Lys Glu Tyr Ala Leu Leu Tyr Lys Leu
    130                 135                 140

Asp Ile Glu Pro Ile Asp Asn Asp Ser Thr Ser Tyr Arg Leu Ile Ser
145                 150                 155                 160

Cys Asn Thr Ser Val Ile Thr Gln Ala Cys Pro Lys Ile Ser Phe Glu
                165                 170                 175

Pro Ile Pro Ile His Tyr Cys Ala Pro Ala Gly Phe Ala Ile Leu Lys
            180                 185                 190

Cys Asn Asp Lys Lys Phe Ser Gly Lys Gly Ser Cys Lys Asn Val Ser
        195                 200                 205

Thr Val Gln Cys Thr His Gly Ile Arg Pro Val Val Ser Thr Gln Leu
    210                 215                 220

Leu Leu Asn Gly Ser Leu Ala Glu Glu Glu Val Val Ile Arg Ser Glu
225                 230                 235                 240

Asp Phe Thr Asp Asn Ala Lys Thr Ile Ile Val His Leu Lys Glu Ser
                245                 250                 255

Val Gln Ile Asn Cys Thr Arg Pro Asn Asn Asn Thr Arg Lys Arg Ile
            260                 265                 270

His Ile Gly Pro Gly Arg Ala Phe Tyr Thr Thr Lys Asn Ile Lys Gly
        275                 280                 285

Thr Ile Arg Gln Ala His Cys Asn Ile Ser Arg Ala Lys Trp Asn Asp
    290                 295                 300

Thr Leu Arg Gln Ile Val Ser Lys Leu Lys Glu Gln Phe Lys Asn Lys
305                 310                 315                 320

Thr Ile Val Phe Asn Pro Ser Ser Gly Gly Asp Pro Glu Ile Val Met
                325                 330                 335

His Ser Phe Asn Cys Gly Gly Glu Phe Phe Tyr Cys Asn Thr Ser Pro
            340                 345                 350

Leu Phe Asn Ser Ile Trp Asn Gly Asn Asn Thr Trp Asn Asn Thr Thr
        355                 360                 365

Gly Ser Asn Asn Asn Ile Thr Leu Gln Cys Lys Ile Lys Gln Ile Ile
```

```
    370                 375                 380

Asn Met Trp Gln Lys Val Gly Lys Ala Met Tyr Ala Pro Pro Ile Glu
385                 390                 395                 400

Gly Gln Ile Arg Cys Ser Ser Asn Ile Thr Gly Leu Leu Leu Thr Arg
                405                 410                 415

Asp Gly Gly Glu Asp Thr Asp Thr Asn Asp Thr Glu Ile Phe Arg Pro
            420                 425                 430

Gly Gly Gly Asp Met Arg Asp Asn Trp Arg Ser Glu Leu Tyr Lys Tyr
        435                 440                 445

Lys Val Val Thr Ile Glu Pro Leu Gly Val Ala Pro Thr
    450                 455                 460


<210> SEQ ID NO 13
<211> LENGTH: 526
<212> TYPE: PRT
<213> ORGANISM: Artificial sequence
<220> FEATURE:
<223> OTHER INFORMATION: synthetic sequence

<400> SEQUENCE: 13

Met Gly Gly Ala Ala Ala Arg Leu Gly Ala Val Ile Leu Phe Val Val
1               5                   10                  15

Ile Val Gly Leu His Gly Val Arg Gly Lys Tyr Ala Leu Ala Asp Ala
            20                  25                  30

Ser Leu Lys Met Ala Asp Pro Asn Arg Phe Arg Gly Lys Asp Leu Pro
        35                  40                  45

Val Leu Asp Gln Leu Leu Glu Val Pro Val Trp Lys Glu Ala Thr Thr
    50                  55                  60

Thr Leu Phe Cys Ala Ser Asp Ala Lys Ala Tyr Asp Thr Glu Ala His
65                  70                  75                  80

Asn Val Trp Ala Thr His Ala Cys Val Pro Thr Asp Pro Asn Pro Gln
                85                  90                  95

Glu Val Glu Leu Val Asn Val Thr Glu Asn Phe Asn Met Trp Lys Asn
            100                 105                 110

Asn Met Val Glu Gln Met His Glu Asp Ile Ile Ser Leu Trp Asp Gln
        115                 120                 125

Ser Leu Lys Pro Cys Val Lys Leu Thr Pro Leu Cys Val Thr Leu Asn
    130                 135                 140

Cys Thr Asp Leu Arg Asn Thr Thr Asn Thr Asn Asn Ser Thr Asp Asn
145                 150                 155                 160

Asn Asn Ser Lys Ser Glu Gly Thr Ile Lys Gly Gly Glu Met Lys Asn
                165                 170                 175

Cys Ser Phe Asn Ile Thr Thr Ser Ile Gly Asp Lys Met Gln Lys Glu
            180                 185                 190

Tyr Ala Leu Leu Tyr Lys Leu Asp Ile Glu Pro Ile Asp Asn Asp Ser
        195                 200                 205

Thr Ser Tyr Arg Leu Ile Ser Cys Asn Thr Ser Val Ile Thr Gln Ala
    210                 215                 220

Cys Pro Lys Ile Ser Phe Glu Pro Ile Pro Ile His Tyr Cys Ala Pro
225                 230                 235                 240

Ala Gly Phe Ala Ile Leu Lys Cys Asn Asp Lys Lys Phe Ser Gly Lys
                245                 250                 255

Gly Ser Cys Lys Asn Val Ser Thr Val Gln Cys Thr His Gly Ile Arg
            260                 265                 270

Pro Val Val Ser Thr Gln Leu Leu Leu Asn Gly Ser Leu Ala Glu Glu
```

-continued

```
        275                 280                 285

Glu Val Val Ile Arg Ser Glu Asp Phe Thr Asp Asn Ala Lys Thr Ile
    290                 295                 300

Ile Val His Leu Lys Glu Ser Val Gln Ile Asn Cys Thr Arg Pro Asn
305                 310                 315                 320

Asn Asn Thr Arg Lys Arg Ile His Ile Gly Pro Gly Arg Ala Phe Tyr
                325                 330                 335

Thr Thr Lys Asn Ile Lys Gly Thr Ile Arg Gln Ala His Cys Asn Ile
            340                 345                 350

Ser Arg Ala Lys Trp Asn Asp Thr Leu Arg Gln Ile Val Ser Lys Leu
        355                 360                 365

Lys Glu Gln Phe Lys Asn Lys Thr Ile Val Phe Asn Pro Ser Ser Gly
    370                 375                 380

Gly Asp Pro Glu Ile Val Met His Ser Phe Asn Cys Gly Gly Glu Phe
385                 390                 395                 400

Phe Tyr Cys Asn Thr Ser Pro Leu Phe Asn Ser Ile Trp Asn Gly Asn
                405                 410                 415

Asn Thr Trp Asn Asn Thr Thr Gly Ser Asn Asn Asn Ile Thr Leu Gln
            420                 425                 430

Cys Lys Ile Lys Gln Ile Ile Asn Met Trp Gln Lys Val Gly Lys Ala
        435                 440                 445

Met Tyr Ala Pro Pro Ile Glu Gly Gln Ile Arg Cys Ser Ser Asn Ile
    450                 455                 460

Thr Gly Leu Leu Leu Thr Arg Asp Gly Gly Glu Asp Thr Asp Thr Asn
465                 470                 475                 480

Asp Thr Glu Ile Phe Arg Pro Gly Gly Gly Asp Met Arg Asp Asn Trp
                485                 490                 495

Arg Ser Glu Leu Tyr Lys Tyr Lys Val Val Thr Ile Glu Pro Leu Gly
            500                 505                 510

Val Ala Pro Thr Lys Ala Lys Arg Arg Val Val Gln Arg Glu
        515                 520                 525
```

```
<210> SEQ ID NO 14
<211> LENGTH: 2085
<212> TYPE: DNA
<213> ORGANISM: Artificial sequence
<220> FEATURE:
<223> OTHER INFORMATION: synthetic sequence

<400> SEQUENCE: 14

atgggcaaat caccagaggc atggtgcatt gtcttgtttt ctgttttggc atcattttct      60

gccgagccta ccatgcatgg ggagatcctg tcccctaact atcctcaggc gtaccccaat     120

gagatcgaga aaacgtggga catagaagtc ccagaagggt ttgggattcg cctctacttc     180

acccatctgg acatggagct gtcagagaac tgcgaatatg actcggtgca gataatctca     240

ggaggcgtcg aggaagggag actctgtggg cagaggacca gcaagaatgc caactccccc     300

attgtggaag agtttcaaat gccatacaat aaactccagg tgatctttag gtcagacttc     360

tccaacgaag agcggtttac tggctttgct gcatattacg ctgccgtaga tataaatgaa     420

tgcacagatt ttacagatgt cccttgcagc cacttctgca ataatttcat tggtggttac     480

ttctgctcct gtcccccaga atacttcctc cacgatgaca tgaggaactg cggagtcaat     540

tgtagtggga atgtattcac tgccctgatt ggggagattt caagccccaa ttatcccagt     600

ccatacccccg agaactcaag gtgtgaatac cagattttgc tggaggaggg gttccaagtg     660
```

-continued gtggtgacta tccggagaga agattttgat gtggaaccag ctgactcgga ggggaactgc 720
caggacagtt tactctttgc tgcaaaaaat caactatttg gtccttactg tggcaatggg 780
ttccctgggc cactaactat tgaaacccac agtaacactc ttgacattgt ctttcaaacg 840
gacctaacag agcaaagaaa aggctggaag cttcgttacc atggagaccc aatcccttgt 900
cccaaggaaa tcactgccaa ttctgtttgg gtgcctgaaa aggcaaaata tgtgtttaaa 960
gatgtggtga agatatcctg tgtggacgga tttgaagttg tagagggaaa tgttggctca 1020
gcattcttct attctacttg tcaaagcaat ggacagtgga gtaattccag actacaatgt 1080
cagcctgtgg actgtggtat tccggaaccc attcagaatg gtaaagttga cgatccagaa 1140
aacactgtgt ttggctctgt catccagtac tcgtgcgagg agccatatta ctacatggaa 1200
catgaagaac acggcgggga gtatcgctgc gctgctaatg ggagctgggt gaatgacgaa 1260
ctgggcatag agctcccaaa atgtgttcca gtctgtgggg tacccactga gcccattgca 1320
ttacagcaga ggatatttgg aggattccct gcaaagatcc agagttttcc ttggcaagtc 1380
ttctttgagt ccccacgggc cggtggggct cttattgacg agtactgggt gttgacagcc 1440
gcttttgtgg agggaaactc tgacccatct atgtatgtgg ggaccacatt tgtgagaatg 1500
gaacatctgg cgaatgccca gaggctcacc gctgaacgtg tgattattca tccaggctgg 1560
aagccagcgg atgacctaga aacacggaca aattttgaca atgacattgc actggtgcag 1620
ctgaaagacc ccgtgaaaat ggggcccact gtctccccca tctgcctgcc aggtacctcc 1680
tcagagtaca acccctcaaa gaatgacctg ggactgatct cagggtgggg ccgaacagag 1740
aagagaaata ttgttcccca actcaaaggg gcaaagttac ctgtgacctc tttagagaag 1800
tgccaacagg tgaaagggga gaactccaaa gtgagggcgg atgactacgt tttcaccagc 1860
aacatgatct gtgctggaga gaaaggtgtt gatagctgtc agggggacag tggtggggct 1920
tttgctttgc aggtccccaa tgtaaaggac cccaaattct atgtggcagg cctagtgtcc 1980 tggggggaaaa agtgtgggac ctatggaatc tacacaaagg taaagaacta catggattgg 2040
atcgtgaaga cgatgcagga gaatagtgtc cccagtaagg actaa 2085

<210> SEQ ID NO 15
<211> LENGTH: 684
<212> TYPE: PRT
<213> ORGANISM: Artificial sequence
<220> FEATURE:
<223> OTHER INFORMATION: synthetic sequence

<400> SEQUENCE: 15

Met Arg Val Lys Gly Ile Arg Arg Asn Tyr Gln His Trp Trp Gly Trp
1               5                   10                  15

Gly Thr Met Leu Leu Gly Leu Leu Met Ile Cys Ser Ala Thr Glu Lys
            20                  25                  30

Leu Trp Val Thr Val Tyr Tyr Gly Val Pro Val Trp Lys Glu Ala Thr
        35                  40                  45

Thr Thr Leu Phe Cys Ala Ser Asp Ala Lys Ala Tyr Asp Thr Glu Ala
    50                  55                  60

His Asn Val Trp Ala Thr His Ala Cys Val Pro Thr Asp Pro Asn Pro
65                  70                  75                  80

Gln Glu Val Glu Leu Val Asn Val Thr Glu Asn Phe Asn Met Trp Lys
                85                  90                  95

Asn Asn Met Val Glu Gln Met His Glu Asp Ile Ile Ser Leu Trp Asp
            100                 105                 110

-continued

```
Gln Ser Leu Lys Pro Cys Val Lys Leu Thr Pro Leu Cys Val Thr Leu
        115                 120                 125

Asn Cys Thr Asp Leu Arg Asn Thr Thr Asn Thr Asn Asn Ser Thr Asp
    130                 135                 140

Asn Asn Asn Ser Lys Ser Glu Gly Thr Ile Lys Gly Gly Glu Met Lys
145                 150                 155                 160

Asn Cys Ser Phe Asn Ile Thr Thr Ser Ile Gly Asp Lys Met Gln Lys
                165                 170                 175

Glu Tyr Ala Leu Leu Tyr Lys Leu Asp Ile Glu Pro Ile Asp Asn Asp
            180                 185                 190

Ser Thr Ser Tyr Arg Leu Ile Ser Cys Asn Thr Ser Val Ile Thr Gln
        195                 200                 205

Ala Cys Pro Lys Ile Ser Phe Glu Pro Ile Pro Ile His Tyr Cys Ala
    210                 215                 220

Pro Ala Gly Phe Ala Ile Leu Lys Cys Asn Asp Lys Lys Phe Ser Gly
225                 230                 235                 240

Lys Gly Ser Cys Lys Asn Val Ser Thr Val Gln Cys Thr His Gly Ile
                245                 250                 255

Arg Pro Val Val Ser Thr Gln Leu Leu Leu Asn Gly Ser Leu Ala Glu
            260                 265                 270

Glu Glu Val Val Ile Arg Ser Glu Asp Phe Thr Asp Asn Ala Lys Thr
        275                 280                 285

Ile Ile Val His Leu Lys Glu Ser Val Gln Ile Asn Cys Thr Arg Pro
    290                 295                 300

Asn Asn Asn Thr Arg Lys Arg Ile His Ile Gly Pro Gly Arg Ala Phe
305                 310                 315                 320

Tyr Thr Thr Lys Asn Ile Lys Gly Thr Ile Arg Gln Ala His Cys Asn
                325                 330                 335

Ile Ser Arg Ala Lys Trp Asn Asp Thr Leu Arg Gln Ile Val Ser Lys
            340                 345                 350

Leu Lys Glu Gln Phe Lys Asn Lys Thr Ile Val Phe Asn Pro Ser Ser
        355                 360                 365

Gly Gly Asp Pro Glu Ile Val Met His Ser Phe Asn Cys Gly Gly Glu
    370                 375                 380

Phe Phe Tyr Cys Asn Thr Ser Pro Leu Phe Asn Ser Ile Trp Asn Gly
385                 390                 395                 400

Asn Asn Thr Trp Asn Asn Thr Thr Gly Ser Asn Asn Asn Ile Thr Leu
                405                 410                 415

Gln Cys Lys Ile Lys Gln Ile Ile Asn Met Trp Gln Lys Val Gly Lys
            420                 425                 430

Ala Met Tyr Ala Pro Pro Ile Glu Gly Gln Ile Arg Cys Ser Ser Asn
        435                 440                 445

Ile Thr Gly Leu Leu Leu Thr Arg Asp Gly Gly Glu Asp Thr Asp Thr
    450                 455                 460

Asn Asp Thr Glu Ile Phe Arg Pro Gly Gly Gly Asp Met Arg Asp Asn
465                 470                 475                 480

Trp Arg Ser Glu Leu Tyr Lys Tyr Lys Val Val Thr Ile Glu Pro Leu
                485                 490                 495

Gly Val Ala Pro Thr Lys Ala Lys Arg Arg Val Val Gln Arg Glu Lys
            500                 505                 510

Arg Ala Ala Ile Gly Ala Leu Phe Leu Gly Phe Leu Gly Ala Ala Gly
        515                 520                 525

Ser Thr Met Gly Ala Ala Ser Val Thr Leu Thr Val Gln Ala Arg Leu
```

```
    530                 535                 540

Leu Leu Ser Gly Ile Val Gln Gln Gln Asn Asn Leu Leu Arg Ala Ile
545                 550                 555                 560

Glu Ala Gln Gln His Met Leu Gln Leu Thr Val Trp Gly Ile Lys Gln
                565                 570                 575

Leu Gln Ala Arg Val Leu Ala Val Glu Arg Tyr Leu Lys Asp Gln Gln
            580                 585                 590

Leu Leu Gly Phe Trp Gly Cys Ser Gly Lys Leu Ile Cys Thr Thr Thr
        595                 600                 605

Val Pro Trp Asn Ala Ser Trp Ser Asn Lys Ser Leu Asp Asp Ile Trp
    610                 615                 620

Asn Asn Met Thr Trp Met Gln Trp Glu Arg Glu Ile Asp Asn Tyr Thr
625                 630                 635                 640

Ser Leu Ile Tyr Ser Leu Leu Glu Lys Ser Gln Thr Gln Gln Glu Lys
                645                 650                 655

Asn Glu Gln Glu Leu Leu Glu Leu Asp Lys Trp Ala Ser Leu Trp Asn
            660                 665                 670

Trp Phe Asp Ile Thr Asn Trp Leu Trp Tyr Ile Lys
        675                 680


<210> SEQ ID NO 16
<211> LENGTH: 694
<212> TYPE: PRT
<213> ORGANISM: Artificial sequence
<220> FEATURE:
<223> OTHER INFORMATION: synthetic sequence

<400> SEQUENCE: 16

Met Gly Lys Ser Pro Glu Ala Trp Cys Ile Val Leu Phe Ser Val Leu
1               5                   10                  15

Ala Ser Phe Ser Ala Glu Pro Thr Met His Gly Glu Ile Leu Ser Pro
            20                  25                  30

Asn Tyr Pro Gln Ala Tyr Pro Asn Glu Ile Glu Lys Thr Trp Asp Ile
        35                  40                  45

Glu Val Pro Glu Gly Phe Gly Ile Arg Leu Tyr Phe Thr His Leu Asp
    50                  55                  60

Met Glu Leu Ser Glu Asn Cys Glu Tyr Asp Ser Val Gln Ile Ile Ser
65                  70                  75                  80

Gly Gly Val Glu Glu Gly Arg Leu Cys Gly Gln Arg Thr Ser Lys Asn
                85                  90                  95

Ala Asn Ser Pro Ile Val Glu Glu Phe Gln Met Pro Tyr Asn Lys Leu
            100                 105                 110

Gln Val Ile Phe Arg Ser Asp Phe Ser Asn Glu Glu Arg Phe Thr Gly
        115                 120                 125

Phe Ala Ala Tyr Tyr Ala Ala Val Asp Ile Asn Glu Cys Thr Asp Phe
    130                 135                 140

Thr Asp Val Pro Cys Ser His Phe Cys Asn Asn Phe Ile Gly Gly Tyr
145                 150                 155                 160

Phe Cys Ser Cys Pro Pro Glu Tyr Phe Leu His Asp Asp Met Arg Asn
                165                 170                 175

Cys Gly Val Asn Cys Ser Gly Asn Val Phe Thr Ala Leu Ile Gly Glu
            180                 185                 190

Ile Ser Ser Pro Asn Tyr Pro Ser Pro Tyr Pro Glu Asn Ser Arg Cys
        195                 200                 205

Glu Tyr Gln Ile Leu Leu Glu Glu Gly Phe Gln Val Val Val Thr Ile
```

```
    210                 215                 220

Arg Arg Glu Asp Phe Asp Val Glu Pro Ala Asp Ser Glu Gly Asn Cys
225                 230                 235                 240

Gln Asp Ser Leu Leu Phe Ala Ala Lys Asn Gln Leu Phe Gly Pro Tyr
                245                 250                 255

Cys Gly Asn Gly Phe Pro Gly Pro Leu Thr Ile Glu Thr His Ser Asn
            260                 265                 270

Thr Leu Asp Ile Val Phe Gln Thr Asp Leu Thr Glu Gln Arg Lys Gly
        275                 280                 285

Trp Lys Leu Arg Tyr His Gly Asp Pro Ile Pro Cys Pro Lys Glu Ile
    290                 295                 300

Thr Ala Asn Ser Val Trp Val Pro Glu Lys Ala Lys Tyr Val Phe Lys
305                 310                 315                 320

Asp Val Val Lys Ile Ser Cys Val Asp Gly Phe Glu Val Val Glu Gly
                325                 330                 335

Asn Val Gly Ser Ala Phe Phe Tyr Ser Thr Cys Gln Ser Asn Gly Gln
            340                 345                 350

Trp Ser Asn Ser Arg Leu Gln Cys Gln Pro Val Asp Cys Gly Ile Pro
        355                 360                 365

Glu Pro Ile Gln Asn Gly Lys Val Asp Asp Pro Glu Asn Thr Val Phe
    370                 375                 380

Gly Ser Val Ile Gln Tyr Ser Cys Glu Glu Pro Tyr Tyr Tyr Met Glu
385                 390                 395                 400

His Glu Glu His Gly Gly Glu Tyr Arg Cys Ala Ala Asn Gly Ser Trp
                405                 410                 415

Val Asn Asp Glu Leu Gly Ile Glu Leu Pro Lys Cys Val Pro Val Cys
            420                 425                 430

Gly Val Pro Thr Glu Pro Ile Ala Leu Gln Gln Arg Ile Phe Gly Gly
        435                 440                 445

Phe Pro Ala Lys Ile Gln Ser Phe Pro Trp Gln Val Phe Phe Glu Ser
    450                 455                 460

Pro Arg Ala Gly Gly Ala Leu Ile Asp Glu Tyr Trp Val Leu Thr Ala
465                 470                 475                 480

Ala Phe Val Glu Gly Asn Ser Asp Pro Ser Met Tyr Val Gly Thr Thr
                485                 490                 495

Phe Val Arg Met Glu His Leu Ala Asn Ala Gln Arg Leu Thr Ala Glu
            500                 505                 510

Arg Val Ile Ile His Pro Gly Trp Lys Pro Ala Asp Asp Leu Glu Thr
        515                 520                 525

Arg Thr Asn Phe Asp Asn Asp Ile Ala Leu Val Gln Leu Lys Asp Pro
    530                 535                 540

Val Lys Met Gly Pro Thr Val Ser Pro Ile Cys Leu Pro Gly Thr Ser
545                 550                 555                 560

Ser Glu Tyr Asn Pro Ser Lys Asn Asp Leu Gly Leu Ile Ser Gly Trp
                565                 570                 575

Gly Arg Thr Glu Lys Arg Asn Ile Val Pro Gln Leu Lys Gly Ala Lys
            580                 585                 590

Leu Pro Val Thr Ser Leu Glu Lys Cys Gln Gln Val Lys Gly Glu Asn
        595                 600                 605

Ser Lys Val Arg Ala Asp Asp Tyr Val Phe Thr Ser Asn Met Ile Cys
    610                 615                 620

Ala Gly Glu Lys Gly Val Asp Ser Cys Gln Gly Asp Ser Gly Gly Ala
625                 630                 635                 640
```

```
Phe Ala Leu Gln Val Pro Asn Val Lys Asp Pro Lys Phe Tyr Val Ala
                645                 650                 655

Gly Leu Val Ser Trp Gly Lys Lys Cys Gly Thr Tyr Gly Ile Tyr Thr
            660                 665                 670

Lys Val Lys Asn Tyr Met Asp Trp Ile Val Lys Thr Met Gln Glu Asn
        675                 680                 685

Ser Val Pro Ser Lys Asp
    690
```

<210> SEQ ID NO 17
<211> LENGTH: 20
<212> TYPE: DNA
<213> ORGANISM: Artificial sequence
<220> FEATURE:
<223> OTHER INFORMATION: synthetic sequence

<400> SEQUENCE: 17

```
gataatctca ggaggcgtcg                                                20
```

<210> SEQ ID NO 18
<211> LENGTH: 20
<212> TYPE: DNA
<213> ORGANISM: Artificial sequence
<220> FEATURE:
<223> OTHER INFORMATION: synthetic sequence

<400> SEQUENCE: 18

```
gccagtaaac cgctcttcgt                                                20
```

<210> SEQ ID NO 19
<211> LENGTH: 20
<212> TYPE: DNA
<213> ORGANISM: Artificial sequence
<220> FEATURE:
<223> OTHER INFORMATION: synthetic sequence

<400> SEQUENCE: 19

```
gttgacagcc gctcatgttg                                                20
```

<210> SEQ ID NO 20
<211> LENGTH: 680
<212> TYPE: PRT
<213> ORGANISM: Artificial sequence
<220> FEATURE:
<223> OTHER INFORMATION: synthetic sequence

<400> SEQUENCE: 20

```
Met Arg Val Thr Glu Ile Arg Lys Ser Tyr Gln His Trp Trp Arg Trp
1               5                   10                  15

Gly Ile Met Leu Leu Gly Ile Leu Met Ile Cys Asn Ala Glu Glu Lys
            20                  25                  30

Leu Trp Val Thr Val Tyr Tyr Gly Val Pro Val Trp Lys Glu Ala Thr
        35                  40                  45

Thr Thr Leu Phe Cys Ala Ser Asp Ala Lys Ala Tyr Asp Thr Glu Val
    50                  55                  60

His Asn Val Trp Ala Thr His Ala Cys Val Pro Thr Asp Pro Asn Pro
65                  70                  75                  80

Gln Glu Val Ala Leu Glu Asn Val Thr Glu Asn Phe Asn Met Trp Lys
                85                  90                  95

Asn Asn Met Val Glu Gln Met His Glu Asp Ile Ile Ser Leu Trp Asp
            100                 105                 110
```

-continued

```
Gln Ser Leu Lys Pro Cys Val Lys Leu Thr Pro Leu Cys Val Thr Leu
        115                 120                 125

Asn Cys Thr Asp Leu Arg Asn Ala Thr Ser Arg Asn Val Thr Asn Thr
    130                 135                 140

Thr Ser Ser Ser Arg Gly Met Val Gly Gly Gly Glu Met Lys Asn Cys
145                 150                 155                 160

Ser Phe Asn Ile Thr Thr Gly Ile Arg Gly Lys Val Gln Lys Glu Tyr
                165                 170                 175

Ala Leu Phe Tyr Glu Leu Asp Ile Val Pro Ile Asp Asn Lys Ile Asp
            180                 185                 190

Arg Tyr Arg Leu Ile Ser Cys Asn Thr Ser Val Ile Thr Gln Ala Cys
        195                 200                 205

Pro Lys Val Ser Phe Glu Pro Ile Pro Ile His Tyr Cys Ala Pro Ala
    210                 215                 220

Gly Phe Ala Ile Leu Lys Cys Lys Asp Lys Lys Phe Asn Gly Lys Gly
225                 230                 235                 240

Pro Cys Ser Asn Val Ser Thr Val Gln Cys Thr His Gly Ile Arg Pro
                245                 250                 255

Val Val Ser Thr Gln Leu Leu Leu Asn Gly Ser Leu Ala Glu Glu Glu
            260                 265                 270

Val Val Ile Arg Ser Glu Asn Phe Thr Asn Asn Ala Lys Thr Ile Ile
        275                 280                 285

Val Gln Leu Asn Glu Ser Val Glu Ile Asn Cys Thr Arg Pro Asn Asn
    290                 295                 300

Asn Thr Arg Lys Ser Ile Asn Ile Gly Pro Gly Arg Ala Phe Tyr Thr
305                 310                 315                 320

Thr Gly Glu Ile Ile Gly Asp Ile Arg Gln Ala His Cys Asn Leu Ser
                325                 330                 335

Arg Ala Lys Trp Asn Asp Thr Leu Asn Lys Ile Val Ile Lys Leu Arg
            340                 345                 350

Glu Gln Phe Gly Asn Lys Thr Ile Val Phe Lys His Ser Ser Gly Gly
        355                 360                 365

Asp Pro Glu Ile Val Thr His Ser Phe Asn Cys Gly Gly Glu Phe Phe
    370                 375                 380

Tyr Cys Asn Ser Thr Gln Leu Phe Asn Ser Thr Trp Asn Val Thr Glu
385                 390                 395                 400

Glu Ser Asn Asn Thr Val Glu Asn Asn Thr Ile Thr Leu Pro Cys Arg
                405                 410                 415

Ile Lys Gln Ile Ile Asn Met Trp Gln Glu Val Gly Arg Ala Met Tyr
            420                 425                 430

Ala Pro Pro Ile Arg Gly Gln Ile Arg Cys Ser Ser Asn Ile Thr Gly
        435                 440                 445

Leu Leu Leu Thr Arg Asp Gly Gly Pro Glu Asp Asn Lys Thr Glu Val
    450                 455                 460

Phe Arg Pro Gly Gly Gly Asp Met Arg Asp Asn Trp Arg Ser Glu Leu
465                 470                 475                 480

Tyr Lys Tyr Lys Val Val Lys Ile Glu Pro Leu Gly Val Ala Pro Thr
                485                 490                 495

Lys Ala Lys Arg Arg Val Val Gln Arg Glu Lys Arg Ala Val Gly Ile
            500                 505                 510

Gly Ala Val Phe Leu Gly Phe Leu Gly Ala Ala Gly Ser Thr Met Gly
        515                 520                 525
```

```
Ala Ala Ser Met Thr Leu Thr Val Gln Ala Arg Leu Leu Leu Ser Gly
    530                 535                 540

Ile Val Gln Gln Gln Asn Asn Leu Leu Arg Ala Ile Glu Ala Gln Gln
545                 550                 555                 560

His Leu Leu Gln Leu Thr Val Trp Gly Ile Lys Gln Leu Gln Ala Arg
                565                 570                 575

Val Leu Ala Val Glu Arg Tyr Leu Arg Asp Gln Gln Leu Leu Gly Ile
            580                 585                 590

Trp Gly Cys Ser Gly Lys Leu Ile Cys Thr Thr Ala Val Pro Trp Asn
        595                 600                 605

Ala Ser Trp Ser Asn Lys Ser Leu Asn Lys Ile Trp Asp Asn Met Thr
    610                 615                 620

Trp Met Glu Trp Asp Arg Glu Ile Asn Asn Tyr Thr Ser Ile Ile Tyr
625                 630                 635                 640

Ser Leu Ile Glu Glu Ser Gln Asn Gln Gln Glu Lys Asn Glu Gln Glu
                645                 650                 655

Leu Leu Glu Leu Asp Lys Trp Ala Ser Leu Trp Asn Trp Phe Asp Ile
            660                 665                 670

Thr Lys Trp Leu Trp Tyr Ile Lys
        675                 680


<210> SEQ ID NO 21
<211> LENGTH: 23
<212> TYPE: DNA
<213> ORGANISM: Artificial sequence
<220> FEATURE:
<223> OTHER INFORMATION: synthetic sequence

<400> SEQUENCE: 21

gccagcattg attcctgcat ctc                                              23


<210> SEQ ID NO 22
<211> LENGTH: 453
<212> TYPE: PRT
<213> ORGANISM: Artificial sequence
<220> FEATURE:
<223> OTHER INFORMATION: synthetic sequence

<400> SEQUENCE: 22

Val Pro Val Trp Lys Glu Ala Lys Thr Thr Leu Phe Cys Ala Ser Glu
1               5                   10                  15

Ala Lys Gly Tyr Glu Lys Glu Val His Asn Val Trp Ala Thr His Ala
            20                  25                  30

Cys Val Pro Thr Asp Pro Ser Pro His Glu Leu Val Leu Glu Asn Val
        35                  40                  45

Thr Glu Asn Phe Asn Met Trp Glu Asn Asp Met Val Asp Gln Met His
    50                  55                  60

Glu Asp Ile Ile Ser Leu Trp Asp Gln Ser Leu Lys Pro Cys Val Lys
65                  70                  75                  80

Leu Thr Pro Leu Cys Val Thr Leu Asn Cys Thr Asn Val Thr Gly Thr
                85                  90                  95

Asn Val Thr Gly Asn Asp Met Lys Gly Glu Met Thr Asn Cys Ser Phe
            100                 105                 110

Asn Ala Thr Thr Glu Ile Lys Asp Arg Lys Lys Asn Val Tyr Ala Leu
        115                 120                 125

Phe Tyr Lys Leu Asp Val Val Gln Leu Glu Gly Asn Ser Ser Asn Ser
    130                 135                 140
```

-continued

Thr Tyr Ser Thr Tyr Arg Leu Ile Asn Cys Asn Thr Ser Val Ile Thr
145 150 155 160

Gln Ala Cys Pro Lys Val Ser Phe Asp Pro Ile Pro Ile His Tyr Cys
165 170 175

Ala Pro Ala Gly Tyr Ala Ile Leu Lys Cys Asn Asn Lys Thr Phe Asn
180 185 190

Gly Thr Gly Pro Cys Asn Asn Val Ser Thr Val Gln Cys Thr His Gly
195 200 205

Ile Lys Pro Val Val Ser Thr Gln Leu Leu Leu Asn Gly Ser Leu Ala
210 215 220

Glu Lys Glu Ile Val Ile Arg Ser Lys Asn Leu Thr Asp Asn Val Lys
225 230 235 240

Thr Ile Ile Val His Leu Asn Glu Ser Val Glu Ile Thr Cys Ile Arg
245 250 255

Pro Gly Asn Asn Thr Arg Lys Ser Ile Arg Ile Gly Pro Gly Gln Ala
260 265 270

Phe Tyr Ala Thr Gly Asp Ile Ile Gly Asn Ile Arg Gln Ala His Cys
275 280 285

Asn Ile Ser Glu Asp Lys Trp Asn Lys Thr Leu Gln Met Val Gly Glu
290 295 300

Lys Leu Gly Lys Leu Phe Pro Asn Lys Thr Ile Lys Glu Pro Ala Ser
305 310 315 320

Gly Gly Asp Leu Glu Ile Thr Thr His Ser Phe Asn Cys Arg Gly Glu
325 330 335

Phe Phe Tyr Cys Asn Thr Thr Lys Leu Phe Asn Ser Thr Tyr Arg Pro
340 345 350

Asn Ala Asn Ala Asn Ser Ser Ser Ser Asn Asn Thr Ile Thr Leu Gln
355 360 365

Cys Lys Ile Lys Gln Ile Ile Asn Met Trp Gln Glu Val Gly Arg Ala
370 375 380

Met Tyr Ala Pro Pro Ile Ala Gly Asn Ile Thr Cys Thr Ser Asn Ile
385 390 395 400

Thr Gly Leu Leu Leu Val Arg Asp Gly Gly Asn Asn Ser Thr Glu Glu
405 410 415

Glu Ile Phe Arg Pro Gly Gly Gly Asn Met Lys Asp Asn Trp Arg Ser
420 425 430

Glu Leu Tyr Lys Tyr Lys Val Val Glu Ile Lys Pro Leu Gly Val Ala
435 440 445

Pro Thr Gly Ala Lys
450

<210> SEQ ID NO 23
<211> LENGTH: 531
<212> TYPE: PRT
<213> ORGANISM: Artificial sequence
<220> FEATURE:
<223> OTHER INFORMATION: synthetic sequence

<400> SEQUENCE: 23

Met Gly Gly Ala Ala Ala Arg Leu Gly Ala Val Ile Leu Phe Val Val
1 5 10 15

Ile Val Gly Leu His Gly Val Arg Gly Lys Tyr Ala Leu Ala Asp Ala
20 25 30

Ser Leu Lys Met Ala Asp Pro Asn Arg Phe Arg Gly Lys Asp Leu Pro
35 40 45

```
Val Leu Asp Gln Leu Leu Glu Val Pro Val Trp Lys Glu Ala Lys Thr
    50                  55                  60

Thr Leu Phe Cys Ala Ser Glu Ala Lys Gly Tyr Glu Lys Glu Val His
65                  70                  75                  80

Asn Val Trp Ala Thr His Ala Cys Val Pro Thr Asp Pro Ser Pro His
                85                  90                  95

Glu Leu Val Leu Glu Asn Val Thr Glu Asn Phe Asn Met Trp Glu Asn
            100                 105                 110

Asp Met Val Asp Gln Met His Glu Asp Ile Ile Ser Leu Trp Asp Gln
        115                 120                 125

Ser Leu Lys Pro Cys Val Lys Leu Thr Pro Leu Cys Val Thr Leu Asn
    130                 135                 140

Cys Thr Asn Val Thr Gly Thr Asn Val Thr Gly Asn Asp Met Lys Gly
145                 150                 155                 160

Glu Met Thr Asn Cys Ser Phe Asn Ala Thr Thr Glu Ile Lys Asp Arg
                165                 170                 175

Lys Lys Asn Val Tyr Ala Leu Phe Tyr Lys Leu Asp Val Val Gln Leu
            180                 185                 190

Glu Gly Asn Ser Ser Asn Ser Thr Tyr Ser Thr Tyr Arg Leu Ile Asn
        195                 200                 205

Cys Asn Thr Ser Val Ile Thr Gln Ala Cys Pro Lys Val Ser Phe Asp
    210                 215                 220

Pro Ile Pro Ile His Tyr Cys Ala Pro Ala Gly Tyr Ala Ile Leu Lys
225                 230                 235                 240

Cys Asn Asn Lys Thr Phe Asn Gly Thr Gly Pro Cys Asn Asn Val Ser
                245                 250                 255

Thr Val Gln Cys Thr His Gly Ile Lys Pro Val Val Ser Thr Gln Leu
            260                 265                 270

Leu Leu Asn Gly Ser Leu Ala Glu Lys Glu Ile Val Ile Arg Ser Lys
        275                 280                 285

Asn Leu Thr Asp Asn Val Lys Thr Ile Ile Val His Leu Asn Glu Ser
    290                 295                 300

Val Glu Ile Thr Cys Ile Arg Pro Gly Asn Asn Thr Arg Lys Ser Ile
305                 310                 315                 320

Arg Ile Gly Pro Gly Gln Ala Phe Tyr Ala Thr Gly Asp Ile Ile Gly
                325                 330                 335

Asn Ile Arg Gln Ala His Cys Asn Ile Ser Glu Asp Lys Trp Asn Lys
            340                 345                 350

Thr Leu Gln Met Val Gly Glu Lys Leu Gly Lys Leu Phe Pro Asn Lys
        355                 360                 365

Thr Ile Lys Glu Pro Ala Ser Gly Gly Asp Leu Glu Ile Thr Thr His
    370                 375                 380

Ser Phe Asn Cys Arg Gly Glu Phe Phe Tyr Cys Asn Thr Thr Lys Leu
385                 390                 395                 400

Phe Asn Ser Thr Tyr Arg Pro Asn Ala Asn Ala Asn Ser Ser Ser Ser
                405                 410                 415

Asn Asn Thr Ile Thr Leu Gln Cys Lys Ile Lys Gln Ile Ile Asn Met
            420                 425                 430

Trp Gln Glu Val Gly Arg Ala Met Tyr Ala Pro Pro Ile Ala Gly Asn
        435                 440                 445

Ile Thr Cys Thr Ser Asn Ile Thr Gly Leu Leu Leu Val Arg Asp Gly
    450                 455                 460

Gly Asn Asn Ser Thr Glu Glu Glu Ile Phe Arg Pro Gly Gly Gly Asn
```

```
465                 470                 475                 480

Met Lys Asp Asn Trp Arg Ser Glu Leu Tyr Lys Tyr Lys Val Val Glu
                485                 490                 495

Ile Lys Pro Leu Gly Val Ala Pro Thr Gly Ala Lys Arg Arg Val Val
            500                 505                 510

Glu Arg Glu Lys Arg Ala Val Gly Ile Gly Ala Val Phe Leu Gly Phe
        515                 520                 525

Leu Gly Ala
    530


<210> SEQ ID NO 24
<211> LENGTH: 23
<212> TYPE: DNA
<213> ORGANISM: Artificial sequence
<220> FEATURE:
<223> OTHER INFORMATION: synthetic sequence

<400> SEQUENCE: 24

cccattttca cggggtcttt cag                                           23


<210> SEQ ID NO 25
<211> LENGTH: 457
<212> TYPE: PRT
<213> ORGANISM: Artificial sequence
<220> FEATURE:
<223> OTHER INFORMATION: synthetic sequence

<400> SEQUENCE: 25

Val Pro Val Trp Lys Glu Ala Thr Thr Thr Leu Phe Cys Ala Ser Asp
1               5                   10                  15

Ala Lys Ala Tyr Asp Thr Glu Val Arg Asn Val Trp Ala Thr His Ala
            20                  25                  30

Cys Val Pro Ala Asp Pro Asn Pro Gln Glu Met Val Leu Glu Asn Val
        35                  40                  45

Thr Glu Asn Phe Asn Met Trp Lys Asn Glu Met Val Asn Gln Met Gln
    50                  55                  60

Glu Asp Val Ile Ser Leu Trp Asp Gln Ser Leu Lys Pro Cys Val Lys
65                  70                  75                  80

Leu Thr Pro Leu Cys Val Thr Leu Glu Cys Arg Asn Val Ser Ser Asn
                85                  90                  95

Ser Asn Gly Ala His Asn Glu Thr Tyr His Glu Ser Met Lys Glu Met
            100                 105                 110

Lys Asn Cys Ser Phe Asn Ala Thr Thr Val Val Arg Asp Arg Lys Gln
        115                 120                 125

Thr Val Tyr Ala Leu Phe Tyr Arg Leu Asn Ile Val Pro Leu Thr Lys
    130                 135                 140

Lys Asn Ser Ser Glu Asn Ser Ser Glu Tyr Tyr Arg Leu Ile Asn Cys
145                 150                 155                 160

Asn Thr Ser Ala Ile Thr Gln Ala Cys Pro Lys Val Thr Phe Asp Pro
                165                 170                 175

Ile Pro Ile His Tyr Cys Thr Pro Ala Gly Tyr Ala Ile Leu Lys Cys
            180                 185                 190

Asn Asp Lys Ile Phe Asn Gly Thr Gly Pro Cys His Asn Val Ser Thr
        195                 200                 205

Val Gln Cys Thr His Gly Ile Lys Pro Val Val Ser Thr Gln Leu Leu
    210                 215                 220

Leu Asn Gly Ser Leu Ala Glu Gly Glu Ile Ile Ile Arg Ser Glu Asn
```

-continued 225 230 235 240

Leu Thr Asn Asn Val Lys Thr Ile Ile Val His Leu Asn Gln Ser Val
245 250 255

Glu Ile Val Cys Thr Arg Pro Gly Asn Asn Thr Arg Lys Ser Ile Arg
260 265 270

Ile Gly Pro Gly Gln Thr Phe Tyr Ala Thr Gly Asp Ile Ile Gly Asp
275 280 285

Ile Arg Gln Ala His Cys Asn Ile Ser Glu Asp Lys Trp Asn Glu Thr
290 295 300

Leu Gln Arg Val Ser Lys Lys Leu Ala Glu His Phe Gln Asn Lys Thr
305 310 315 320

Ile Lys Phe Ala Ser Ser Ser Gly Gly Asp Leu Glu Ile Thr Thr His
325 330 335

Ser Phe Asn Cys Arg Gly Glu Phe Phe Tyr Cys Asn Thr Ser Gly Leu
340 345 350

Phe Asn Gly Thr Tyr Thr Pro Asn Gly Thr Lys Ser Asn Ser Ser Ser
355 360 365

Ile Ile Thr Ile Pro Cys Arg Ile Lys Gln Ile Ile Asn Met Trp Gln
370 375 380

Glu Val Gly Arg Ala Met Tyr Ala Pro Pro Ile Glu Gly Asn Ile Thr
385 390 395 400

Cys Lys Ser Asn Ile Thr Gly Leu Leu Leu Val Arg Asp Gly Gly Thr
405 410 415

Glu Pro Asn Asp Thr Glu Thr Phe Arg Pro Gly Gly Gly Asp Met Arg
420 425 430

Asn Asn Trp Arg Ser Glu Leu Tyr Lys Tyr Lys Val Val Glu Ile Lys
435 440 445

Pro Leu Gly Val Ala Pro Thr Thr Ala
450 455

<210> SEQ ID NO 26
<211> LENGTH: 23
<212> TYPE: DNA
<213> ORGANISM: Artificial sequence
<220> FEATURE:
<223> OTHER INFORMATION: synthetic sequence

<400> SEQUENCE: 26
gttgacagcc gctcatgttg tgg 23

<210> SEQ ID NO 27
<211> LENGTH: 856
<212> TYPE: PRT
<213> ORGANISM: HIV

<400> SEQUENCE: 27

Met Arg Val Lys Glu Lys Tyr Gln His Leu Trp Arg Trp Gly Trp Arg
1 5 10 15

Trp Gly Thr Met Leu Leu Gly Met Leu Met Ile Cys Ser Ala Thr Glu
20 25 30

Lys Leu Trp Val Thr Val Tyr Tyr Gly Val Pro Val Trp Lys Glu Ala
35 40 45

Thr Thr Thr Leu Phe Cys Ala Ser Asp Ala Lys Ala Tyr Asp Thr Glu
50 55 60

Val His Asn Val Trp Ala Thr His Ala Cys Val Pro Thr Asp Pro Asn
65 70 75 80

-continued

```
Pro Gln Glu Val Val Leu Val Asn Val Thr Glu Asn Phe Asn Met Trp
                85                  90                  95

Lys Asn Asp Met Val Glu Gln Met His Glu Asp Ile Ile Ser Leu Trp
            100                 105                 110

Asp Gln Ser Leu Lys Pro Cys Val Lys Leu Thr Pro Leu Cys Val Ser
        115                 120                 125

Leu Lys Cys Thr Asp Leu Lys Asn Asp Thr Asn Thr Asn Ser Ser Ser
    130                 135                 140

Gly Arg Met Ile Met Glu Lys Gly Glu Ile Lys Asn Cys Ser Phe Asn
145                 150                 155                 160

Ile Ser Thr Ser Ile Arg Gly Lys Val Gln Lys Glu Tyr Ala Phe Phe
                165                 170                 175

Tyr Lys Leu Asp Ile Ile Pro Ile Asp Asn Asp Thr Thr Ser Tyr Lys
            180                 185                 190

Leu Thr Ser Cys Asn Thr Ser Val Ile Thr Gln Ala Cys Pro Lys Val
        195                 200                 205

Ser Phe Glu Pro Ile Pro Ile His Tyr Cys Ala Pro Ala Gly Phe Ala
    210                 215                 220

Ile Leu Lys Cys Asn Asn Lys Thr Phe Asn Gly Thr Gly Pro Cys Thr
225                 230                 235                 240

Asn Val Ser Thr Val Gln Cys Thr His Gly Ile Arg Pro Val Val Ser
                245                 250                 255

Thr Gln Leu Leu Leu Asn Gly Ser Leu Ala Glu Glu Glu Val Val Ile
            260                 265                 270

Arg Ser Val Asn Phe Thr Asp Asn Ala Lys Thr Ile Ile Val Gln Leu
        275                 280                 285

Asn Thr Ser Val Glu Ile Asn Cys Thr Arg Pro Asn Asn Asn Thr Arg
    290                 295                 300

Lys Arg Ile Arg Ile Gln Arg Gly Pro Gly Arg Ala Phe Val Thr Ile
305                 310                 315                 320

Gly Lys Ile Gly Asn Met Arg Gln Ala His Cys Asn Ile Ser Arg Ala
                325                 330                 335

Lys Trp Asn Asn Thr Leu Lys Gln Ile Ala Ser Lys Leu Arg Glu Gln
            340                 345                 350

Phe Gly Asn Asn Lys Thr Ile Ile Phe Lys Gln Ser Ser Gly Gly Asp
        355                 360                 365

Pro Glu Ile Val Thr His Ser Phe Asn Cys Gly Gly Glu Phe Phe Tyr
    370                 375                 380

Cys Asn Ser Thr Gln Leu Phe Asn Ser Thr Trp Phe Asn Ser Thr Trp
385                 390                 395                 400

Ser Thr Glu Gly Ser Asn Asn Thr Glu Gly Ser Asp Thr Ile Thr Leu
                405                 410                 415

Pro Cys Arg Ile Lys Gln Ile Ile Asn Met Trp Gln Lys Val Gly Lys
            420                 425                 430

Ala Met Tyr Ala Pro Pro Ile Ser Gly Gln Ile Arg Cys Ser Ser Asn
        435                 440                 445

Ile Thr Gly Leu Leu Leu Thr Arg Asp Gly Gly Asn Ser Asn Asn Glu
    450                 455                 460

Ser Glu Ile Phe Arg Pro Gly Gly Gly Asp Met Arg Asp Asn Trp Arg
465                 470                 475                 480

Ser Glu Leu Tyr Lys Tyr Lys Val Val Lys Ile Glu Pro Leu Gly Val
                485                 490                 495

Ala Pro Thr Lys Ala Lys Arg Arg Val Val Gln Arg Glu Lys Arg Ala
```

500 505 510

Val Gly Ile Gly Ala Leu Phe Leu Gly Phe Leu Gly Ala Ala Gly Ser
515 520 525

Thr Met Gly Ala Ala Ser Met Thr Leu Thr Val Gln Ala Arg Gln Leu
530 535 540

Leu Ser Gly Ile Val Gln Gln Gln Asn Asn Leu Leu Arg Ala Ile Glu
545 550 555 560

Ala Gln Gln His Leu Leu Gln Leu Thr Val Trp Gly Ile Lys Gln Leu
565 570 575

Gln Ala Arg Ile Leu Ala Val Glu Arg Tyr Leu Lys Asp Gln Gln Leu
580 585 590

Leu Gly Ile Trp Gly Cys Ser Gly Lys Leu Ile Cys Thr Thr Ala Val
595 600 605

Pro Trp Asn Ala Ser Trp Ser Asn Lys Ser Leu Glu Gln Ile Trp Asn
610 615 620

His Thr Thr Trp Met Glu Trp Asp Arg Glu Ile Asn Asn Tyr Thr Ser
625 630 635 640

Leu Ile His Ser Leu Ile Glu Glu Ser Gln Asn Gln Gln Glu Lys Asn
645 650 655

Glu Gln Glu Leu Leu Glu Leu Asp Lys Trp Ala Ser Leu Trp Asn Trp
660 665 670

Phe Asn Ile Thr Asn Trp Leu Trp Tyr Ile Lys Leu Phe Ile Met Ile
675 680 685

Val Gly Gly Leu Val Gly Leu Arg Ile Val Phe Ala Val Leu Ser Ile
690 695 700

Val Asn Arg Val Arg Gln Gly Tyr Ser Pro Leu Ser Phe Gln Thr His
705 710 715 720

Leu Pro Thr Pro Arg Gly Pro Asp Arg Pro Glu Gly Ile Glu Glu Glu
725 730 735

Gly Gly Glu Arg Asp Arg Asp Arg Ser Ile Arg Leu Val Asn Gly Ser
740 745 750

Leu Ala Leu Ile Trp Asp Asp Leu Arg Ser Leu Cys Leu Phe Ser Tyr
755 760 765

His Arg Leu Arg Asp Leu Leu Leu Ile Val Thr Arg Ile Val Glu Leu
770 775 780

Leu Gly Arg Arg Gly Trp Glu Ala Leu Lys Tyr Trp Trp Asn Leu Leu
785 790 795 800

Gln Tyr Trp Ser Gln Glu Leu Lys Asn Ser Ala Val Ser Leu Leu Asn
805 810 815

Ala Thr Ala Ile Ala Val Ala Glu Gly Thr Asp Arg Val Ile Glu Val
820 825 830

Val Gln Gly Ala Cys Arg Ala Ile Arg His Ile Pro Arg Arg Ile Arg
835 840 845

Gln Gly Leu Glu Arg Ile Leu Leu
850 855

<210> SEQ ID NO 28
<211> LENGTH: 504
<212> TYPE: PRT
<213> ORGANISM: Artificial sequence
<220> FEATURE:
<223> OTHER INFORMATION: synthetic sequence

<400> SEQUENCE: 28

Met Pro Met Gly Ser Leu Gln Pro Leu Ala Thr Leu Tyr Leu Leu Gly

-continued

```
1               5                   10                  15

Met Leu Val Ala Ser Val Leu Ala Ala Glu Asn Leu Trp Val Thr Val
            20                  25                  30

Tyr Tyr Gly Val Pro Val Trp Lys Asp Ala Glu Thr Thr Leu Phe Cys
        35                  40                  45

Ala Ser Asp Ala Lys Ala Tyr Glu Thr Glu Lys His Asn Val Trp Ala
    50                  55                  60

Thr His Ala Cys Val Pro Thr Asp Pro Asn Pro Gln Glu Ile His Leu
65                  70                  75                  80

Glu Asn Val Thr Glu Glu Phe Asn Met Trp Lys Asn Asn Met Val Glu
                85                  90                  95

Gln Met His Thr Asp Ile Ile Ser Ala Trp Asp Gln Ser Leu Lys Pro
            100                 105                 110

Cys Val Lys Leu Thr Pro Leu Cys Val Thr Leu Gln Cys Thr Asn Val
        115                 120                 125

Thr Asn Asn Ile Thr Asp Asp Met Arg Gly Glu Leu Lys Asn Cys Ser
    130                 135                 140

Phe Asn Met Thr Thr Glu Leu Arg Asp Lys Lys Gln Lys Val Tyr Ser
145                 150                 155                 160

Leu Phe Tyr Arg Leu Asp Val Val Gln Ile Asn Glu Asn Gln Gly Asn
                165                 170                 175

Arg Ser Asn Asn Ser Asn Lys Glu Tyr Arg Leu Ile Asn Cys Asn Thr
            180                 185                 190

Ser Ala Ile Thr Gln Ala Cys Pro Lys Val Ser Phe Glu Pro Ile Pro
        195                 200                 205

Ile His Tyr Cys Ala Pro Ala Gly Phe Ala Ile Leu Lys Cys Lys Asp
    210                 215                 220

Lys Lys Phe Asn Gly Thr Gly Pro Cys Pro Ser Val Ser Thr Val Gln
225                 230                 235                 240

Cys Thr His Gly Ile Lys Pro Val Val Ser Thr Gln Leu Leu Leu Asn
                245                 250                 255

Gly Ser Leu Ala Glu Glu Glu Val Met Ile Arg Ser Glu Asn Ile Thr
            260                 265                 270

Asn Asn Ala Lys Asn Ile Leu Val Gln Phe Asn Thr Pro Val Gln Ile
        275                 280                 285

Asn Cys Thr Arg Pro Asn Asn Asn Thr Arg Lys Ser Ile Arg Ile Gly
    290                 295                 300

Pro Gly Gln Ala Phe Tyr Ala Thr Gly Asp Ile Ile Gly Asp Ile Arg
305                 310                 315                 320

Gln Ala His Cys Asn Val Ser Lys Ala Thr Trp Asn Glu Thr Leu Gly
                325                 330                 335

Lys Val Val Lys Gln Leu Arg Lys His Phe Gly Asn Asn Thr Ile Ile
            340                 345                 350

Arg Phe Ala Asn Ser Ser Gly Gly Asp Leu Glu Val Thr Thr His Ser
        355                 360                 365

Phe Asn Cys Gly Gly Glu Phe Phe Tyr Cys Asn Thr Ser Gly Leu Phe
    370                 375                 380

Asn Ser Thr Trp Ile Ser Asn Thr Ser Val Gln Gly Ser Asn Ser Thr
385                 390                 395                 400

Gly Ser Asn Asp Ser Ile Thr Leu Pro Cys Arg Ile Lys Gln Ile Ile
                405                 410                 415

Asn Met Trp Gln Arg Ile Gly Gln Ala Met Tyr Ala Pro Pro Ile Gln
            420                 425                 430
```

```
Gly Val Ile Arg Cys Val Ser Asn Ile Thr Gly Leu Ile Leu Thr Arg
        435                 440                 445

Asp Gly Gly Ser Thr Asn Ser Thr Thr Glu Thr Phe Arg Pro Gly Gly
    450                 455                 460

Gly Asp Met Arg Asp Asn Trp Arg Ser Glu Leu Tyr Lys Tyr Lys Val
465                 470                 475                 480

Val Lys Ile Glu Pro Leu Gly Val Ala Pro Thr Arg Ala Lys Ser Ser
                485                 490                 495

Val Val Gly Ser Glu Lys Ser Gly
            500


<210> SEQ ID NO 29
<211> LENGTH: 23
<212> TYPE: PRT
<213> ORGANISM: Artificial sequence
<220> FEATURE:
<223> OTHER INFORMATION: synthetic sequence

<400> SEQUENCE: 29

Gly Thr Thr Gly Ala Cys Ala Gly Cys Cys Gly Cys Thr Cys Ala Thr
1               5                   10                  15

Gly Thr Thr Gly Thr Gly Gly
            20


<210> SEQ ID NO 30
<211> LENGTH: 23
<212> TYPE: PRT
<213> ORGANISM: Artificial sequence
<220> FEATURE:
<223> OTHER INFORMATION: synthetic sequence

<400> SEQUENCE: 30

Gly Thr Thr Gly Ala Cys Ala Gly Cys Cys Gly Cys Thr Cys Ala Thr
1               5                   10                  15

Gly Thr Thr Gly Thr Gly Gly
            20


<210> SEQ ID NO 31
<211> LENGTH: 35
<212> TYPE: PRT
<213> ORGANISM: Artificial sequence
<220> FEATURE:
<223> OTHER INFORMATION: synthetic sequence

<400> SEQUENCE: 31

Cys Thr Arg Pro Asn Asn Asn Thr Arg Lys Ser Ile Arg Ile Gln Arg
1               5                   10                  15

Gly Pro Gly Arg Ala Phe Val Ile Gly Lys Ile Gly Asn Met Arg Gln
            20                  25                  30

Ala His Cys
        35


<210> SEQ ID NO 32
<211> LENGTH: 515
<212> TYPE: PRT
<213> ORGANISM: Artificial sequence
<220> FEATURE:
<223> OTHER INFORMATION: synthetic sequence

<400> SEQUENCE: 32

Met Arg Val Met Gly Thr Gln Lys Asn Cys Gln Gln Trp Trp Ile Trp
1               5                   10                  15
```

-continued

```
Gly Ile Leu Gly Phe Trp Met Leu Met Ile Cys Asn Thr Lys Asp Leu
            20                  25                  30

Trp Val Thr Val Tyr Tyr Gly Val Pro Val Trp Arg Glu Ala Lys Thr
        35                  40                  45

Thr Leu Phe Cys Ala Ser Asp Ala Lys Ala Tyr Glu Thr Glu Val His
    50                  55                  60

Asn Val Trp Ala Thr His Ala Cys Val Pro Thr Asp Pro Asn Pro Gln
65                  70                  75                  80

Glu Ile Val Leu Gly Asn Val Thr Glu Asn Phe Asn Met Trp Lys Asn
                85                  90                  95

Asp Met Ala Asp Gln Met His Glu Asp Ile Ile Ser Leu Trp Asp Gln
            100                 105                 110

Ser Leu Lys Pro Cys Val Lys Leu Thr Pro Leu Cys Val Thr Leu Asn
        115                 120                 125

Cys Thr Glu Thr Asn Val Thr Gly Asn Arg Thr Val Ile Gly Asn Thr
    130                 135                 140

Asn Asp Thr Asn Ile Ala Asn Ala Thr Tyr Lys Tyr Glu Glu Met Lys
145                 150                 155                 160

Asn Cys Ser Phe Asn Val Thr Thr Glu Leu Arg Asn Lys Lys His Lys
                165                 170                 175

Glu Tyr Ala Leu Phe Tyr Arg Leu Asp Ile Val Pro Leu Asn Glu Asn
            180                 185                 190

Gly Asp Asn Ser Lys Tyr Arg Leu Ile Asn Cys Asn Thr Ser Ala Ile
        195                 200                 205

Thr Gln Ala Cys Pro Lys Val Ser Phe Asp Pro Ile Pro Ile His Tyr
    210                 215                 220

Cys Ala Pro Ala Gly Tyr Ala Ile Leu Lys Cys Asn Asn Lys Thr Phe
225                 230                 235                 240

Asn Gly Thr Gly Pro Cys Tyr Asn Val Ser Thr Val Gln Cys Thr His
                245                 250                 255

Gly Ile Lys Pro Val Val Ser Thr Gln Leu Leu Leu Asn Gly Ser Leu
            260                 265                 270

Ala Glu Glu Gly Met Ile Ile Arg Ser Glu Asn Leu Thr Glu Asn Thr
        275                 280                 285

Lys Thr Ile Ile Val His Leu Asn Glu Ser Val Glu Ile Asn Cys Thr
    290                 295                 300

Arg Pro Asn Asn Asn Thr Arg Lys Ser Val Arg Ile Gly Pro Gly Gln
305                 310                 315                 320

Ala Phe Tyr Ala Thr Asn Asp Val Ile Gly Asp Ile Arg Gln Ala His
                325                 330                 335

Cys Asn Ile Ser Thr Asp Arg Trp Asn Lys Thr Leu Gln Gln Val Met
            340                 345                 350

Lys Lys Leu Gly Glu His Phe Pro Asn Lys Thr Ile Gln Phe Lys Pro
        355                 360                 365

His Ala Gly Gly Asp Ile Glu Ile Thr Met His Ser Phe Asn Cys Arg
    370                 375                 380

Gly Glu Phe Phe Tyr Cys Asn Thr Ser Asn Leu Phe Asn Ser Thr Tyr
385                 390                 395                 400

His Ser Asn Asn Gly Thr Tyr Lys Tyr Asn Gly Asn Ser Ser Ser Pro
                405                 410                 415

Ile Thr Leu Gln Cys Lys Ile Lys Gln Ile Val Arg Met Trp Gln Gly
            420                 425                 430
```

Val Gly Gln Ala Met Tyr Ala Pro Pro Ile Ala Gly Asn Ile Thr Cys
435 440 445

Arg Ser Asn Ile Thr Gly Ile Leu Leu Thr Arg Asp Gly Gly Phe Asn
450 455 460

Thr Thr Asn Asn Thr Glu Thr Phe Arg Pro Gly Gly Gly Asp Met Arg
465 470 475 480

Asp Asn Trp Arg Ser Glu Leu Tyr Lys Tyr Lys Val Val Glu Ile Lys
485 490 495

Pro Leu Gly Ile Ala Pro Thr Lys Ala Lys Arg Arg Val Val Gln Arg
500 505 510

Glu Lys Arg
515

<210> SEQ ID NO 33
<211> LENGTH: 8
<212> TYPE: PRT
<213> ORGANISM: Artificial sequence
<220> FEATURE:
<223> OTHER INFORMATION: synthetic sequence
<220> FEATURE:
<221> NAME/KEY: misc_feature
<222> LOCATION: (1)..(8)
<223> OTHER INFORMATION: Xaa can be any naturally occurring amino acid

<400> SEQUENCE: 33

Xaa Xaa Xaa Xaa Xaa Xaa Xaa Xaa
1 5

<210> SEQ ID NO 34
<211> LENGTH: 687
<212> TYPE: PRT
<213> ORGANISM: Artificial sequence
<220> FEATURE:
<223> OTHER INFORMATION: synthetic sequence

<400> SEQUENCE: 34

Met Arg Val Met Gly Thr Gln Lys Asn Cys Gln Gln Trp Trp Ile Trp
1 5 10 15

Gly Ile Leu Gly Phe Trp Met Leu Met Ile Cys Asn Thr Lys Asp Leu
20 25 30

Trp Val Thr Val Tyr Tyr Gly Val Pro Val Trp Arg Glu Ala Lys Thr
35 40 45

Thr Leu Phe Cys Ala Ser Asp Ala Lys Ala Tyr Glu Thr Glu Val His
50 55 60

Asn Val Trp Ala Thr His Ala Cys Val Pro Thr Asp Pro Asn Pro Gln
65 70 75 80

Glu Ile Val Leu Gly Asn Val Thr Glu Asn Phe Asn Met Trp Lys Asn
85 90 95

Asp Met Ala Asp Gln Met His Glu Asp Ile Ile Ser Leu Trp Asp Gln
100 105 110

Ser Leu Lys Pro Cys Val Lys Leu Thr Pro Leu Cys Val Thr Leu Asn
115 120 125

Cys Thr Glu Thr Asn Val Thr Gly Asn Arg Thr Val Ile Gly Asn Thr
130 135 140

Asn Asp Thr Asn Ile Ala Asn Ala Thr Tyr Lys Tyr Glu Glu Met Lys
145 150 155 160

Asn Cys Ser Phe Asn Val Thr Thr Glu Leu Arg Asn Lys Lys His Lys
165 170 175

Glu Tyr Ala Leu Phe Tyr Arg Leu Asp Ile Val Pro Leu Asn Glu Asn

```
            180                 185                 190

Gly Asp Asn Ser Lys Tyr Arg Leu Ile Asn Cys Asn Thr Ser Ala Ile
        195                 200                 205

Thr Gln Ala Cys Pro Lys Val Ser Phe Asp Pro Ile Pro Ile His Tyr
    210                 215                 220

Cys Ala Pro Ala Gly Tyr Ala Ile Leu Lys Cys Asn Asn Lys Thr Phe
225                 230                 235                 240

Asn Gly Thr Gly Pro Cys Tyr Asn Val Ser Thr Val Gln Cys Thr His
                245                 250                 255

Gly Ile Lys Pro Val Val Ser Thr Gln Leu Leu Leu Asn Gly Ser Leu
            260                 265                 270

Ala Glu Glu Gly Met Ile Ile Arg Ser Glu Asn Leu Thr Glu Asn Thr
        275                 280                 285

Lys Thr Ile Ile Val His Leu Asn Glu Ser Val Glu Ile Asn Cys Thr
    290                 295                 300

Arg Pro Asn Asn Asn Thr Arg Lys Ser Val Arg Ile Gly Pro Gly Gln
305                 310                 315                 320

Ala Phe Tyr Ala Thr Asn Asp Val Ile Gly Asp Ile Arg Gln Ala His
                325                 330                 335

Cys Asn Ile Ser Thr Asp Arg Trp Asn Lys Thr Leu Gln Gln Val Met
            340                 345                 350

Lys Lys Leu Gly Glu His Phe Pro Asn Lys Thr Ile Gln Phe Lys Pro
        355                 360                 365

His Ala Gly Gly Asp Ile Glu Ile Thr Met His Ser Phe Asn Cys Arg
    370                 375                 380

Gly Glu Phe Phe Tyr Cys Asn Thr Ser Asn Leu Phe Asn Ser Thr Tyr
385                 390                 395                 400

His Ser Asn Asn Gly Thr Tyr Lys Tyr Asn Gly Asn Ser Ser Ser Pro
                405                 410                 415

Ile Thr Leu Gln Cys Lys Ile Lys Gln Ile Val Arg Met Trp Gln Gly
            420                 425                 430

Val Gly Gln Ala Met Tyr Ala Pro Pro Ile Ala Gly Asn Ile Thr Cys
        435                 440                 445

Arg Ser Asn Ile Thr Gly Ile Leu Leu Thr Arg Asp Gly Gly Phe Asn
    450                 455                 460

Thr Thr Asn Asn Thr Glu Thr Phe Arg Pro Gly Gly Gly Asp Met Arg
465                 470                 475                 480

Asp Asn Trp Arg Ser Glu Leu Tyr Lys Tyr Lys Val Val Glu Ile Lys
                485                 490                 495

Pro Leu Gly Ile Ala Pro Thr Lys Ala Lys Arg Arg Val Val Gln Arg
            500                 505                 510

Glu Lys Arg Ala Val Gly Ile Gly Ala Val Phe Leu Gly Phe Leu Gly
        515                 520                 525

Ala Ala Gly Ser Thr Met Gly Ala Ala Ser Ile Thr Leu Thr Val Gln
    530                 535                 540

Ala Arg Gln Leu Leu Ser Gly Ile Val Gln Gln Gln Ser Asn Leu Leu
545                 550                 555                 560

Lys Ala Ile Glu Ala Gln Gln His Met Leu Gln Leu Thr Val Trp Gly
                565                 570                 575

Ile Lys Gln Leu Gln Ala Arg Val Leu Ala Ile Glu Arg Tyr Leu Lys
            580                 585                 590

Asp Gln Gln Leu Leu Gly Ile Trp Gly Cys Ser Gly Arg Leu Ile Cys
        595                 600                 605
```

Thr Thr Ala Val Pro Trp Asn Ser Ser Trp Ser Asn Lys Ser Glu Ala
    610                 615                 620

Asp Ile Trp Asp Asn Met Thr Trp Met Gln Trp Asp Arg Glu Ile Asn
625                 630                 635                 640

Asn Tyr Thr Glu Ala Ile Phe Arg Leu Leu Glu Asp Ser Gln Asn Gln
                645                 650                 655

Gln Glu Lys Asn Glu Lys Asp Leu Leu Glu Leu Asp Lys Trp Asn Ser
            660                 665                 670

Leu Trp Asn Trp Phe Asn Ile Ser Asn Trp Leu Trp Tyr Ile Lys
        675                 680                 685

<210> SEQ ID NO 35
<211> LENGTH: 8
<212> TYPE: PRT
<213> ORGANISM: Artificial sequence
<220> FEATURE:
<223> OTHER INFORMATION: synthetic sequence
<220> FEATURE:
<221> NAME/KEY: misc_feature
<222> LOCATION: (1)..(8)
<223> OTHER INFORMATION: Xaa can be any naturally occurring amino acid

<400> SEQUENCE: 35

Xaa Xaa Xaa Xaa Xaa Xaa Xaa Xaa
1               5

<210> SEQ ID NO 36
<211> LENGTH: 488
<212> TYPE: PRT
<213> ORGANISM: Artificial sequence
<220> FEATURE:
<223> OTHER INFORMATION: synthetic sequence

<400> SEQUENCE: 36

Met Arg Val Arg Gly Ile Trp Lys Asn Trp Pro Gln Trp Leu Ile Trp
1               5                   10                  15

Ser Ile Leu Gly Phe Trp Ile Gly Asn Met Glu Gly Ser Trp Val Thr
            20                  25                  30

Val Tyr Tyr Gly Val Pro Val Trp Lys Glu Ala Lys Thr Thr Leu Phe
        35                  40                  45

Cys Ala Ser Asp Ala Lys Ala Tyr Glu Lys Glu Val His Asn Val Trp
    50                  55                  60

Ala Thr His Ala Cys Val Pro Thr Asp Pro Asn Pro Gln Glu Met Val
65                  70                  75                  80

Leu Ala Asn Val Thr Glu Asn Phe Asn Met Trp Lys Asn Asp Met Val
                85                  90                  95

Glu Gln Met His Glu Asp Ile Ile Ser Leu Trp Asp Glu Ser Leu Lys
            100                 105                 110

Pro Cys Val Lys Leu Thr Pro Leu Cys Val Thr Leu Asn Cys Thr Asn
        115                 120                 125

Val Lys Gly Asn Glu Ser Asp Thr Ser Glu Val Met Lys Asn Cys Ser
    130                 135                 140

Phe Lys Ala Thr Thr Glu Leu Lys Asp Lys Lys His Lys Val His Ala
145                 150                 155                 160

Leu Phe Tyr Lys Leu Asp Val Val Pro Leu Asn Gly Asn Ser Ser Ser
                165                 170                 175

Ser Gly Glu Tyr Arg Leu Ile Asn Cys Asn Thr Ser Ala Ile Thr Gln
            180                 185                 190

-continued

```
Ala Cys Pro Lys Val Ser Phe Asp Pro Ile Pro Leu His Tyr Cys Ala
        195                 200                 205

Pro Ala Gly Phe Ala Ile Leu Lys Cys Asn Asn Lys Thr Phe Asn Gly
    210                 215                 220

Thr Gly Pro Cys Arg Asn Val Ser Thr Val Gln Cys Thr His Gly Ile
225                 230                 235                 240

Lys Pro Val Val Ser Thr Gln Leu Leu Leu Asn Gly Ser Leu Ala Glu
                245                 250                 255

Glu Glu Ile Ile Ile Arg Ser Glu Asn Leu Thr Asn Asn Ala Lys Thr
            260                 265                 270

Ile Ile Val His Leu Asn Glu Ser Val Asn Ile Val Cys Thr Arg Pro
        275                 280                 285

Asn Asn Asn Thr Arg Lys Ser Ile Arg Ile Gly Pro Gly Gln Thr Phe
    290                 295                 300

Tyr Ala Thr Gly Asp Ile Ile Gly Asn Ile Arg Gln Ala His Cys Asn
305                 310                 315                 320

Ile Asn Glu Ser Lys Trp Asn Asn Thr Leu Gln Lys Val Gly Glu Glu
                325                 330                 335

Leu Ala Lys His Phe Pro Ser Lys Thr Ile Lys Phe Glu Pro Ser Ser
            340                 345                 350

Gly Gly Asp Leu Glu Ile Thr Thr His Ser Phe Asn Cys Arg Gly Glu
        355                 360                 365

Phe Phe Tyr Cys Asn Thr Ser Asp Leu Phe Asn Gly Thr Tyr Arg Asn
    370                 375                 380

Gly Thr Tyr Asn His Thr Gly Arg Ser Ser Asn Gly Thr Ile Thr Leu
385                 390                 395                 400

Gln Cys Lys Ile Lys Gln Ile Ile Asn Met Trp Gln Glu Val Gly Arg
                405                 410                 415

Ala Ile Tyr Ala Pro Pro Ile Glu Gly Glu Ile Thr Cys Asn Ser Asn
            420                 425                 430

Ile Thr Gly Leu Leu Leu Leu Arg Asp Gly Gly Gln Ser Asn Glu Thr
        435                 440                 445

Asn Asp Thr Glu Thr Phe Arg Pro Gly Gly Gly Asp Met Arg Asp Asn
    450                 455                 460

Trp Arg Ser Glu Leu Tyr Lys Tyr Lys Val Val Glu Ile Lys Pro Leu
465                 470                 475                 480

Gly Val Ala Pro Thr Glu Ala Lys
                485


<210> SEQ ID NO 37
<211> LENGTH: 8
<212> TYPE: PRT
<213> ORGANISM: Artificial sequence
<220> FEATURE:
<223> OTHER INFORMATION: synthetic sequence
<220> FEATURE:
<221> NAME/KEY: misc_feature
<222> LOCATION: (1)..(8)
<223> OTHER INFORMATION: Xaa can be any naturally occurring amino acid

<400> SEQUENCE: 37

Xaa Xaa Xaa Xaa Xaa Xaa Xaa Xaa
1               5


<210> SEQ ID NO 38
<211> LENGTH: 669
<212> TYPE: PRT
<213> ORGANISM: Artificial sequence
```

<220> FEATURE:
<223> OTHER INFORMATION: synthetic sequence

<400> SEQUENCE: 38

```
Met Arg Val Arg Gly Ile Trp Lys Asn Trp Pro Gln Trp Leu Ile Trp
1               5                   10                  15

Ser Ile Leu Gly Phe Trp Ile Gly Asn Met Glu Gly Ser Trp Val Thr
            20                  25                  30

Val Tyr Tyr Gly Val Pro Val Trp Lys Glu Ala Lys Thr Thr Leu Phe
        35                  40                  45

Cys Ala Ser Asp Ala Lys Ala Tyr Glu Lys Glu Val His Asn Val Trp
    50                  55                  60

Ala Thr His Ala Cys Val Pro Thr Asp Pro Asn Pro Gln Glu Met Val
65                  70                  75                  80

Leu Ala Asn Val Thr Glu Asn Phe Asn Met Trp Lys Asn Asp Met Val
                85                  90                  95

Glu Gln Met His Glu Asp Ile Ile Ser Leu Trp Asp Glu Ser Leu Lys
            100                 105                 110

Pro Cys Val Lys Leu Thr Pro Leu Cys Val Thr Leu Asn Cys Thr Asn
        115                 120                 125

Val Lys Gly Asn Glu Ser Asp Thr Ser Glu Val Met Lys Asn Cys Ser
    130                 135                 140

Phe Lys Ala Thr Thr Glu Leu Lys Asp Lys Lys His Lys Val His Ala
145                 150                 155                 160

Leu Phe Tyr Lys Leu Asp Val Val Pro Leu Asn Gly Asn Ser Ser Ser
                165                 170                 175

Ser Gly Glu Tyr Arg Leu Ile Asn Cys Asn Thr Ser Ala Ile Thr Gln
            180                 185                 190

Ala Cys Pro Lys Val Ser Phe Asp Pro Ile Pro Leu His Tyr Cys Ala
        195                 200                 205

Pro Ala Gly Phe Ala Ile Leu Lys Cys Asn Asn Lys Thr Phe Asn Gly
    210                 215                 220

Thr Gly Pro Cys Arg Asn Val Ser Thr Val Gln Cys Thr His Gly Ile
225                 230                 235                 240

Lys Pro Val Val Ser Thr Gln Leu Leu Leu Asn Gly Ser Leu Ala Glu
                245                 250                 255

Glu Glu Ile Ile Ile Arg Ser Glu Asn Leu Thr Asn Asn Ala Lys Thr
            260                 265                 270

Ile Ile Val His Leu Asn Glu Ser Val Asn Ile Val Cys Thr Arg Pro
        275                 280                 285

Asn Asn Asn Thr Arg Lys Ser Ile Arg Ile Gly Pro Gly Gln Thr Phe
    290                 295                 300

Tyr Ala Thr Gly Asp Ile Ile Gly Asn Ile Arg Gln Ala His Cys Asn
305                 310                 315                 320

Ile Asn Glu Ser Lys Trp Asn Asn Thr Leu Gln Lys Val Gly Glu Glu
                325                 330                 335

Leu Ala Lys His Phe Pro Ser Lys Thr Ile Lys Phe Glu Pro Ser Ser
            340                 345                 350

Gly Gly Asp Leu Glu Ile Thr Thr His Ser Phe Asn Cys Arg Gly Glu
        355                 360                 365

Phe Phe Tyr Cys Asn Thr Ser Asp Leu Phe Asn Gly Thr Tyr Arg Asn
    370                 375                 380

Gly Thr Tyr Asn His Thr Gly Arg Ser Ser Asn Gly Thr Ile Thr Leu
385                 390                 395                 400
```

```
Gln Cys Lys Ile Lys Gln Ile Ile Asn Met Trp Gln Glu Val Gly Arg
                405                 410                 415

Ala Ile Tyr Ala Pro Pro Ile Glu Gly Glu Ile Thr Cys Asn Ser Asn
            420                 425                 430

Ile Thr Gly Leu Leu Leu Leu Arg Asp Gly Gly Gln Ser Asn Glu Thr
        435                 440                 445

Asn Asp Thr Glu Thr Phe Arg Pro Gly Gly Gly Asp Met Arg Asp Asn
    450                 455                 460

Trp Arg Ser Glu Leu Tyr Lys Tyr Lys Val Val Glu Ile Lys Pro Leu
465                 470                 475                 480

Gly Val Ala Pro Thr Glu Ala Lys Arg Arg Val Val Glu Arg Glu Lys
                485                 490                 495

Arg Ala Val Gly Ile Gly Ala Val Phe Leu Gly Phe Leu Gly Ala Ala
            500                 505                 510

Gly Ser Thr Met Gly Ala Ala Ser Met Thr Leu Thr Val Gln Ala Arg
        515                 520                 525

Gln Leu Leu Ser Gly Ile Val Gln Gln Gln Ser Asn Leu Leu Arg Ala
    530                 535                 540

Ile Glu Ala Gln Gln His Met Leu Gln Leu Thr Val Trp Gly Ile Lys
545                 550                 555                 560

Gln Leu Gln Ala Arg Val Leu Ala Ile Glu Arg Tyr Leu Lys Asp Gln
                565                 570                 575

Gln Leu Leu Gly Met Trp Gly Cys Ser Gly Lys Leu Ile Cys Thr Thr
            580                 585                 590

Ala Val Pro Trp Asn Ser Ser Trp Ser Asn Lys Ser Gln Asn Glu Ile
        595                 600                 605

Trp Gly Asn Met Thr Trp Met Gln Trp Asp Arg Glu Ile Asn Asn Tyr
    610                 615                 620

Thr Asn Thr Ile Tyr Arg Leu Leu Glu Asp Ser Gln Asn Gln Gln Glu
625                 630                 635                 640

Lys Asn Glu Lys Asp Leu Leu Ala Leu Asp Ser Trp Lys Asn Leu Trp
                645                 650                 655

Asn Trp Phe Asp Ile Ser Lys Trp Leu Trp Tyr Ile Lys
            660                 665


<210> SEQ ID NO 39
<211> LENGTH: 8
<212> TYPE: PRT
<213> ORGANISM: Artificial sequence
<220> FEATURE:
<223> OTHER INFORMATION: synthetic sequence
<220> FEATURE:
<221> NAME/KEY: misc_feature
<222> LOCATION: (1)..(8)
<223> OTHER INFORMATION: Xaa can be any naturally occurring amino acid

<400> SEQUENCE: 39

Xaa Xaa Xaa Xaa Xaa Xaa Xaa Xaa
1               5


<210> SEQ ID NO 40
<211> LENGTH: 492
<212> TYPE: PRT
<213> ORGANISM: Artificial sequence
<220> FEATURE:
<223> OTHER INFORMATION: synthetic sequence

<400> SEQUENCE: 40
```

-continued

```
Met Arg Val Arg Gly Ile Leu Arg Asn Trp Pro Gln Trp Trp Ile Trp
1               5                   10                  15

Ser Ile Leu Gly Phe Trp Met Leu Ile Ile Cys Arg Val Met Gly Asn
            20                  25                  30

Leu Trp Val Thr Val Tyr Tyr Gly Val Pro Val Trp Lys Glu Ala Lys
        35                  40                  45

Ala Thr Leu Phe Cys Ala Ser Asp Ala Arg Ala Tyr Glu Lys Glu Val
    50                  55                  60

His Asn Val Trp Ala Thr His Ala Cys Val Pro Thr Asp Pro Asn Pro
65                  70                  75                  80

Gln Glu Ile Tyr Leu Gly Asn Val Thr Glu Asn Phe Asn Met Trp Lys
                85                  90                  95

Asn Asp Met Val Asp Gln Met His Glu Asp Ile Ile Ser Leu Trp Asp
            100                 105                 110

Gln Ser Leu Lys Pro Cys Val Lys Leu Thr Pro Leu Cys Val Thr Leu
        115                 120                 125

Arg Cys Thr Asn Ala Thr Ile Asn Gly Ser Leu Thr Glu Glu Val Lys
    130                 135                 140

Asn Cys Ser Phe Asn Ile Thr Thr Glu Leu Arg Asp Lys Lys Gln Lys
145                 150                 155                 160

Ala Tyr Ala Leu Phe Tyr Arg Pro Asp Val Val Pro Leu Asn Lys Asn
                165                 170                 175

Ser Pro Ser Gly Asn Ser Ser Glu Tyr Ile Leu Ile Asn Cys Asn Thr
            180                 185                 190

Ser Thr Ile Thr Gln Ala Cys Pro Lys Val Ser Phe Asp Pro Ile Pro
        195                 200                 205

Ile His Tyr Cys Ala Pro Ala Gly Tyr Ala Ile Leu Lys Cys Asn Asn
    210                 215                 220

Lys Thr Phe Asn Gly Thr Gly Pro Cys Asn Asn Val Ser Thr Val Gln
225                 230                 235                 240

Cys Thr His Gly Ile Lys Pro Val Val Ser Thr Gln Leu Leu Leu Asn
                245                 250                 255

Gly Ser Leu Ala Glu Glu Asp Ile Ile Ile Lys Ser Glu Asn Leu Thr
            260                 265                 270

Asn Asn Ile Lys Thr Ile Ile Val His Leu Asn Lys Ser Val Glu Ile
        275                 280                 285

Val Cys Arg Arg Pro Asn Asn Asn Thr Arg Lys Ser Ile Arg Ile Gly
    290                 295                 300

Pro Gly Gln Ala Phe Tyr Ala Thr Asn Asp Ile Ile Gly Asp Ile Arg
305                 310                 315                 320

Gln Ala His Cys Asn Ile Asn Asn Ser Thr Trp Asn Arg Thr Leu Glu
                325                 330                 335

Gln Ile Lys Lys Lys Leu Arg Glu His Phe Leu Asn Arg Thr Ile Glu
            340                 345                 350

Phe Glu Pro Pro Ser Gly Gly Asp Leu Glu Val Thr Thr His Ser Phe
        355                 360                 365

Asn Cys Gly Gly Glu Phe Phe Tyr Cys Asn Thr Thr Arg Leu Phe Lys
    370                 375                 380

Trp Ser Ser Asn Val Thr Asn Asp Thr Ile Thr Ile Pro Cys Arg Ile
385                 390                 395                 400

Lys Gln Phe Ile Asn Met Trp Gln Gly Ala Gly Arg Ala Met Tyr Ala
                405                 410                 415

Pro Pro Ile Glu Gly Asn Ile Thr Cys Asn Ser Ser Ile Thr Gly Leu
```

```
            420                 425                 430

Leu Leu Thr Arg Asp Gly Gly Lys Thr Asp Arg Asn Asp Thr Glu Ile
        435                 440                 445

Phe Arg Pro Gly Gly Gly Asn Met Lys Asp Asn Trp Arg Asn Glu Leu
    450                 455                 460

Tyr Lys Tyr Lys Val Val Glu Ile Lys Pro Leu Gly Val Ala Pro Thr
465                 470                 475                 480

Glu Ala Arg Arg Arg Val Val Glu Arg Glu Lys Arg
                485                 490


<210> SEQ ID NO 41
<211> LENGTH: 8
<212> TYPE: PRT
<213> ORGANISM: Artificial sequence
<220> FEATURE:
<223> OTHER INFORMATION: synthetic sequence
<220> FEATURE:
<221> NAME/KEY: misc_feature
<222> LOCATION: (1)..(8)
<223> OTHER INFORMATION: Xaa can be any naturally occurring amino acid

<400> SEQUENCE: 41

Xaa Xaa Xaa Xaa Xaa Xaa Xaa Xaa
1               5


<210> SEQ ID NO 42
<211> LENGTH: 664
<212> TYPE: PRT
<213> ORGANISM: Artificial sequence
<220> FEATURE:
<223> OTHER INFORMATION: synthetic sequence

<400> SEQUENCE: 42

Met Arg Val Arg Gly Ile Leu Arg Asn Trp Pro Gln Trp Trp Ile Trp
1               5                   10                  15

Ser Ile Leu Gly Phe Trp Met Leu Ile Ile Cys Arg Val Met Gly Asn
            20                  25                  30

Leu Trp Val Thr Val Tyr Tyr Gly Val Pro Val Trp Lys Glu Ala Lys
        35                  40                  45

Ala Thr Leu Phe Cys Ala Ser Asp Ala Arg Ala Tyr Glu Lys Glu Val
    50                  55                  60

His Asn Val Trp Ala Thr His Ala Cys Val Pro Thr Asp Pro Asn Pro
65                  70                  75                  80

Gln Glu Ile Tyr Leu Gly Asn Val Thr Glu Asn Phe Asn Met Trp Lys
                85                  90                  95

Asn Asp Met Val Asp Gln Met His Glu Asp Ile Ile Ser Leu Trp Asp
            100                 105                 110

Gln Ser Leu Lys Pro Cys Val Lys Leu Thr Pro Leu Cys Val Thr Leu
        115                 120                 125

Arg Cys Thr Asn Ala Thr Ile Asn Gly Ser Leu Thr Glu Glu Val Lys
    130                 135                 140

Asn Cys Ser Phe Asn Ile Thr Thr Glu Leu Arg Asp Lys Lys Gln Lys
145                 150                 155                 160

Ala Tyr Ala Leu Phe Tyr Arg Pro Asp Val Val Pro Leu Asn Lys Asn
                165                 170                 175

Ser Pro Ser Gly Asn Ser Ser Glu Tyr Ile Leu Ile Asn Cys Asn Thr
            180                 185                 190

Ser Thr Ile Thr Gln Ala Cys Pro Lys Val Ser Phe Asp Pro Ile Pro
        195                 200                 205
```

-continued

```
Ile His Tyr Cys Ala Pro Ala Gly Tyr Ala Ile Leu Lys Cys Asn Asn
    210                 215                 220

Lys Thr Phe Asn Gly Thr Gly Pro Cys Asn Asn Val Ser Thr Val Gln
225                 230                 235                 240

Cys Thr His Gly Ile Lys Pro Val Val Ser Thr Gln Leu Leu Leu Asn
                245                 250                 255

Gly Ser Leu Ala Glu Glu Asp Ile Ile Ile Lys Ser Glu Asn Leu Thr
            260                 265                 270

Asn Asn Ile Lys Thr Ile Ile Val His Leu Asn Lys Ser Val Glu Ile
        275                 280                 285

Val Cys Arg Arg Pro Asn Asn Asn Thr Arg Lys Ser Ile Arg Ile Gly
    290                 295                 300

Pro Gly Gln Ala Phe Tyr Ala Thr Asn Asp Ile Ile Gly Asp Ile Arg
305                 310                 315                 320

Gln Ala His Cys Asn Ile Asn Asn Ser Thr Trp Asn Arg Thr Leu Glu
                325                 330                 335

Gln Ile Lys Lys Lys Leu Arg Glu His Phe Leu Asn Arg Thr Ile Glu
            340                 345                 350

Phe Glu Pro Pro Ser Gly Gly Asp Leu Glu Val Thr Thr His Ser Phe
        355                 360                 365

Asn Cys Gly Gly Glu Phe Phe Tyr Cys Asn Thr Thr Arg Leu Phe Lys
    370                 375                 380

Trp Ser Ser Asn Val Thr Asn Asp Thr Ile Thr Ile Pro Cys Arg Ile
385                 390                 395                 400

Lys Gln Phe Ile Asn Met Trp Gln Gly Ala Gly Arg Ala Met Tyr Ala
                405                 410                 415

Pro Pro Ile Glu Gly Asn Ile Thr Cys Asn Ser Ser Ile Thr Gly Leu
            420                 425                 430

Leu Leu Thr Arg Asp Gly Gly Lys Thr Asp Arg Asn Asp Thr Glu Ile
        435                 440                 445

Phe Arg Pro Gly Gly Gly Asn Met Lys Asp Asn Trp Arg Asn Glu Leu
    450                 455                 460

Tyr Lys Tyr Lys Val Val Glu Ile Lys Pro Leu Gly Val Ala Pro Thr
465                 470                 475                 480

Glu Ala Arg Arg Arg Val Val Glu Arg Glu Lys Arg Ala Val Gly Ile
                485                 490                 495

Gly Ala Val Leu Leu Gly Phe Leu Gly Ala Ala Gly Ser Thr Met Gly
            500                 505                 510

Ala Ala Ser Ile Thr Leu Thr Val Gln Ala Arg Gln Leu Leu Ser Gly
        515                 520                 525

Ile Val Gln Gln Gln Ser Asn Leu Leu Arg Ala Ile Glu Ala Gln Gln
    530                 535                 540

His Met Leu Gln Leu Thr Val Trp Gly Ile Lys Gln Leu Gln Thr Arg
545                 550                 555                 560

Val Leu Ala Ile Glu Arg Tyr Leu Lys Asp Gln Gln Leu Leu Gly Leu
                565                 570                 575

Trp Gly Cys Ser Gly Lys Leu Ile Cys Thr Thr Asn Val Pro Trp Asn
            580                 585                 590

Ser Ser Trp Ser Asn Lys Ser Gln Thr Asp Ile Trp Asp Asn Met Thr
        595                 600                 605

Trp Ile Gln Trp Asp Arg Glu Ile Ser Asn Tyr Ser Asn Thr Ile Tyr
    610                 615                 620
```

Lys Leu Leu Glu Gly Ser Gln Asn Gln Gln Glu Gln Asn Glu Lys Asp
625 630 635 640

Leu Leu Ala Leu Asp Ser Trp Asn Asn Leu Trp Asn Trp Phe Asn Ile
645 650 655

Thr Asn Trp Leu Trp Tyr Ile Lys
660

<210> SEQ ID NO 43
<211> LENGTH: 8
<212> TYPE: PRT
<213> ORGANISM: Artificial sequence
<220> FEATURE:
<223> OTHER INFORMATION: synthetic sequence
<220> FEATURE:
<221> NAME/KEY: misc_feature
<222> LOCATION: (1)..(8)
<223> OTHER INFORMATION: Xaa can be any naturally occurring amino acid

<400> SEQUENCE: 43

Xaa Xaa Xaa Xaa Xaa Xaa Xaa Xaa
1 5

<210> SEQ ID NO 44
<211> LENGTH: 25
<212> TYPE: PRT
<213> ORGANISM: Artificial sequence
<220> FEATURE:
<223> OTHER INFORMATION: synthetic sequence

<400> SEQUENCE: 44

Met Gly Gly Ala Ala Ala Arg Leu Gly Ala Val Ile Leu Phe Val Val
1 5 10 15

Ile Val Gly Leu His Gly Val Arg Gly
20 25

<210> SEQ ID NO 45
<211> LENGTH: 21
<212> TYPE: PRT
<213> ORGANISM: Artificial sequence
<220> FEATURE:
<223> OTHER INFORMATION: synthetic sequence

<400> SEQUENCE: 45

Met Ala Tyr Pro Ala Val Ile Val Leu Val Cys Gly Leu Phe Trp Val
1 5 10 15

Pro Ala Thr Gln Gly
20

<210> SEQ ID NO 46
<211> LENGTH: 27
<212> TYPE: PRT
<213> ORGANISM: Artificial sequence
<220> FEATURE:
<223> OTHER INFORMATION: synthetic sequence

<400> SEQUENCE: 46

Met Ala Pro Ser Ser Pro Arg Pro Ala Leu Pro Ala Leu Leu Val Leu
1 5 10 15

Leu Gly Ala Leu Phe Pro Gly Pro Gly Asn Ala
20 25

<210> SEQ ID NO 47
<211> LENGTH: 36
<212> TYPE: PRT
<213> ORGANISM: Artificial sequence
<220> FEATURE:
<223> OTHER INFORMATION: synthetic sequence

<400> SEQUENCE: 47

Met Asp Ala Met Lys Arg Gly Leu Cys Cys Val Leu Leu Leu Cys Gly
1               5                   10                  15

Ala Val Phe Val Ser Pro Ser Gln Glu Ile His Ala Arg Phe Arg Arg
            20                  25                  30

Gly Ala Arg Trp
        35

<210> SEQ ID NO 48
<211> LENGTH: 27
<212> TYPE: PRT
<213> ORGANISM: Artificial sequence
<220> FEATURE:
<223> OTHER INFORMATION: synthetic sequence

<400> SEQUENCE: 48

Lys Tyr Ala Leu Ala Asp Ala Ser Leu Lys Met Ala Asp Pro Asn Arg
1               5                   10                  15

Phe Arg Gly Lys Asp Leu Pro Val Leu Asp Gln
            20                  25

<210> SEQ ID NO 49
<211> LENGTH: 27
<212> TYPE: PRT
<213> ORGANISM: Artificial sequence
<220> FEATURE:
<223> OTHER INFORMATION: synthetic sequence

<400> SEQUENCE: 49

Tyr Val Arg Ala Asp Pro Ser Leu Ser Met Val Asn Pro Asn Arg Phe
1               5                   10                  15

Arg Gly Gly His Leu Pro Pro Leu Val Gln Gln
            20                  25

<210> SEQ ID NO 50
<211> LENGTH: 11
<212> TYPE: PRT
<213> ORGANISM: Artificial sequence
<220> FEATURE:
<223> OTHER INFORMATION: synthetic sequence

<400> SEQUENCE: 50

Thr Asp Asn Leu Trp Val Thr Val Tyr Tyr Gly
1               5                   10

<210> SEQ ID NO 51
<211> LENGTH: 6
<212> TYPE: PRT
<213> ORGANISM: Artificial sequence
<220> FEATURE:
<223> OTHER INFORMATION: synthetic sequence

<400> SEQUENCE: 51

His His His His His His
1               5

<210> SEQ ID NO 52
<211> LENGTH: 15
<212> TYPE: PRT
<213> ORGANISM: Artificial sequence
<220> FEATURE:
<223> OTHER INFORMATION: synthetic sequence -continued

<400> SEQUENCE: 52

Gly Leu Asn Asp Ile Phe Glu Ala Gln Lys Ile Glu Trp His Glu
1 5 10 15

<210> SEQ ID NO 53
<211> LENGTH: 8
<212> TYPE: PRT
<213> ORGANISM: Artificial sequence
<220> FEATURE:
<223> OTHER INFORMATION: synthetic sequence

<400> SEQUENCE: 53

Trp Ser His Pro Gln Phe Glu Lys
1 5

<210> SEQ ID NO 54
<211> LENGTH: 16
<212> TYPE: PRT
<213> ORGANISM: Artificial sequence
<220> FEATURE:
<223> OTHER INFORMATION: synthetic sequence

<400> SEQUENCE: 54

His His His His His His Ser Ser Trp Ser His Pro Gln Phe Glu Lys
1 5 10 15

<210> SEQ ID NO 55
<211> LENGTH: 24
<212> TYPE: PRT
<213> ORGANISM: Artificial sequence
<220> FEATURE:
<223> OTHER INFORMATION: synthetic sequence

<400> SEQUENCE: 55

His His His His His His Ser Ser Trp Ser His Pro Gln Phe Glu Lys
1 5 10 15

Ser Ser His His His His His His
20

<210> SEQ ID NO 56
<211> LENGTH: 23
<212> TYPE: PRT
<213> ORGANISM: Artificial sequence
<220> FEATURE:
<223> OTHER INFORMATION: synthetic sequence

<400> SEQUENCE: 56

His His His His His His Trp Ser His Pro Gln Phe Glu Lys His His
1 5 10 15

His His His His Gln Ser Gly
20

<210> SEQ ID NO 57
<211> LENGTH: 8
<212> TYPE: PRT
<213> ORGANISM: Artificial sequence
<220> FEATURE:
<223> OTHER INFORMATION: synthetic sequence

<400> SEQUENCE: 57

Lys Arg Arg Val Val Gln Arg Glu
1 5

<210> SEQ ID NO 58

-continued

```
<211> LENGTH: 23
<212> TYPE: PRT
<213> ORGANISM: Artificial sequence
<220> FEATURE:
<223> OTHER INFORMATION: synthetic sequence

<400> SEQUENCE: 58

Arg Arg Val Val Glu Arg Glu Lys Arg Ala Val Gly Ile Gly Ala Val
1               5                   10                  15

Phe Leu Gly Phe Leu Gly Ala
            20
```